(12) United States Patent
Blum et al.

(10) Patent No.: US 11,053,278 B2
(45) Date of Patent: Jul. 6, 2021

(54) TANGENTIAL FLOW FILTRATION BASED PROTEIN REFOLDING METHODS

(71) Applicant: BRISTOL-MYERS SQUIBB COMPANY, Princeton, NJ (US)

(72) Inventors: Benjamin C. Blum, Boston, MA (US); Christopher Hollander, West Newton, MA (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 0 days.

(21) Appl. No.: 16/211,094

(22) Filed: Dec. 5, 2018

(65) Prior Publication Data

US 2019/0169229 A1 Jun. 6, 2019

Related U.S. Application Data

(62) Division of application No. 14/766,849, filed as application No. PCT/US2014/015658 on Feb. 11, 2014, now Pat. No. 10,183,967.

(60) Provisional application No. 61/763,670, filed on Feb. 12, 2013.

(51) Int. Cl.
| | | |
|---|---|---|
| C07K 1/113 | (2006.01) | |
| C07K 1/34 | (2006.01) | |
| C07K 16/46 | (2006.01) | |
| C07K 14/78 | (2006.01) | |
| C07K 16/18 | (2006.01) | |

(52) U.S. Cl.
CPC .............. *C07K 1/1136* (2013.01); *C07K 1/34* (2013.01); *C07K 14/78* (2013.01); *C07K 16/18* (2013.01); *C07K 2317/14* (2013.01); *C07K 2317/52* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,115,396 | B2 | 10/2006 | Lipovsek et al. |
| 7,858,739 | B2 | 12/2010 | Chen et al. |
| 8,293,482 | B2 | 10/2012 | Jacobs et al. |
| 10,065,987 | B2 | 9/2018 | Hollander et al. |
| 10,183,967 | B2 | 1/2019 | Blum et al. |
| 2009/0181430 | A1 | 7/2009 | Ferguson et al. |
| 2016/0002287 | A1 | 1/2016 | Hollander et al. |
| 2019/0077828 | A1 | 3/2019 | Hollander et al. |

FOREIGN PATENT DOCUMENTS

| | | |
|---|---|---|
| EP | 2322625 A1 | 5/2011 |
| KR | 960013392 B1 | 10/1996 |
| KR | 100247151 B1 | 3/2000 |
| KR | 20020011559 A | 2/2002 |
| WO | 199202540 A1 | 2/1992 |
| WO | 199204382 A1 | 3/1992 |
| WO | 2002/04523 A2 | 1/2002 |
| WO | 2004001056 A1 | 12/2003 |
| WO | 2004015124 A1 | 2/2004 |
| WO | 2008054592 A2 | 5/2008 |
| WO | 2009023184 A2 | 2/2009 |
| WO | 2009058379 A2 | 5/2009 |
| WO | 2009083804 A2 | 7/2009 |
| WO | 2009086116 A2 | 7/2009 |
| WO | 2009133208 A1 | 11/2009 |
| WO | 2010051274 A2 | 5/2010 |
| WO | 2010051310 A2 | 5/2010 |
| WO | 2010093627 A2 | 8/2010 |
| WO | 2011020033 A2 | 2/2011 |
| WO | 2011051333 A1 | 5/2011 |
| WO | 2011051466 A1 | 5/2011 |
| WO | 2011092233 A1 | 8/2011 |
| WO | 2011100700 A2 | 8/2011 |
| WO | 2011130324 A1 | 10/2011 |
| WO | 2011130328 A1 | 10/2011 |
| WO | 2011137319 A2 | 11/2011 |
| WO | 2011150133 A2 | 12/2011 |
| WO | 2012016245 A2 | 2/2012 |
| WO | 2012142515 A2 | 10/2012 |
| WO | 2013/067029 A2 | 5/2013 |

OTHER PUBLICATIONS

Cabrita, Lisa D., "Protein expression and refolding—A practical guide to getting the most out of inclusion bodies", Biotechnology Annual Review, vol. 10, pp. 31-50 (2004).

Carter, Paul J., "Introduction to current and future protein therapeutics: A protein engineering perspective", Experimental Cell Research, vol. 317, pp. 1261-1269 (2011).

Dasari et al., "Optimization of the downstream process for high recovery of rhG-CSF from inclusion bodies expressed in *Escherichia coli*," Process Biochem.43:566-575 (2008).

Eiberle, M. et al., "Technical refolding of proteins: Do we have freedom to operate?" Biotechnology J., vol. 5, pp. 547-559 (2010).

Grune, T. et al., "Decreased proteolysis caused by protein aggregates, inclusion bodies, plaques, lipofuscin, ceroid, and "aggresomes" during oxidative stress, aging, and disease", The International Journal of Biochemistry & Cell Biology, vol. 36,pp. 2519-2530 (2004).

Hakim R. et al., "IgGs and IgG-enzyme fusion proteins produced in an *E.coli* expression-refolding system", mAbs, vol. 1:3, pp. 281-287 (2009).

Jefferis, Royston, "Glycosylation of Recombinant Antibody Therapeutics", Biotechnol. Prog., vol. 21, pp. 11-16 (2005).

Jung. Sang Taek, "Bypassing glycosylation: engineering aglycosylated full-length IgG antibodies for human therapy", Current Opinion in Biotechnology, vol. 22, pp. 858-867 (2011).

(Continued)

*Primary Examiner* — Julie Ha
*Assistant Examiner* — Kristina M Hellman
(74) *Attorney, Agent, or Firm* — Nelson Mullins Riley & Scarborough LLP; Jane E. Remillard, Esq.; Christopher L. Frank

(57) ABSTRACT

Provided herein are methods for refolding proteins that are denatured. Exemplary methods comprise solubilizing the denatured protein with a denaturing agent, e.g., a chaotropic agent, and renaturing the protein using a buffer exchanging system, e.g., tangential flow filtration (TFF).

10 Claims, 15 Drawing Sheets

Specification includes a Sequence Listing.

(56) References Cited

OTHER PUBLICATIONS

Jungbauer, A., "Current status of technical protein refolding", J. of Biotechnology, vol. 128, pp. 587-596 (2007).
Liu, F. et al., "Improvement in soluble expression levels of a diabody by exchanging expression vectors", Protein Expression and Purification, vol. 62, pp. 15-20 (2008).
Meng, Qi et al., Large scale production of Botulium neurotoxin type A binding domain and characterization by quartz crystal microbalance biosensor technology, Abstract Univ. of California.
Presta, Leonard G., "Engineering of therapeutic antibodies to minimize immunogenicity and optimize function", Advanced Drug Delivery Reviews, vol. 58, pp. 640-656 (2006).
Rudolph, R. et al., "In vitro folding of inclusion body proteins", FASEB J. vol. 10, pp. 49-56 (1996).
Singh, Surinder et al., "Solubilization and Refolding of Bacterial Inclusion Body Proteins", J. of Bioscience and Bioengineering, vol. 99(4), pp. 303-310 (2005).
Vamerin, J. et al., "Production of Leptin in *Escherichia coli*: A Comparison of Methods", Protein Expression and Purification, vol. 14, pp. 335-342 (1998).
Wang, Qi-Rui et al., "Expression, refolding, purification, and bioactivity of recombinant bifunctional protein, hIL-2/GM-CSF", Protein Expression and Purification, vol. 39, pp. 131-136 (2005).
Yoshii, H. et al., "Refolding of Denatured/Reduced Lysozyme at High Concentration with Diafiltration", Biosci. Biotechnol. Biochem., vol. 64(6), pp. 1159-1165 (2000).
Extended European Search Report, European Application No. 20172760.9, dated Oct. 7, 2020, 12 pages.
Vallejo, L. et al., "Strategies for the recovery of active proteins through refolding of bacterial inclusion body proteins," Microbial Cell Factories, Microbial Cell Factories, vol. 3(11) 12 pages (2004).

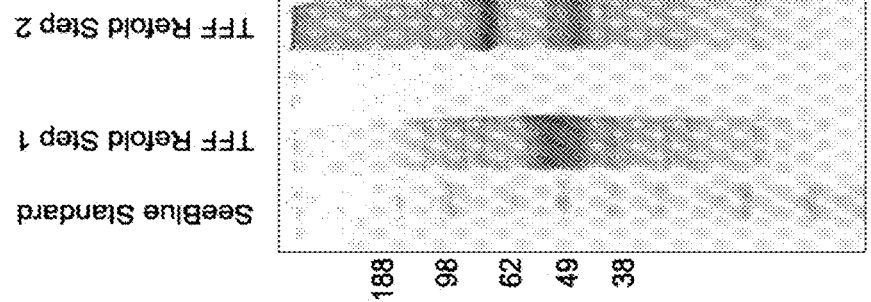
FIG. 3C
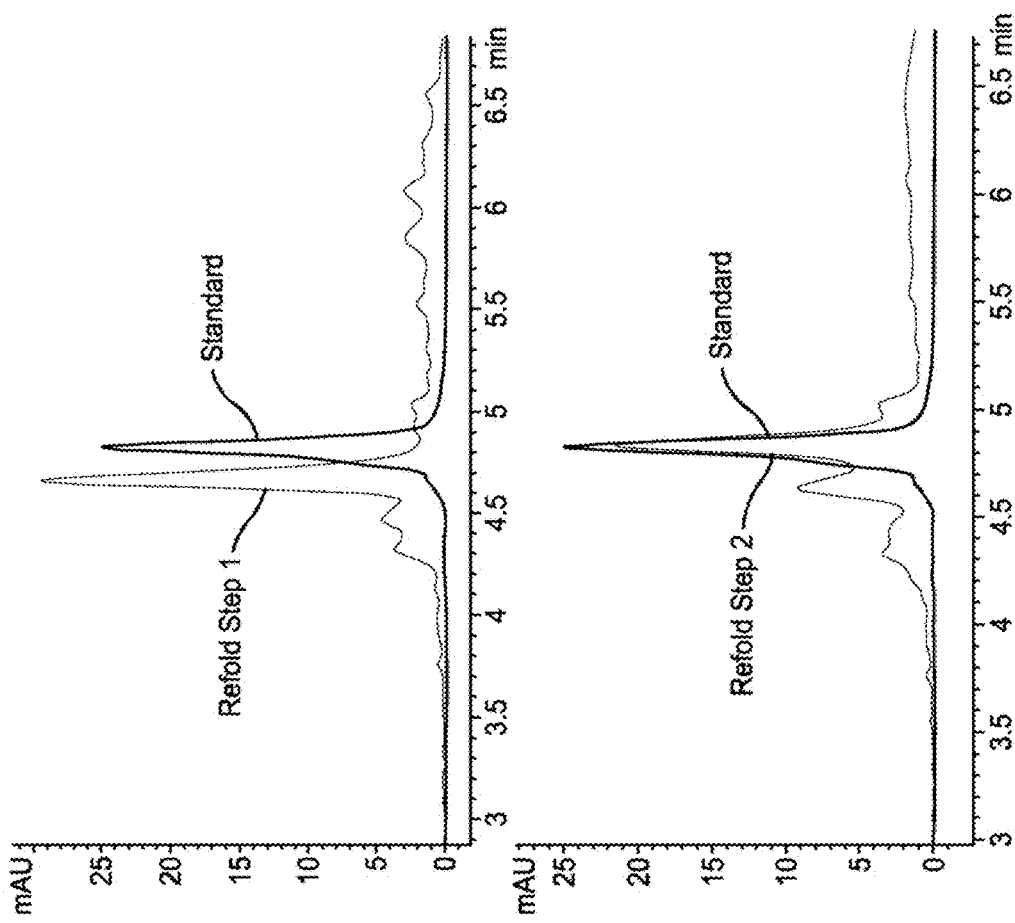
FIG. 3A
FIG. 3B

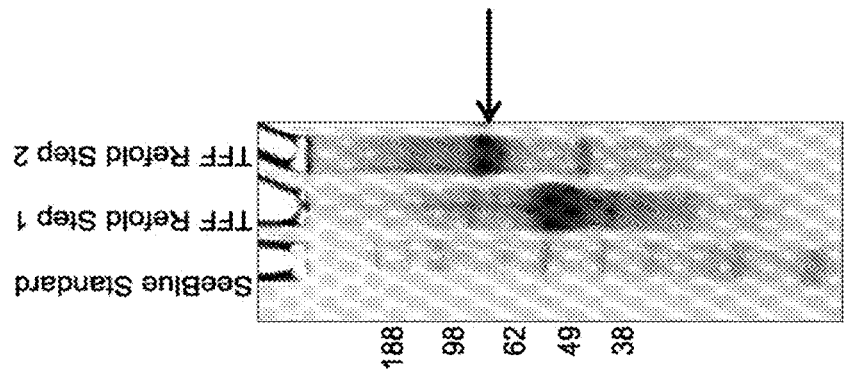
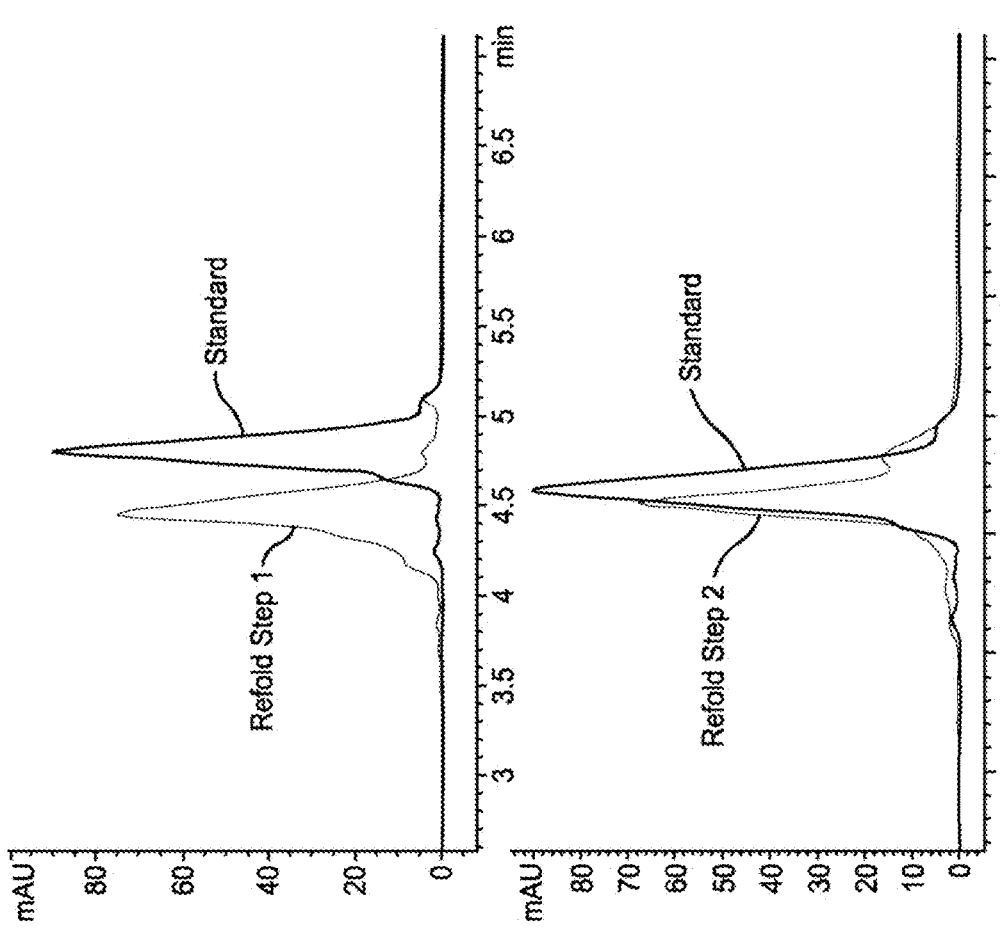
FIG. 5A
FIG. 5B
FIG. 5C

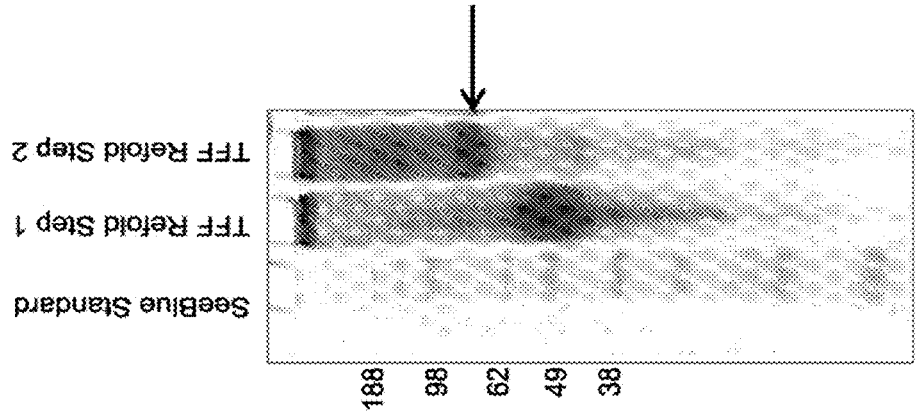
FIG. 9C
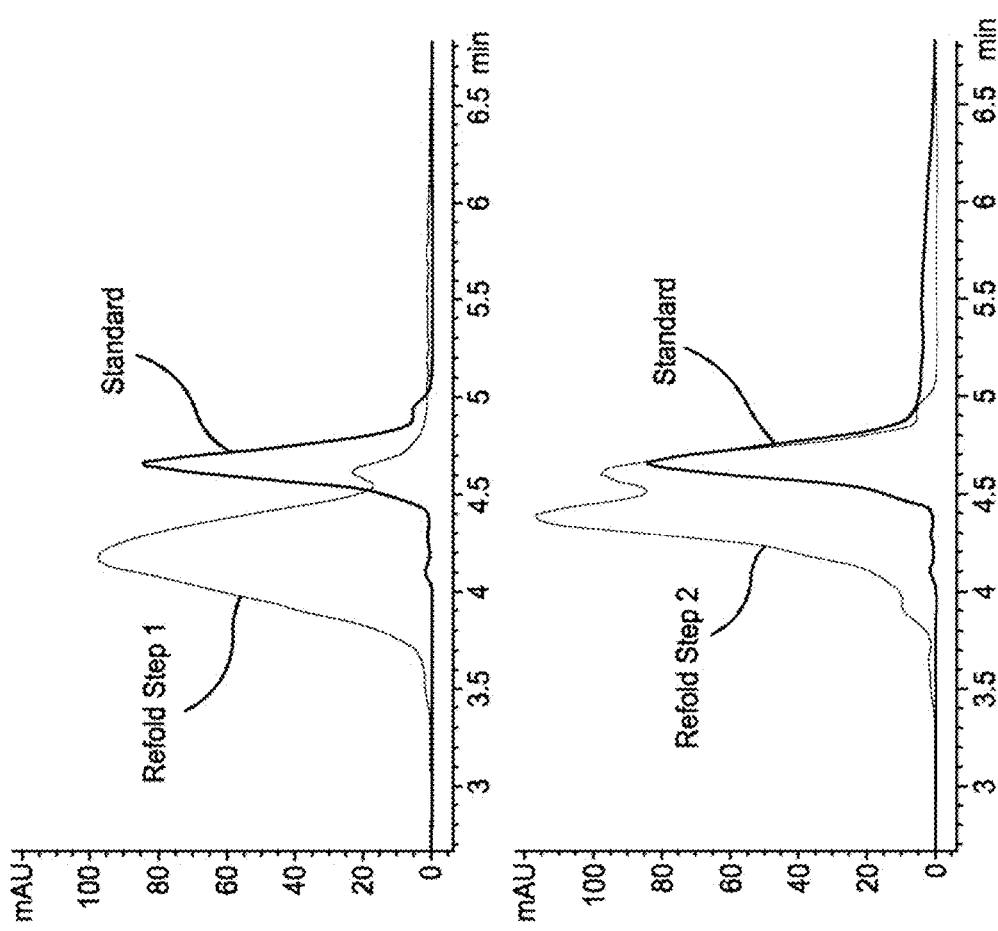
FIG. 9A
FIG. 9B

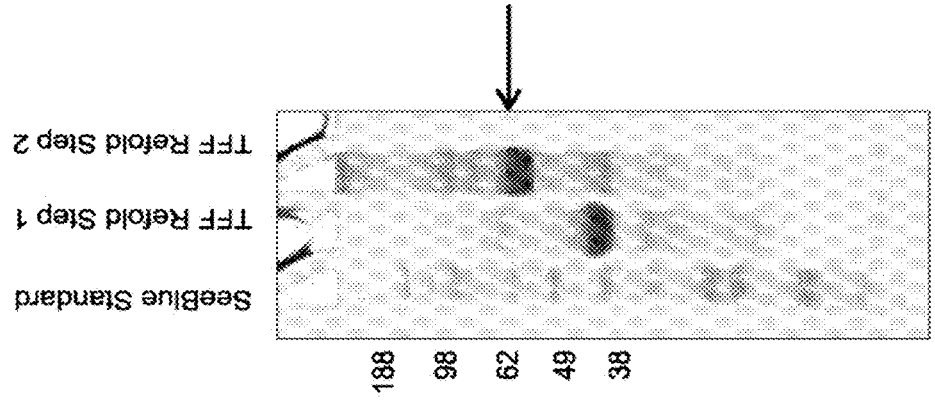
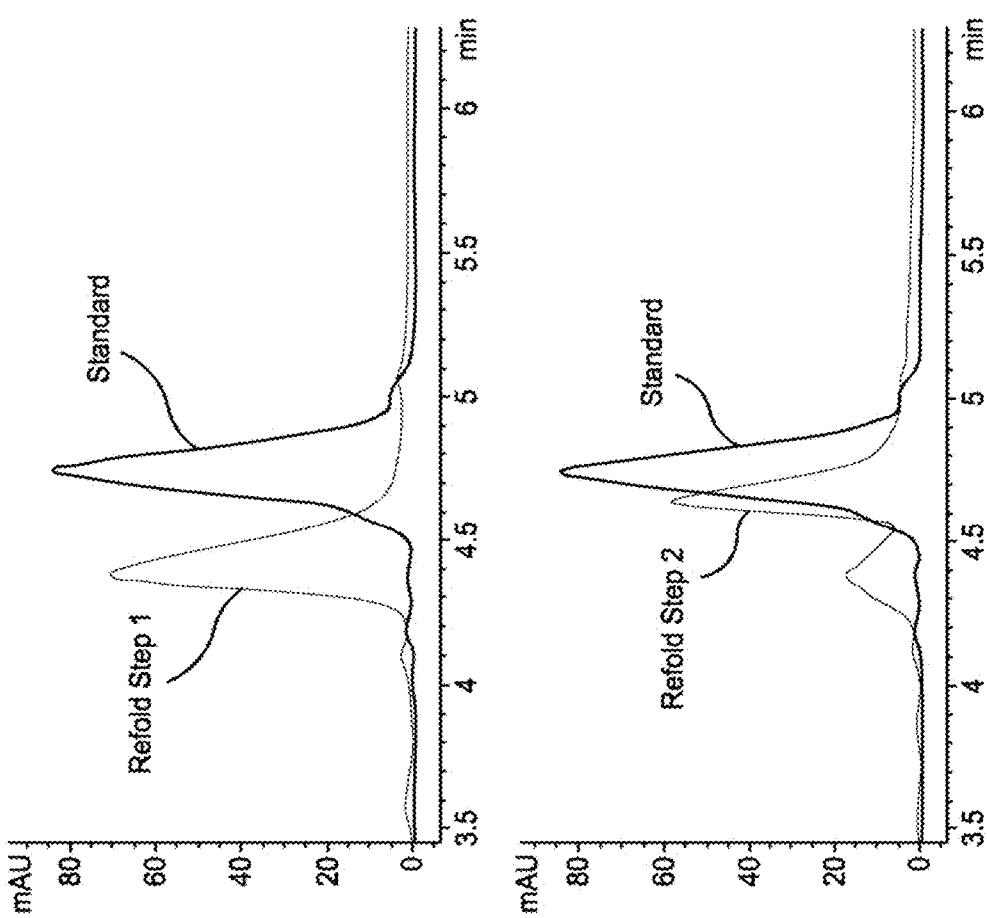
FIG. 11A
FIG. 11B
FIG. 11C

SEQUENCE LISTING

<160> NUMBER OF SEQ ID NOS: 109

<210> SEQ ID NO 1
<211> LENGTH: 101
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

```
Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Asp Lys Pro Ser Gln
            100

<210> SEQ ID NO 2
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
         35                  40                  45

Thr Val Pro Gly Ser Lys Ser Thr Ala Thr Ile Ser Gly Leu Lys Pro
     50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Glu Lys Pro Ser Gln
            100

<210> SEQ ID NO 3
<211> LENGTH: 85
<212> TYPE: PRT
<213> ORGANISM: Homo sapiens

<400> SEQUENCE: 3

Leu Glu Val Val Ala Ala Thr Pro Thr Ser Leu Leu Ile Ser Trp Asp
 1               5                  10                  15

Ala Pro Ala Val Thr Val Arg Tyr Tyr Arg Ile Thr Tyr Gly Glu Thr
             20                  25                  30

Gly Gly Asn Ser Pro Val Gln Glu Phe Thr Val Pro Gly Ser Lys Ser
         35                  40                  45

Thr Ala Thr Ile Ser Gly Leu Lys Pro Gly Val Asp Tyr Thr Ile Thr
     50                  55                  60

Val Tyr Ala Val Thr Gly Arg Gly Asp Ser Pro Ala Ser Ser Lys Pro
 65                  70                  75                  80

Ile Ser Ile Asn Tyr
             85

<210> SEQ ID NO 4
<211> LENGTH: 86
<212> TYPE: PRT
<213> ORGANISM: Homo sapiens
```

```
<400> SEQUENCE: 4

Glu Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
                20                  25                  30

Gly Asn Ser Pro Val Gln Glu Phe Thr Val Pro Gly Ser Lys Ser Thr
                35                  40                  45

Ala Thr Ile Ser Gly Leu Lys Pro Gly Val Asp Tyr Thr Ile Thr Val
50                  55                  60

Tyr Ala Val Thr Gly Arg Gly Asp Ser Pro Ala Ser Ser Lys Pro Ile
65                  70                  75                  80

Ser Ile Asn Tyr Arg Thr
                85

<210> SEQ ID NO 5
<211> LENGTH: 94
<212> TYPE: PRT
<213> ORGANISM: Homo sapiens

<400> SEQUENCE: 5

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 6
<211> LENGTH: 95
<212> TYPE: PRT
<213> ORGANISM: Homo sapiens

<400> SEQUENCE: 6

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu
                85                  90                  95

<210> SEQ ID NO 7
<211> LENGTH: 96
<212> TYPE: PRT
<213> ORGANISM: Homo sapiens
```

-continued

```
<400> SEQUENCE: 7

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 8
<211> LENGTH: 97
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp

<210> SEQ ID NO 9
<211> LENGTH: 97
<212> TYPE: PRT
<213> ORGANISM: Homo sapiens

<400> SEQUENCE: 9

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu
```

<210> SEQ ID NO 10
<211> LENGTH: 98
<212> TYPE: PRT
<213> ORGANISM: Homo sapiens

<400> SEQUENCE: 10

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys

<210> SEQ ID NO 11
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys

<210> SEQ ID NO 12
<211> LENGTH: 99
<212> TYPE: PRT
<213> ORGANISM: Homo sapiens

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro

<210> SEQ ID NO 13
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys Pro

<210> SEQ ID NO 14
<211> LENGTH: 100
<212> TYPE: PRT
<213> ORGANISM: Homo sapiens

<400> SEQUENCE: 14

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser
            100

<210> SEQ ID NO 15
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 15

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys Pro Ser
            100

<210> SEQ ID NO 16
<211> LENGTH: 101
<212> TYPE: PRT
<213> ORGANISM: Homo sapiens

<400> SEQUENCE: 16

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 17
<211> LENGTH: 166
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
```

```
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(126)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (133)..(152)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (160)..(179)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: misc_feature
<222> LOCATION: (1)..(186)
<223> OTHER INFORMATION: /note="see specification as filed for detailed
      description of substitutions and preferred embodiments"

<400> SEQUENCE: 17

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr
                165

<210> SEQ ID NO 18
<211> LENGTH: 167
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 18

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu
                165
```

```
<210> SEQ ID NO 19
<211> LENGTH: 168
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 19

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140
```

```
Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile
                165
```

<210> SEQ ID NO 20
<211> LENGTH: 169
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 20

```
Val Ser Asp Val Pro Arg Asp Leu Glu Val Val Ala Ala Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Leu Leu Ile Ser Trp Xaa Xaa Xaa Xaa Xaa Xaa Xaa Xaa Xaa
                35                  40                  45

Xaa Xaa Xaa Xaa Xaa Xaa Xaa Xaa Xaa Tyr Arg Ile Thr Tyr Xaa
            50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95
```

```
Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp
                165

<210> SEQ ID NO 21
<211> LENGTH: 169
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 21

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45
```

```
Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa
 65                  70                  75                  80

Xaa Xaa Xaa Phe Thr Val Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu
                165
```

<210> SEQ ID NO 22
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (14)..(33)
<223> OTHER INFORMATION: Any amino acid and this region may encompass 2-20, 2-15, 2-10, 2-8, 5-20, 5-15, 5-10, 5-8, 6-20, 6-15, 6-10, 6-8, 2-7, 5-7, or 6-7 residues, wherein some positions may be absent
<220> FEATURE:
<221> NAME/KEY: MOD_RES
<222> LOCATION: (39)..(58)
<223> OTHER INFORMATION: Any amino acid
<220> FEATURE:
<221> NAME/KEY: MOD_RES
<222> LOCATION: (64)..(83)
<223> OTHER INFORMATION: Any amino acid and this region may encompass 2-20, 2-15, 2-10, 2-8, 5-20, 5-15, 5-10, 5-8, 6-20, 6-15, 6-10, 6-8, 2-7, 5-7, or 6-7 residues, wherein some positions may be absent
<220> FEATURE:
<221> NAME/KEY: MOD_RES
<222> LOCATION: (87)..(106)
<223> OTHER INFORMATION: Any amino acid and this region may encompass 2-20, 2-15, 2-10, 2-8, 5-20, 5-15, 5-10, 5-8, 6-20, 6-15, 6-10, 6-8, 2-7, 5-7, or 6-7 residues, wherein some positions may be absent
<220> FEATURE:
<221> NAME/KEY: MOD_RES
<222> LOCATION: (113)..(132)
<223> OTHER INFORMATION: Any amino acid and this region may encompass 2-20, 2-15, 2-10, 2-8, 5-20, 5-15, 5-10, 5-8, 6-20, 6-15, 6-10, 6-8, 2-7, 5-7, or 6-7 residues, wherein some positions may be absent
<220> FEATURE:
<221> NAME/KEY: MOD_RES
<222> LOCATION: (140)..(159)
<223> OTHER INFORMATION: Any amino acid and this region may encompass 2-20, 2-15, 2-10, 2-8, 5-20, 5-15, 5-10, 5-8, 6-20, 6-15, 6-10, 6-8, 2-7, 5-7, or 6-7 residues, wherein some positions may be absent -continued

```
<400> SEQUENCE: 22

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys
                165                 170

<210> SEQ ID NO 23
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
```

```
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 23

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Tyr Arg Ile Thr Tyr Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys
                165                 170

<210> SEQ ID NO 24
<211> LENGTH: 171
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
```

<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 24

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro
                165                 170

<210> SEQ ID NO 25
<211> LENGTH: 171
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

```
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 25

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro
                165                 170

<210> SEQ ID NO 26
<211> LENGTH: 172
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 26

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

```
Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro Ser
                165                 170

<210> SEQ ID NO 27
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 27

Val Ser Asp Val Pro Arg Asp Leu Glu Val Val Ala Ala Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Leu Leu Ile Ser Trp Xaa Xaa Xaa Xaa Xaa Xaa Xaa Xaa Xaa
                35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95
```

```
Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser
                165                 170

<210> SEQ ID NO 28
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 28

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
        35                  40                  45
```

```
Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa
 65                  70                  75                  80

Xaa Xaa Xaa Phe Thr Val Xaa Xaa Xaa Xaa Xaa Xaa Xaa Xaa
                 85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro Ser Gln
                165                 170

<210> SEQ ID NO 29
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
```

-continued

```
<400> SEQUENCE: 29

Val Ser Asp Val Pro Arg Asp Leu Glu Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu
                100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa
        130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser Gln
                165                 170

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Met Gly Val Ser Asp Val Pro Arg Asp Leu
1               5                   10

<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Val Ser Asp Val Pro Arg Asp Leu
1               5

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 32

Met Gly Ser Asp Val Pro Arg Asp Leu
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 33

Met Gly Asp Val Pro Arg Asp Leu
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
```

```
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 34

Met Gly Val Pro Arg Asp Leu
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 35

Met Gly Pro Arg Asp Leu
1               5

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
```

<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 36

Met Gly Arg Asp Leu
1               5

<210> SEQ ID NO 37
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 37

Met Gly Asp Leu
1

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Met Ala Ser Thr Ser Gly
1               5

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 39

Glu Ile Glu Lys
1

<210> SEQ ID NO 40
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Glu Gly Ser Gly Cys
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Glu Ile Glu Lys Pro Cys Gln
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Glu Ile Glu Lys Pro Ser Gln
1               5

<210> SEQ ID NO 43
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Glu Ile Glu Lys Pro
1               5

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Glu Ile Glu Lys Pro Ser
1               5
```

```
<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Glu Ile Glu Lys Pro Cys
1               5

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 46

His His His His His His
1               5

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Glu Ile Asp Lys
1

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Glu Ile Asp Lys Pro Cys Gln
1               5

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Glu Ile Asp Lys Pro Ser Gln
1               5

<210> SEQ ID NO 50
<211> LENGTH: 91
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 50

Met Pro Ala Pro Thr Asp Leu Arg Phe Thr Asn Glu Thr Pro Ser Ser
1               5                   10                  15

Leu Leu Ile Ser Trp Thr Pro Pro Arg Val Gln Ile Thr Gly Tyr Ile
            20                  25                  30

Ile Arg Tyr Gly Pro Val Gly Ser Asp Gly Arg Val Lys Glu Phe Thr
            35                  40                  45

Val Pro Pro Ser Val Ser Ser Ala Thr Ile Thr Gly Leu Lys Pro Gly
        50                  55                  60

Thr Glu Tyr Thr Ile Ser Val Ile Ala Leu Lys Asp Asn Gln Glu Ser
65                  70                  75                  80

Glu Pro Leu Arg Gly Arg Val Thr Thr Gly Gly
                85                  90

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Thr Pro Ser Ser
1

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Thr Pro Pro Arg Val Gln Ile
1               5

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Val Gly Ser Asp Gly Arg
1               5

<210> SEQ ID NO 54
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 54

Pro Ser Val Ser
1

<210> SEQ ID NO 55
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Leu Lys Pro Gly
1               5

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Lys Asp Asn Gln Glu Ser Glu Pro
1               5

<210> SEQ ID NO 57
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
                20                  25                  30

Ile Thr Tyr Thr Pro Ser Asn Gly Pro Gly Glu Pro Lys Glu Leu Thr
            35                  40                  45

Val Pro Pro Ser Thr Ser Val Thr Ile Thr Gly Ile Thr Pro Gly
    50                  55                  60

Val Glu Tyr Val Val Ser Val Tyr Ala Leu Lys Asp Asn Gln Glu Ser
65                  70                  75                  80

Pro Pro Leu Val Gly Thr Cys Thr Thr
                85

<210> SEQ ID NO 58
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 58

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 59
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Thr Glu Asp Ser
1

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Thr Ala Pro Asp Ala Ala Phe
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Glu Lys Val Gly Glu
1               5

<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Ser Glu Arg
1
```

-continued

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Leu Lys Pro Gly
1               5

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Lys Gly Gly His Arg Ser Asn
1               5

<210> SEQ ID NO 65
<211> LENGTH: 330
<212> TYPE: PRT
<213> ORGANISM: Homo sapiens

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 66
<211> LENGTH: 227
<212> TYPE: PRT
<213> ORGANISM: Homo sapiens

<400> SEQUENCE: 66

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 67
<211> LENGTH: 208
<212> TYPE: PRT
<213> ORGANISM: Homo sapiens

<400> SEQUENCE: 67

```
Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205
```

<210> SEQ ID NO 68
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 69
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
            50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230
```

-continued

```
<210> SEQ ID NO 70
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 71
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
 65                  70                  75                  80

Tyr Gln Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 72
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Pro Arg Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 73
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 74
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 74

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 75
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 76
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 77
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Pro Lys Ser Ser Asp Lys Thr His Thr Ser Pro Pro Ser Pro Ala
1               5                   10                  15
Pro Glu Ala Glu Gly Ala Pro Ser Val Phe Leu Phe Pro Pro Lys Pro
                20                  25                  30
Lys Asp Thr Leu Met Ile Ser Arg Thr Pro Glu Val Thr Cys Val Val
            35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ser Ser Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Gly
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 78
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 78

```
Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 79
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Lys Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 80
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Leu Gly Lys
225                 230
```

<210> SEQ ID NO 81
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Ala Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 82
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 82

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
    210                 215                 220

Ser Leu Ser Leu Ser Pro Gly Lys
225                 230

<210> SEQ ID NO 83
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 84
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
            195                 200                 205
```

```
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 85
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 86
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 86

Glu Pro Lys Ser Ser Asp Lys Thr His Thr Cys Pro Pro Cys Pro Ala
1               5                   10                  15

Pro Glu Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 87
<211> LENGTH: 16
<212> TYPE: PRT
<213> ORGANISM: Homo sapiens

<400> SEQUENCE: 87

Asp Lys Thr His Thr Cys Pro Pro Cys Pro Ala Pro Glu Leu Leu Gly
1               5                   10                  15

<210> SEQ ID NO 88
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Glu Pro Lys Ser Ser Asp Lys Thr His Thr Cys Pro Pro Cys Pro Ala
1               5                   10                  15

Pro Glu Leu Leu Gly Gly Pro Ser
            20

```
<210> SEQ ID NO 89
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 90
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Glu Pro Lys Ser Ser Gly Ser Thr His Thr Cys Pro Pro Cys Pro Ala
1               5                   10                  15

Pro Glu Leu Leu Gly Gly Ser Ser
            20

<210> SEQ ID NO 91
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Lys Thr His Thr Cys Pro Pro Cys Pro Ala Pro Glu Leu Leu Gly
1               5                   10                  15

Gly Pro Ser

<210> SEQ ID NO 92
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asp Lys Thr His Thr Cys Pro Pro Cys Pro Ala Pro Glu Leu Leu Gly
1               5                   10                  15

Gly Ser Ser

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 93

Glu Pro Lys Ser Ser Asp Lys Thr His Thr Cys Pro Pro Cys Pro
1               5                   10                  15

<210> SEQ ID NO 94
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Met Gly Val Ser Asp Val Pro Arg Asp Leu Glu Val Val Ala Ala Thr
1               5                   10                  15

Pro Thr Ser Leu Leu Ile Ser Trp Val Pro Ser Asp Tyr Gly
            20                  25                  30

Tyr Tyr Arg Ile Thr Tyr Gly Glu Thr Gly Gly Asn Ser Pro Val Gln
                35                  40                  45

Glu Phe Thr Val Pro Ile Gly Lys Gly Thr Ala Thr Ile Ser Gly Leu
    50                  55                  60

Lys Pro Gly Val Asp Tyr Thr Ile Thr Val Tyr Ala Val Glu Phe Pro
65                  70                  75                  80

Trp Pro His Ala Gly Tyr Tyr His Arg Pro Ile Ser Ile Asn Tyr Arg
                85                  90                  95

Thr Glu Ile Glu Pro Lys Ser Ser Gly Ser Thr His Thr Cys Pro Pro
                100                 105                 110

Cys Pro Ala Pro Glu Leu Leu Gly Gly Ser Ser Val Phe Leu Phe Pro
            115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

-continued

```
<210> SEQ ID NO 95
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Met Ala Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro
225

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ser Gly Ser
1

<210> SEQ ID NO 97
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 97

Gly Ser Gly Ser Gly Ser
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Ser Gly Ser Gly Ser Gly Ser
1               5

<210> SEQ ID NO 99
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Ser Gly Ser Gly Ser Gly Ser Gly Ser
1               5                   10

<210> SEQ ID NO 100
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Ser Gly Ser Gly Ser Gly Ser Gly Ser Gly Ser
1               5                   10

<210> SEQ ID NO 101
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Ser Gly Ser Gly Ser Gly Ser Gly Ser Gly Ser Gly Ser
1               5                   10

<210> SEQ ID NO 102
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 102

Gly Ser Gly Ser Gly Ser Gly Ser Gly Ser Gly Ser Gly Ser Gly Ser
1               5                   10                  15

<210> SEQ ID NO 103
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Ser Gly Ser Gly Ser Gly Ser Gly Ser Gly Ser Gly Ser Gly Ser
1               5                   10                  15

Gly Ser

<210> SEQ ID NO 104
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Ser Gly Ser Gly Ser Gly Ser Gly Ser Gly Ser Gly Ser Gly Ser
1               5                   10                  15

Gly Ser Gly Ser
            20

<210> SEQ ID NO 105
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Gly Gly Gly Ser
1               5

<210> SEQ ID NO 106
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly Gly Gly Gly Ser
1               5                   10

<210> SEQ ID NO 107
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Gly Gly Ser Gly Gly Gly Gly Ser Gly Gly Gly Gly Ser Gly
1               5                   10                  15

Gly Gly Gly Ser
            20

<210> SEQ ID NO 109
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

TANGENTIAL FLOW FILTRATION BASED PROTEIN REFOLDING METHODS

CROSS-REFERENCE TO RELATED APPLICATIONS

This application is a division of U.S. patent application Ser. No. 14/766,849, filed Aug. 10, 2015, which is a 35 U.S.C. 371 national stage filing of International Application No. PCT/US2014/015658, filed Feb. 11, 2014, which claims priority to U.S. Provisional Application No. 61/763,670, filed on Feb. 12, 2013. The contents of the aforementioned applications are hereby incorporated by reference herein.

SEQUENCE LISTING

The instant application contains a Sequence Listing which has been submitted electronically in ASCII format and is hereby incorporated by reference in its entirety. Said ASCII copy, created on Dec. 5, 2018, is named MXI_568USDV_Sequence_Listing.txt and is 128,124 bytes in size.

BACKGROUND

The backbone of an antibody, known as the Fc region, is responsible for pharmacokinetic properties that may be desirable in the case of many therapeutic biologics (Jeffries, B. Biotechnol Prog. 2005; 21: 11-16). The size of the Fc region makes it resistant to renal filtration and binding to the Fc Neonatal Receptor (FcRn) allows it to escape endosomal degradation by a recycling mechanism. In addition to the Fc region that is present in monoclonal antibody therapeutic products, there are Fc fusion products being investigated and developed (Hakim et al. Mabs. 2009; 1:281-287). Fc fusions are the fusion of an Fc region to another protein, peptide, or Active Pharmaceutical Ingredient (API). The Fc fusion then has both the properties of the Fc region and the therapeutic properties of the API.

There are many cell lines that are capable of being used to manufacture therapeutic biologics (Jung et al. Curr Opin Biotechnol. 2011; 22:1-10). The mammalian Chinese Hamster Ovary (CHO), insect Sf9, yeast *S. cereviae*, and bacterial *E. coli* are some of the most common cell lines that are discussed for recombinant protein production. So far, yeast, CHO and *E. coli* have been used for manufacture of Fc containing therapeutic biologics, including a large number of monoclonal antibodies. Expression in *E. coli* offers three potential and significant advantages over expression in other cell lines: the cell line development time is much shorter; the bioreactor runs are up to 7-fold shorter, resulting in a lower capital investment; and there is no need to control aberrant glycosylation that can occur in yeast and mammalian cell cultures.

Expression of larger proteins, like Fc fusions, in *E. coli* can be a unique challenge. *E. coli* lack the chaperone proteins and other refolding machinery found in a eukaryotic expression system. The cytoplasm of *E. coli* is also a reducing environment, which is not favorable for the formation of disulfide bonds. The Fc region of human IgG1 antibodies contains six disulfide bonds. Two disulfide bonds the hinge region join two peptide chains to form the homodimeric molecule and there are two more disulfide bonds within each of the peptide chains. *E. coli* also have a mechanism to prevent unfolded proteins from interfering with normal cell processes. Unfolded protein is shunted and isolated in an insoluble aggregates, called Inclusion Bodies (IB), which can then be isolated in the insoluble fraction following cell lysis. Alternatively, when the rate of recombinant protein production is slowed to allow the protein to fold, a leader sequence may be added to direct soluble protein that is expressed to the periplasmic space. The periplasm is an oxidative environment favorable for the formation of disulfide bonds. However, the reported expression levels of recombinant protein in the periplasm remain low (Liu et al. Protein Expression Purif. 2008; 62:15-20).

In contrast, *E. coli* expression levels in IBs have been reported to be high. Expressing protein in IBs also has the advantages of resistance to protein degradation, and ease of isolation from the cells (Grune et al. Int J Biochem Cell Biol. 2004; 36:2519-2530). Since an IB is an insoluble aggregate, there may be a challenge in restoring the protein of interest to its biologically active conformation (Jungbauer et al. J Biotechnol. 2006; 587-596). Typically, a process is required to break apart and solubilize the IB. Then the protein must be renatured, or refolded, into the biologically active conformation while minimizing losses due to aggregation and precipitation. Current refolding processes may be specific to a given protein, requiring thorough optimization for each case. Many refolding processes require very low protein concentrations and consequently large volumes for the operation. This is difficult because it requires a larger amount of potentially expensive reagents. There is also a challenge in a manufacturing setting, where there is a physical limit to the container size that may be used to refold proteins. Finally, in the case of Fc fusions, the refolding process must correctly form the six disulfide bonds that exist in the native form of the protein.

SUMMARY

Provided herein are methods for refolding a denatured protein, comprising, e.g., (i) combining denatured protein (e.g., inclusion bodies (IBs)) with a solubilization buffer that comprises a denaturing agent, to obtain a first protein composition comprising solubilized denatured protein; (ii) diafiltering the first protein composition comprising solubilized denatured protein with 2-4 diavolumes of a refold buffer, to obtain a second protein composition comprising partially refolded protein; and (iii) incubating the second protein composition comprising partially refolded protein with a refold/oxidizing buffer to obtain a third protein composition comprising the protein in a refolded state. Also provided herein are methods for refolding a denatured protein, e.g., that is present in inclusion bodies (IBs), comprising, e.g., (i) suspending denatured protein (e.g., IBs) in a suspension solution, to obtain a composition comprising suspended denatured protein; (ii) combining the composition comprising suspended IBs with a solubilization buffer that comprises a denaturing agent, to obtain a first protein composition comprising solubilized denatured protein; (iii) diafiltering the first protein composition comprising solubilized denatured protein with 2-4 diavolumes of a refold buffer to obtain a second protein composition comprising partially refolded protein; and (iv) incubating the second protein composition comprising partially refolded protein with a refold/oxidizing buffer to obtain a third protein composition comprising the protein in a refolded state. Incubating the second protein composition comprising partially refolded protein with a refold/oxidizing buffer may comprise diafiltering the second protein composition with, e.g., 2-6 diavolumes, of a refold/oxidizing buffer. Diafiltering the first protein composition may be conducted at least in part with a tangential flow filtration (TFF) device. Diafiltering the second protein composition may be conducted at least in part with a tangential flow filtration (TFF) device. Diafiltering the first protein composition may be conducted at least in part with a TFF device and diafiltering the second protein composition may be conducted at least in part with a TFF device. The TFF may be operated with a transmembrane pressure (TMP) between 10 and 30 PSI. The diafiltering may be operated with a molecular weight cut off (MWCO) membrane of at least 5 kDa. The diafiltering may be operated with a MWCO membrane of between 5 kDa and 50 kDa. The diafiltering with refold buffer may take between 0.5 to 3 hours. The diafiltering with refold/oxidizing buffer may take between 0.5 to 3 hours. The refold buffer and the refold/oxidizing buffer may have a pH value between pH 8 and 11, e.g., a pH value between pH 9 and 11.

In the methods described herein, the denaturing agent may comprise guanidine, the refold/oxidizing buffer may comprise an oxidizing agent; the oxidizing agent may comprise glutathione; the refold buffer may comprise Arginine and/or the refold/oxidizing buffer may comprise Arginine.

In the methods described herein, the denatured protein may be suspended in a suspension solution at a ratio of weight (grams) of denatured protein: volume (ml) of suspension solution of 1:1-10, e.g., 1:1-5. The suspension solution may consist essentially of water. The solubilization buffer may comprise Tris and guanidine. The solubilization buffer may comprise a reducing agent. In certain embodiments, the solubilization buffer does not comprise a significant amount of reducing agent. The refold buffer may comprise Tris.

In the methods described herein, the composition comprising solubilized denatured protein may be diluted 1-10 fold with a dilution buffer prior to diafiltering. In certain embodiments, the composition comprising solubilized denatured protein is not diluted prior to diafiltering. The composition comprising solubilized denatured protein may be filtered prior to diafiltering. In certain embodiments, the composition comprising solubilized denatured protein is not filtered prior to diafiltering.

A method described herein may comprise: (i) combining denatured protein with a solubilization buffer that comprises a denaturing agent, to obtain a first protein composition comprising solubilized denatured protein; (ii) diafiltering the first protein composition comprising solubilized denatured protein with 2-4 diavolumes of a refold buffer to obtain a second protein composition comprising partially folded protein, wherein the refold buffer comprises Arginine and has a pH between pH 8-11; and (iii) diafiltering the second protein composition comprising partially folded protein with 2-6 diavolumes of a refold/oxidizing buffer to obtain a third protein composition comprising the protein in a refolded state, wherein the refold/oxidizing buffer comprises Arginine, an oxidizing agent and has a pH between pH 8-11. A method for refolding a denatured protein may comprise (i) suspending the denatured protein in a suspension solution to obtain a composition comprising suspended denatured protein; (ii) combining the composition comprising suspended denatured protein with a solubilization buffer that comprises a denaturing agent, to obtain a first protein composition comprising solubilized denatured protein; (iii) diafiltering the first protein composition comprising solubilized denatured protein with 2-4 diavolumes of a refold buffer to obtain a second protein composition comprising partially refolded protein, wherein the refold buffer comprises Arginine and has a pH between pH 8-11; and (iv) diafiltering the second protein composition comprising partially folded protein with 2-6 diavolumes of a refold/oxidizing buffer to obtain a third protein composition comprising the protein in a refolded state wherein the refold/oxidizing buffer comprises Arginine, an oxidizing agent and has a pH between pH 8-11. A method for refolding denatured protein in IBs, may comprise: (i) solubilizing IBs in a solubilization buffer that comprises a denaturing agent, to obtain a first protein composition comprising solubilized IBs; (ii) diafiltering the solubilized IBs with 2-4 diavolumes of a refold buffer to obtain a second protein composition comprising partially folded protein, wherein the refold buffer comprises Arginine and has a pH between pH 8-11; and (iii) diafiltering the second protein composition comprising partially folded protein with 2-6 diavolumes of a refold/oxidizing buffer to obtain a third protein composition comprising the protein in a refolded state wherein the refold/oxidizing buffer comprises Arginine, an oxidizing agent and has a pH between pH 8-11. In certain embodiments, the solubilizing buffer and/or the refold buffer does not comprise a reducing agent.

In certain embodiments, the third protein composition comprises 1-10 mg/ml of protein. In certain embodiments, the efficiency of recovery is at least about 70%. The protein that is renatured may comprise at least one disulfide bond, e.g., an inter-chain disulfide bond or an intra-chain disulfide bond. The protein may comprise an Fc region, which may comprise a hinge. The protein may comprise a binding domain that specifically binds to a target protein, e.g., an alternative scaffold binding domain, e.g., an alternative fibronectin based scaffold domain, such as a $^{10}$FN3 domain. A $^{10}$FN3 protein may be fused to an Fc region comprising a hinge, a CH2 and a CH3 domain.

BRIEF DESCRIPTION OF THE FIGURES

FIG. 1A shows a process wherein the denatured protein (e.g., IB, a pellet of denatured protein or protein not in a biologically active conformation) is solubilized in a denaturing buffer, diafiltered with a refold buffer, and has a refold/oxidizing buffer introduced. Each step forms a different protein composition.

FIGS. 3A-C show that $^{10}$Fn3/Fc protein after refold step 1 is mostly in the form of a monomer (panel A), whereas the $^{10}$Fn3/Fc protein after refold step 2 is mostly in the form of a dimer (panel B), confirming that the protein was refolded. Panels A and B show the $^{10}$Fn3/Fc protein after refold steps 1 and 2, respectively, (peaks labeled "refold step 1" and "refold step 2") compared to the same refolded protein ("standard"), as visualized by RP-HPLC. Panel C shows the $^{10}$Fn3/Fc protein after refold steps 1 and 2, respectively, as visualized by SDS PAGE. The arrow in panel C indicates the position of the dimer.

FIGS. 5A-C show that $^{10}$Fn3/Fc protein after refold step 1 is mostly in the form of a monomer (panel A), whereas the $^{10}$Fn3/Fc protein after refold step 2 is mostly in the form of a dimer (panel B), confirming that the protein was refolded. Panels A and B show the $^{10}$Fn3/Fc protein after refold steps 1 and 2, respectively, (peaks labeled "refold step 1" and "refold step 2") compared to the same refolded protein ("standard"), as visualized by RP-HPLC. Panel C shows the $^{10}$Fn3/Fc protein after refold steps 1 and 2, respectively, as visualized by SDS PAGE. The arrow in panel C indicates the position of the dimer.

FIGS. 9A-C show that $^{10}$Fn3/Fc protein after refold step 1 is mostly in the form of a monomer (panel A), whereas the $^{10}$Fn3/Fc protein after refold step 2 is mostly in the form of a dimer (panel B), confirming that the protein was refolded. Panels A and B show the $^{10}$Fn3/Fc protein after refold steps 1 and 2, respectively, (peaks labeled "refold step 1" and "refold step 2") compared to the same refolded protein ("standard"), as visualized by RP-HPLC. Panel C shows the $^{10}$Fn3/Fc protein after refold steps 1 and 2, respectively, as visualized by SDS PAGE. The arrow in panel C indicates the position of the dimer.

FIGS. 11A-C show that $^{10}$Fn3/Fc protein after refold step 1 is mostly in the form of a monomer (panel A), whereas the $^{10}$Fn3/Fc protein after refold step 2 is mostly in the form of a dimer (panel B), confirming that the protein was refolded. Panels A and B show the $^{10}$Fn3/Fc protein after refold steps 1 and 2, respectively, (peaks labeled "refold step 1" and "refold step 2") compared to the same refolded protein ("standard"), as visualized by RP-HPLC. Panel C shows the $^{10}$Fn3/Fc protein after refold steps 1 and 2, respectively, as visualized by SDS PAGE. The arrow in panel C indicates the position of the dimer.

DETAILED DESCRIPTION

Figure 1B:
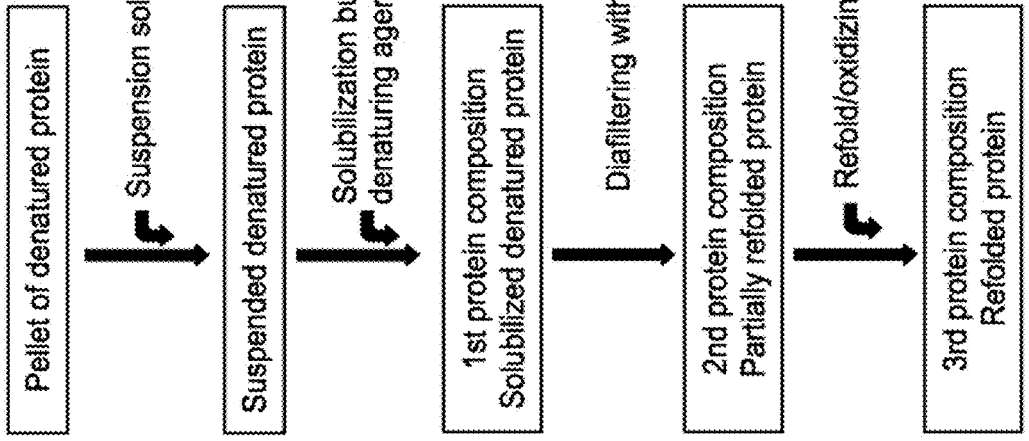
FIG. 1B shows a similar process wherein the denatured protein is first suspended in solution before introducing the denaturing buffer and proceeding with the rest of the process.

Provided herein are methods for refolding denatured proteins, such as proteins that are in the form of inclusion bodies (IBs). The methods are applicable to, e.g., proteins comprising at least one disulfide bond, such as proteins comprising an Fc region or domain (or portions thereof) of antibodies. A method may comprise solubilizing denatured protein with a chaotropic agent, and renaturing the protein using tangential flow filtration (TFF). Unlike commonly used methods for refolding proteins, e.g., from IBs, the methods described herein allow refolding of denatured proteins without the use of large volumes of buffer, with generally higher efficiency, and in generally shorter time frames than those of commonly used methods.

Definitions

By "polypeptide" is meant any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "region" of a $^{10}$Fn3 domain (or moiety) as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-101 of SEQ ID NO: 1) of the human $^{10}$Fn3 domain having SEQ ID NO: 1.

A "north pole loop" refers to any one of the BC, DE and FG loops of a human fibronectin type 3 tenth ($^{10}$Fn3) domain.

A "south pole loop" refers to any one of the AB, CD and EF loops of a human fibronectin type 3 tenth ($^{10}$Fn3) domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-101 of SEQ ID NO: 1).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software.

Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc., has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wild-type $^{10}$Fn3 (e.g., SEQ ID NO: 1), to alanine, or to a residue having a similarly sized or smaller side chain than the residue in question, leads to a measured increase of the equilibrium dissociation constant to the target (e.g., an increase in the kon).

"Moiety" refers to a portion of a protein. For example, a fusion protein may comprise several moieties. In one embodiment, a fusion protein comprises a fibronectin based scaffold moiety and an Fc moiety. An Fc moiety may comprise one or more of a CH2 domain, CH3 domain and a hinge.

A "denatured protein" refers to a protein that is not properly folded (i.e., does not have the proper spatial conformation or three dimensional structure). "Denaturation" refers to a process in which the native conformation of the protein is changed but the primary structure (amino acid chain, peptide links) of the protein remains unchanged. To be able to perform its biological function, a protein folds into a specific spatial conformation, by the action of non-covalent interactions such as ionic interactions, Van Der Waals forces, hydrogen bonding, and hydrophobic packing. A protein that is denatured (i.e., not properly folded) may be a protein that does not have a proper secondary, tertiary or quaternary structure. The secondary structure of a protein or polypeptide refers to highly regular local sub-structures, such as the alpha helix and the beta strand or beta sheets, of a protein. The tertiary structure of a protein or a polypeptide refers to the three-dimensional structure of a single protein molecule, in which the folding of the alpha-helices and beta-sheets into a compact globule is driven by the non-specific hydrophobic interactions (the burial of hydrophobic residues from water), salt bridges, hydrogen bonds, and the tight packing of side chains and disulfide bonds. The quaternary structure of a protein is the three-dimensional structure of subunits of a multi-subunit protein. The subunits of a protein are held together by the same bonds as those that maintain a tertiary structure of a protein. Disulfide bonds contribute to the tertiary and quaternary structure of a protein, polypeptide or polypeptide complex. A denatured protein may be a protein that contains cysteines, but in which the disulfide bonds are not present or are improperly formed. Denatured proteins are generally insoluble and precipitate out of a solution. The presence of one or more disulfide bonds in a protein generally makes its renaturation from a denatured state more challenging. Protein structure can be visualized or determined with various tools, e.g., X-ray crystallography, Nuclear Magnetic Resonance (NMR), circular dichroism and cryo-electron microscopy.

Methods for Refolding Denatured Proteins

When proteins are expressed in certain expression systems, they are produced in a denatured form and must be renatured, i.e., their secondary, tertiary and/or quaternary structure must be reformed. For example, proteins expressed at high levels in *E. coli* are shunted into inclusion bodies (IBs). IBs are essentially made of denatured proteins. The methods described herein may be used to renature unfolded or improperly folded proteins present in IBs. In certain embodiments, the methods are used at least in part to reform disulfide bonds, e.g., inter-chain or intra-chain disulfide bonds.

A method may comprise a step during which denatured protein is solubilized; a step during which the denatured protein is partially renatured, e.g., forms at least a partially-folded monomer; and a step during which a reduction-oxidation system is introduced to favor the formation of disulfide bonds, e.g., for forming disulfide linked dimers. The second step or both the second and the third steps may be performed with a buffer exchanging system, e.g., tangential flow filtration (TFF).

A method for refolding a denatured protein may comprise: (i) combining a denatured protein (e.g., IBs) with a solubilization buffer that comprises a denaturing agent, to obtain a first protein composition comprising solubilized denatured protein; (ii) diafiltering the first protein composition comprising solubilized denatured protein with refold buffer, to obtain a second protein composition comprising partially folded protein; and (iii) combining the second protein composition, e.g., by diafiltering the second protein composition, with refold/oxidizing buffer to obtain a third protein composition comprising the protein in a refolded state.

Figure 1A:
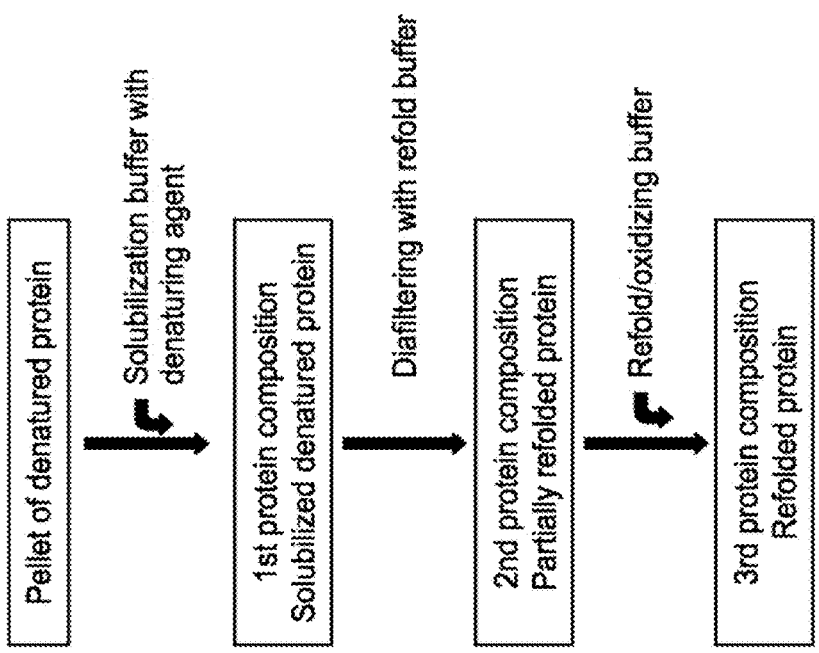
FIGS. 1A and B show flow diagrams of exemplary processes to refold denatured protein, e.g., produced as inclusion bodies (IBs) isolated from *E. coli*.

The steps of exemplary methods are set forth in FIG. 1. Panel A of FIG. 1 shows a method comprising: (i) combining a pellet of denatured protein with solubilization buffer comprising a denaturing agent to obtain a first protein composition comprising solubilized denatured protein; (ii) diafiltering the first protein composition with refold buffer to obtain a second protein composition; and (iii) combining, e.g., by diafiltering, the second protein composition with refold/oxidizing buffer to obtain a third protein composition comprising refolded protein. Panel B of FIG. 1 shows in method comprising: (i) combining a pellet of denatured protein with a suspension solution to obtain suspended denatured protein; (ii) combining suspended denatured protein with solubilization buffer comprising a denaturing agent to obtain a first protein composition comprising solubilized denatured protein; (iii) combining, e.g., by diafiltering, the first protein composition with refold buffer to obtain a second protein composition; and (iv) diafiltering the second protein composition with refold/oxidizing buffer to obtain a third protein composition comprising refolded protein.

In certain embodiments, the methods described herein do not use a significant amount of a reducing agent. A reducing agent is an agent that breaks disulfide bonds by reducing one or the two cysteines of the disulfide bond or maintains cysteines in a reduced state (i.e., maintains free sulfhydryl groups so that the intra- or intermolecular disulfide bonds are chemically disrupted). A "significant amount" of a reducing agent is an amount that is sufficient for reducing at least some disulfide bonds in a protein solution or for maintaining at least some cysteines in a protein solution in a reduced state.

Exemplary reducing agents include the following: beta-mercaptoethanol (BME), dithiothreitol (DTT), dithioerythritol (DTE), tris(2-carboxyethyl)phosphine (TCEP), cysteine, cysteamine, thioglycolate, glutathione and sodium borohydride. In certain embodiments, no reducing agent is added to, or present in, one or more of the following solutions used in the methods described herein: the suspension solution, such as an IB suspension solution; the solubilization buffer; and/or the refold buffer. In certain embodiments, no reducing agent is used or present in any step in the methods described herein. In certain embodiments, the concentration of a reducing agent in any step of the methods described herein is less than 10 mM, 1 mM, 0.1 mM, $10^{-2}$ mM, $10^{-3}$ mM, $10^{-4}$ mM, $10^{-5}$ mM, or $10^{-6}$ mM.

A method for refolding a protein that is present in IBs may include washing the IBs prior to suspending them in a suspension solution. Washing IBs may be performed with, e.g., Tris/HCL buffer, phosphate buffer, acetate buffer, citrate buffer or water, or a combination of two or more of these, with or without a detergent, e.g., Triton-X 100.

Suspension of Denatured Protein

The methods provided herein may comprise combining denatured protein with a solubilization buffer. In certain embodiments, a denatured protein, such as in the form of a pellet, is combined with solubilization buffer (comprising a denaturing agent). In certain embodiments, denatured protein, such as in the form of a pellet is suspended in a suspension solution prior to being combined with a solubilization buffer. Resuspending denatured protein in a suspension solution before adding a solubilization buffer may enhance the renaturation process by more properly resuspending the denatured protein prior to adding the denaturing agent.

Denatured protein, e.g., protein in IBs, which denatured protein may be, e.g., in the form of a pellet (such as a frozen pellet) may be suspended in a suspension solution (or buffer). The denatured protein may be incubated with suspension solution under conditions sufficient to substantially suspend the denatured protein. Incubation may take place under conditions of concentration, incubation time, and incubation temperature to allow suspension of the desired amount or most or substantially all the denatured protein (e.g., at least 70%, 80%, 90%, 95%, 97%, 98% or 99%).

In certain embodiments, the suspension solution is water. Water may be, e.g., tap water, distilled, double distilled, deionized water, reverse osmosed water, or reversed osmosed/deionized (RODI) water. In certain embodiments, a suspension solution comprises low concentrations of a buffer, e.g., TRIS/HCL, e.g., less than about 10 mM, 1 mM, 0.1 mM or less TRIS. A suspension solution may have a pH of 6-10, 6-9, 6-8, 6.5 to 7.5.

In certain embodiments, a pellet of denatured protein is contacted with a suspension solution at a ratio of weight (grams) of denatured protein (e.g., IB): volume (ml) of suspension solution (e.g., IB suspension solution) of 1:1-10; 1:1-9; 1:1-8; 1:1-7; 1:1-6; 1:1-5; 1:1-4; 1:1-3; 1:1-2; 1:1-1:2; 1:3; 1:4; 1:5; 1:6; 1:7; 1:8, 1:9 or 1:10. In certain embodiments, a pellet of denatured protein is contacted with a suspension solution at a ratio of weight (grams) of denatured protein (e.g., IB): volume of suspension solution (e.g., IB suspension solution) of 1:1-3. A weight to volume ratio of "1:3" in this context refers to a ratio of 1 gram of denatured protein to 3 ml of suspension solution. A weight to volume ratio of "1:1-3" in this context refers to a ratio of 1 gram of denatured protein to 1-3 ml (e.g., 1 ml, 2 ml or 3 ml and any values in between) of suspension solution. A weight to volume ratio may also be defined in kgs:liters. The combination of the denatured proteins and the suspension solution is referred to as the "suspension reaction."

The suspension reaction may be conducted at a temperature, e.g., ranging from 2° C. to 40° C.; 4° C. to 37° C.; 25° C. to 37° C.; room temperature; or 4° C. to 25° C. In an exemplary embodiment, a pellet of denatured protein, e.g., an IB pellet, is suspended in water at room temperature (e.g., 25° C.) at a ratio of weight (grams) of denatured protein pellet: volume (ml) of suspension solution of 1:1-3, such as 1:1, 1:2 or 1:3.

A suspension reaction may be incubated and optionally stirred until most or essentially all denatured protein has been resuspended, and optionally a fine suspension is obtained. The proportion of denatured proteins that are suspended in the suspension solution may be determined optically. In certain embodiments, the denatured protein is incubated and optionally stirred, e.g., for less than 1 minute, in the suspension buffer. In certain embodiments, the denatured protein is incubated and optionally stirred, e.g., for 1-10 minutes; 1-5 minutes or 1-3 minutes in the suspension solution. Longer incubation times, especially at lower temperatures may also be used.

In certain embodiments, a pellet of denatured protein is suspended in water at a ratio of weight (grams) of denatured protein pellet: volume (ml) of suspension solution of 1:1-3, e.g., 1:2, at room temperature and incubated at room temperature for 1-3 minutes, to thereby obtain a composition comprising a suspension of denatured proteins. In an exemplary embodiment, a pellet of IBs is suspended in water at a ratio of weight (grams) of denatured protein pellet: volume (ml) suspension solution of 1:1-3, e.g., 1:2, at room temperature and incubated at room temperature for 1-3 minutes, to thereby obtain a composition comprising an IB suspension.

In certain embodiments, the suspension solution or suspension reaction does not comprise a significant amount of reducing agent, as further described herein.

Solubilization of denatured protein Denatured protein is solubilized by combining it with a solubilization buffer that comprises a denaturing agent. As set forth above, the denatured protein may be in the form of a pellet or in the form of a suspension when it is combined with solubilization buffer.

Denatured protein, e.g., IBs, may be combined with a solubilization buffert to obtain a composition comprising solubilized denatured protein, e.g., solubilized IBs. Denatured protein may be incubated with solubilization buffer under conditions sufficient to substantially solubilize the protein. Incubation may take place under conditions of concentration, incubation time, and incubation temperature to allow solubilization of the desired amount or most or substantially all the protein (e.g., at least 70%, 80%, 90%, 95%, 97%, 98% or 99%).

In certain embodiments, solubilization buffer comprises one or more agents for solubilizing proteins, such as denaturing (or chaotropic) agents. Examples of denaturing agents include: guanidine (or guanidium), guanidium hydrochloride, guanidium chloride, guanidium thiocyanate, urea, thiourea, lithium perchlorate, magnesium chloride, phenol, betain, sarcosine, carbamoyl sarcosine, taurine, dimethylsulfoxide (DMSO); alcohols such as propanol, butanol and ethanol; detergents, such as sodium dodecyl sulfate (SDS), N-lauroyl sarcosine, Zwittergents, non-detergent sulfobetains (NDSB), TRITON™ X-100, NONIDET™ P-40, the TWEEN™ series and BRIJ™ series; hydroxides such as sodium potassium hydroxide, and combinations thereof. The denaturing agent may be present at a concentration at which, after combination with the denatured protein results in a composition of protein and solubilization buffer and a denaturing concentration of denaturing agent. Certain concentrations of denaturing agents do not denature proteins, and these concentrations are referred to as "non-denaturing concentrations." For example, 6 M guanidium is a denaturing concentration of guanidium, whereas 1M guanidium is not a denaturing concentration of guanidium. Similarly, urea concentrations of 1-2 M are not considered to be denaturing concentrations of urea.

In certain embodiments, the solubilization buffer comprises guanidine (or a salt or derivative thereof) at 2 M to 8 M, 2 M to 7 M or 6 M. In certain embodiments, the solubilization buffer comprises urea or a salt or derivative thereof at 1 to 5 M, 1 to 3 M or 2 to 3 M.

In certain embodiments, a solubilization buffer comprises a buffering agent suitable for maintaining the pH of the solubilization buffer or that of the composition comprising the solubilization buffer and denatured protein ("solubilization reaction") in a range of pH 7 to 11; 7 to 10; 7 to 9; 8 to 11; 8 to 10. In certain embodiment the pH is 8 and in other embodiments, it is 10. Suitable buffers include TRIS (Tris [hydroxymethyl]aminomethane), HEPPS (N-[2-Hydroxyethyl]piperazine-N'-[3-propane-sulfoni c acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In certain embodiments, the solubilization buffer comprises a buffer, e.g., TRIS, at a concentration of 1 mM to 1 M; 1 mM to 100 mM; 10 mM to 100 nM; 10 mM to 50 mM; 50 mM to 100 mM; 30 mM to 70 mM; or 40 mM to 60 mM. In certain embodiments, the solubilization buffer comprises a buffer, e.g., TRIS, at a concentration of about 50 mM. In certain embodiments, the solubilization buffer comprises TRIS, e.g., at 40-60 mM, and has a pH in the range of pH 7 to 11.

A solubilization buffer may also comprise an agent preventing protein aggregation, e.g., Arginine (or another positively charged amino acid), e.g., L-arginine/HCl (which is encompassed by the term "Arginine"). Arginine may be present at concentrations in the range of 50 mM to 500 mM; 100 mM to 500 mM; 200 mM to 500 mM; 300 mM to 500 mM; 350 mM to 450 mM. In certain embodiments, the solubilization buffer includes Arginine at a concentration of 300 mM to 400 mM.

The solubilization buffer may comprise TRIS and Arginine and have a pH in the range of 7 to 11. In certain embodiments, the solubilization buffer comprises TRIS at a concentration in the range of 10 mM to 100 mM; Arginine; and have a pH in the range of pH 7 to 11. The solubilization buffer may comprise TRIS and Arginine, wherein Arginine is at a concentration in the range of 300 mM to 500 mM; and has a pH in the range of 7 to 11. The solubilization buffer may comprise TRIS at a concentration in the range of 10 mM to 100 mM; Arginine at a concentration in the range of 300 mM to 500 mM; and have a pH in the range of 7 to 11. In certain embodiments, the solubilization buffer comprises TRIS at a concentration in the range of 30 mM to 70 mM; Arginine at a concentration in the range of 300 mM to 500 mM; and has a pH in the range of pH 7 to 11. In certain embodiments, the solubilization buffer comprises TRIS at a concentration of about 50 mM, Arginine at a concentration of about 400 mM, and has a pH of about 8 or 10.

In certain embodiments, the solubilization buffer comprises a reducing agent, such as TCEP. For example, a solubilization buffer may comprise TCEP at a concentration of 1 mM to 10 mM, e.g., 2 mM. In other embodiments, the solubilization buffer does not comprise a reducing agent, or at least it does not contain a significant amount of reducing agent. For example, a solubilization buffer may contain less than 10 mM, 5 mM or 1 mM of reducing agent, e.g., TCEP.

In certain embodiments, the denatured protein to be solubilized is in the form of a pellet, e.g., a pellet of IBs (e.g., washed IBs). An insoluble protein pellet may be combined with solubilization buffer at a ratio of weight (grams) of insoluble protein pellet (e.g., IBs): volume (ml) of solubilization buffer of 1:5-50; 1:10-50; 1:10-30; 1:15-25. Exemplary ratios include 1:10, 1:20 and 1:30. For example, for 1 gram of denatured protein (e.g., that was suspended in suspension solution), 5 to 50 ml; 10 to 50 ml; 10 to 30 ml or 15 to 25 ml of solubilization buffer may be added. In other embodiments, for 1 kg of denatured protein, 5-50 liters; 10-50 liters; 10 to 30 liters or 15 to 25 liters of solubilization buffer may be added.

In certain embodiments, the denatured protein to be solubilized is in the form of a suspension, e.g., an IB suspension. A suspension of insoluble IBs may be combined with solubilization buffer at a ratio of weight (grams) or volume (mls) of denatured protein (e.g., suspended IBs): volume (ml) of solubilization buffer of 1:5-50; 1:10-50; 1:10-30; 1:15-25. Exemplary ratios include 1:10, 1:20 and 1:30. When the denatured protein is in the form of a suspension, the solubilization buffer may comprise higher concentrations of ingredients, e.g., denaturing agent, relative to that used when the denatured protein is in the form of a pellet, so as to obtain a final concentration of ingredients that is in the range of that of the solubilization buffer described herein. Thus, for example, it may be desirable to combine a suspension of denatured protein with a solubilization buffer comprising 8 M guanidine, instead of 6 M guanidine that might be used with denatured protein in the form of a pellet.

The solubilization reaction (i.e., the combined composition of denatured protein and solubilization buffer) may be conducted at a temperature, e.g., ranging from 2° C. to 40° C.; 4° C. to 37° C.; 25° C. to 37° C.; room temperature; or 4° C. to 25° C. In certain embodiments, the solubilization reaction is conducted at room temperature (e.g., 25° C.) at a ratio of weight (grams) of denatured protein (e.g., suspended IBs): volume (ml) of solubilization buffer of 1:5-50; 1:10-50; 1:10-30; 1:15-25.

The composition comprising the denatured protein and the solubilization buffer (the "solubilization reaction") may be incubated, and optionally stirred, for a time sufficient to solubilize essentially all (e.g., at least 70%, 80%, 90%, 95%, 97%, 98% or 99%) of the protein, e.g., prior to the next step. The solubilization reaction may be incubated for less than 1 minute; 1 to 60 minutes; 1 to 30 minutes; 1 to 20 minutes; 1 to 10 minutes; 1 to 5 minutes; 1 to 3 minutes; 1 to 2 minutes; 2 to 5 minutes or 2 to 3 minutes, e.g., prior to adding the refold buffer. The solubilization reaction is preferably performed for a time frame sufficient for most proteins to be solubilized. That most or essentially all of the proteins have been solubilized in the solubilization buffer can be determined optically. The solution may be off-white, yellowish, or brownish in color and appear mostly transparent.

In certain embodiments, denatured proteins, e.g., IBs, are combined, and optionally mixed, with a solubilization buffer comprising TRIS at a concentration in the range of 30 mM to 70 mM; Arginine at a concentration in the range of 300 mM to 500 mM; and having a pH in the range of 7 to 11 at a ratio of weight (grams) of denatured protein (e.g., suspended IBs): volume (ml) of solubilization buffer of 1:5-50; 1:10-50; 1:10-30; 1:15-25, at room temperature; and wherein incubation is conducted for 2 to 5 minutes prior to, e.g., diluting and/or filtering the composition, to thereby obtain a composition comprising solubilized denatured proteins, e.g., solubilized IBs.

After incubation of the insoluble protein with solubilization buffer, the protein composition obtained (referred to herein as "solubilized denatured protein composition") may be diluted 1-10 fold, 2-9 fold, 3 to 7 fold, 4 to 6 fold, e.g., with a buffer. In certain embodiments, the protein composition is diluted 4-5 fold with a buffer ("dilution buffer"). The dilution buffer may comprise a denaturing agent, such as the same denaturing agent that was present in the solubilization buffer. The dilution buffer may comprise a concentration of denaturing agent that is lower than that in the solubilization buffer, such as to reduce the concentration of denaturing agent by the dilution. For example, the concentration of denaturing agent may be reduced by 10-50%, 20-50%, 30-50%, 40-50%, 10-40%, 10-30%, 20-40% or 20-30%. For example, if the solubilization buffer comprises 6 M guanidine, the dilution buffer may comprise the same or a lower concentration of guanidine, such as 2-5 M, 2.5 to 4.5 M or 3 to 4 M guanidine. In certain embodiments, the dilution buffer comprises 3.5M guanidine. The concentration of guanidine in the dilution buffer may be such that the final concentration of guanindine in the diluted protein composition is 3-5 M, e.g., 4 M.

In certain embodiments, the solubilized denatured protein composition (whether diluted or not), is subject to one or more purification steps prior to the next step, e.g., loading into the TFF reservoir. For example, a solubilized denatured protein composition may be filtered, e.g., with a 0.1 to 10 m filter, 0.1 to 8 m filter, 0.1 to 6 m filter, 0.1 to m filter, 0.1 to 0.3 m filter. In certain embodiments, the filter is a 0.2 m filter. Refolding denatured protein using TFF with refold buffer Refolding may take place under conditions appropriate to allow refolding of the desired amount or most or substantially all the protein (e.g., at least 70%, 80%, 90%, 95%, 97%, 98% or 99%).

For refolding solubilized denatured protein, a method may comprise using a buffer exchanging system, such as tangential flow filtration (TFF). A method may comprise two stages: a first stage (first refolding step) during which TFF is performed with refold buffer, which may transition resolubilized proteins to a reduced, partially-folded monomer; and a second stage (or second refolding step) during which the protein of the first stage is combined with refold/oxidizing buffer, to allow the formation of disulfide bonds, e.g., in a disulfide-linked homodimer. The second stage may be performed using TFF with refold/oxidizing buffer.

A method may comprise a first refolding step comprising diafiltering a composition comprising solubilized denatured protein (diluted or not; filtered or not) with a refold buffer for a time and under conditions appropriate to obtain a first protein composition comprising partially refolded or renatured protein and wherein the protein composition is essentially devoid of a denaturing concentration of denaturing agent, e.g., the denaturing agent that was present in the solubilizing buffer.

Figure 2:
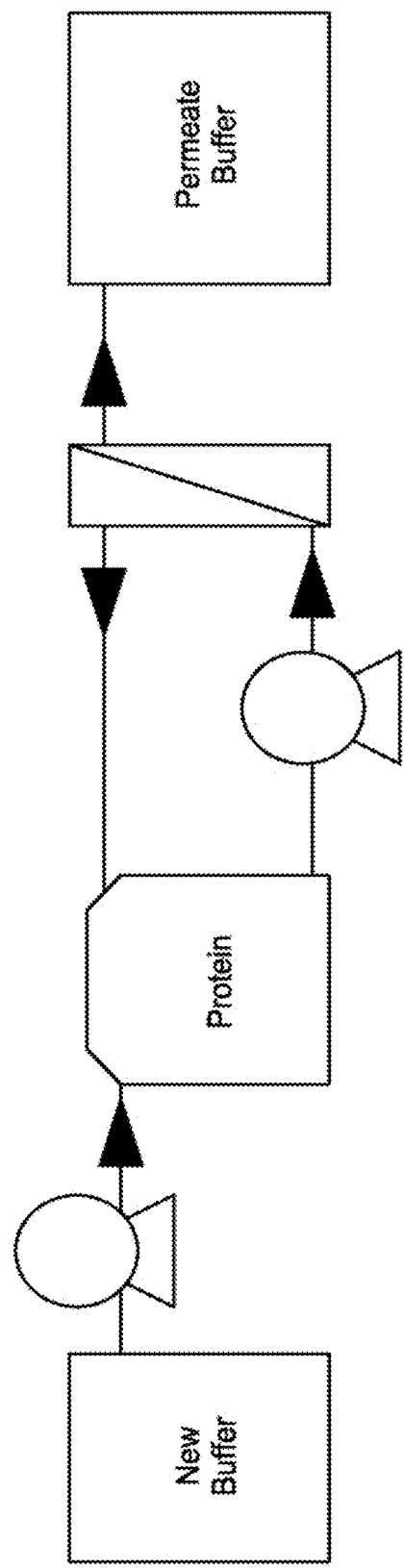
FIG. 2 shows a diagram of an exemplary set-up and flow path of a Tangential Flow Filtration (TFF) system used for diafiltration. Arrows indicate the direction of flow. In the middle, a reservoir contains a protein solution that is pumped across a TFF membrane. Components of the solution that are smaller than the nominal molecular weight cut off (NMWCO) of the membrane may pass through and be collected as permeate. Components of the solution larger than the NMWCO are retained, along with a portion of the smaller components, back into the protein reservoir. The membrane NMWCO is sized so that all of the protein is retained while on each pass, a portion of the buffer components are passing through to the permeate. To maintain constant or near constant protein concentration in the protein reservoir, a new buffer with different components is pumped into the protein reservoir at approximately the same rate as the permeate is being excluded. Each time permeate buffer is collected with a volume equal to the protein solution, it is said to be equal to one diavolume. As the TFF is run for more diavolumes, the buffer components of the protein solution become more similar to the new buffer than the starting buffer.

Diafiltering may be conducted using a tangential flow filtration (TFF) device, as shown, e.g., in FIG. 2. Briefly, a protein solution, e.g., comprising solubilized denatured protein, is loaded into a TFF reservoir (labeled "protein" on FIG. 2). The protein solution is passed tangentially across a membrane, permeate buffer goes through the membrane, but the protein is retained (i.e., does not cross the membrane) and is returned to the reservoir. New buffer is pumped into the reservoir. Each volume of buffer that is added to the reservoir is referred to as a "diavolume." The rates of flow of buffer and protein solution are referred to as the feed flow rate (rate at which buffer is added), the retentate flow rate (rate at which the protein concentration moves along the membrane) and the filtrate flow rate (rate at which filtrate goes through the membrane). The composition in the reservoir may be set up to allow gentle mixing, such that there is little or no visible separation of the buffers (e.g. guanidine containing resolubilization buffer and buffer without guanidine). In certain embodiments, the volume of the protein reservoir is kept essentially constant. In certain embodiments, the volume in the protein reservoir varies over time. For example, the volume may be reduced over time to simultaneously concentrate the protein solution.

Generally, the TFF device is operated with a molecular weight cut off (MWCO) membrane that is lower than the molecular weight of the denatured protein, e.g., a MWCO that is 1 kDa to 5 kDa, 1 kDa to 10 kDa, 1 kDa to 15 kDa, 1 kDa to 20 kDa, 1 kDa to 30 kDa, 5 kDa to 10 kDa, 5 kDa to 10 kDa, 5 kDa to 15 kDa, 5 kDa to 20 kDa, 5 kDa to 30 kDa, 10 kDa to 15 kDa, 10 kDa to 20 kDa, 10 kDa to 30 kDa, 15 kDa to 20 kDa, 15 kDa to 30 kDa, or 20 kDa to 30 kDa lower than the molecular weight of the denatured protein. In certain embodiments, the TFF device comprises a membrane having a MWCO of 1 kDa, 5 kDa, 10 kDa, 15 kDa, 20 kDa, or 30 kDa or a MWCO from 1 kDa to 5 kDa, 1 kDa to 10 kDa, 1 kDa to 15 kDa, 1 kDa to 20 kDa, 1 kDa to 30 kDa, 5 kDa to 10 kDa, 5 kDa to 15 kDa, 5 kDa to 20 kDa, 5 kDa to 30 kDa, 10 kDa to 15 kDa, 10 kDa to 20 kDa, 10 kDa to 30 kDa, 15 kDa to 20 kDa, 15 kDa to 30 kDa or 20 kDa to 30 kDa. In certain embodiments, the TFF device comprises a membrane having a MWCO of 5 kDa. A membrane having a MWCO of 5 kDa may be used, e.g., for proteins comprising an Fc, such as fusion proteins comprising a $^{10}$Fn3 domain linked to an Fc (e.g., an Fc comprising a hinge, CH2 and CH3 domains).

The membrane may be a membrane selected from one of several formats, such as flat plate, spiral wound or hollow fiber. In one embodiment, the membrane is a flat plate.

In certain embodiments, a TFF device is operated with a transmembrane pressure (TMP) that results in a rate of flow that is sufficient for partially refolding the protein and for doing so within a reasonable time frame. The TMP used may depend on the membrane used, and in particular, on the MWCO of the membrane. In certain embodiment, the TMP is between 5 and 50 PSI, 5 and 40 PSI, 5 and 30 PSI, 10 and 50 PSI, 10 and 40 PSI, 10 and 30 PSI, 15 and 50 PSI, 15 and 40 PSI, 15 and 30, 15 and 20 PSI, 20 and 50 PSI, 20 and 40 PSI, 20 and 30 PSI, or between 25 and 50 PSI.

Diafiltering with refold buffer may be conducted at a temperature, e.g., ranging from 2° C. to 40° C.; 4° C. to 37° C.; 25° C. to 37° C.; room temperature; or 4° C. to 25° C.

Diafiltering with the refold buffer may be conducted with a number of diavolumes (volume equivalents) of refold buffer and for at time sufficient to reduce the concentration of chaotropic agent (e.g., the chaotropic agent that was present in the solubilizing buffer) to a level that is essentially no longer denaturing. Denaturing concentrations vary with given denaturing agents. For example, in situations in which the solubilizing buffer contained guanidine as the denaturing agent, the number of diavolumes should be sufficient to reduce the concentration of guanidine to less than 2 M, 1 M, 0.5 M, 100 mM, 50 mM, 10 mM, 5 mM or 1 mM. In certain embodiments, compositions comprising solubilized denatured protein may be diafiltered with 1-10 diavolumes of refold buffer. In certain embodiments, a protein composition is diafiltered with 1-9, 1-8, 1-7, 1-6, 1-5, 1-4, 1-3 or 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6 or 4-5 diavolumes of refold buffer. In certain embodiments, a protein composition is diafiltered with 2-5, 2-4 or 3 diavolumes of refold buffer.

Diafiltering with the refold buffer may be conducted for a time sufficient to remove most of the denaturing agent that was present in the solubilizing buffer or at least reduce to non-denaturing concentrations. In certain embodiments, diafiltering with refold buffer may take from 0.3 hours to 5 hours, 0.3 hours to 4 hours, 0.3 hours to 3 hours, 0.5 hours to 5 hours, 0.5 hours to 4 hours, or 0.5 hours to 3 hours.

In certain embodiments, a refold buffer comprises a buffering agent suitable for maintaining the pH of the refold buffer and/or that of the composition comprising the refold buffer and denatured protein ("refold reaction") in a range of pH 9 to 11. The pH of the refold buffer and/or the refold reaction may also be within the following ranges of pH: 9.5 to 11; 9 to 10.5; 9.5 to 10.5; 9.8 to 10.2, and about 10.

A refold buffer may comprise Arginine (or another amino acid, such as Cysteine), e.g., L-arginine/HCl (which is encompassed by the term "Arginine"). A refold buffer may comprise Arginine at a concentration that is sufficient for buffering the refold buffer at the desired pH, e.g., a pH in the range of pH 9 to 11; pH: 9.5 to 11; 9 to 10.5; 9.5 to 10.5; 9.8 to 10.2, and about 10. Arginine may be present at concentrations in the range of 50 mM to 500 mM; 100 mM to 500 mM; 200 mM to 500 mM; 300 mM to 500 mM; 350 mM to 450 mM. In certain embodiments, the refold buffer includes Arginine at a concentration of 300 mM to 400 mM. In certain embodiments, a refold buffer comprises Arginine at 50 mM to 500 mM and has a pH in the range of 9 to 11. In certain embodiments, a refold buffer comprises Arginine at 200 mM to 500 mM and has a pH in the range of 9.5 to 10.5.

As Arginine buffers the pH of a solution around pH 10, it is not necessary to include another buffer in the refold buffer. However, in certain embodiments, one may include one or more of the following buffers: TRIS (Tris[hydroxymethyl]aminomethane), HEPES (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In certain embodiments, the refold buffer comprises a buffer, e.g., TRIS, at a concentration of 1 mM to 1 M; 1 mM to 100 mM; 10 mM to 100 nM; 10 mM to 50 mM; 50 mM to 100 mM; 30 mM to 70 mM; or 40 mM to 60 mM.

In certain embodiments, the refold buffer comprises a buffer, e.g., TRIS, at a concentration of about 50 mM. In certain embodiments, the refold buffer comprises TRIS, e.g., at 40-60 mM, and has a pH in the range of pH 9 to 11.

Refold buffer may comprise TRIS and Arginine and have a pH in the range of pH 9 to 11. In certain embodiments, the refold buffer comprises TRIS at a concentration in the range of 10 mM to 100 mM; Arginine; and have a pH in the range of pH 9 to 11. The refold buffer may comprise TRIS and Arginine, wherein Arginine is at a concentration in the range of 300 mM to 500 mM; and have a pH in the range of pH 9 to 11. The refold buffer may comprise TRIS at a concentration in the range of 10 mM to 100 mM; Arginine at a concentration in the range of 300 mM to 500 mM; and have a pH in the range of pH 9 to 11. In certain embodiments, the refold buffer comprises TRIS at a concentration in the range of 30 mM to 70 mM; Arginine at a concentration in the range of 300 mM to 500 mM; and have a pH in the range of pH 9 to 11. In certain embodiments, the refold buffer comprises TRIS at a concentration of about 50 mM, Arginine at a concentration of about 400 mM, and has a pH of about 10.

Additional agents that may be included in the refold buffer include: other amino acids (e.g. Glycine) that suppress aggregation; sugars (e.g. sucrose) that suppress aggregation; or organic compounds (e.g. propylene glycol) that suppress aggregation.

In certain embodiments, the refold buffer comprises a reducing agent, e.g., 10 mM TCEP. In other embodiments, the refold buffer does not comprise a reducing agent, or does not comprise a significant amount of reducing agent. It is believed that the exclusion of a reducing agent at this stage allows certain disulfide bonds to remain intact, thereby facilitating refolding of the protein. Thus, in certain embodiments, the refold buffer does not comprise a concentration of reducing agent that is sufficient for reducing disulfide bonds.

In exemplary embodiments, a composition comprising solubilized denatured protein is diafiltered with 2-4 volumes of refold buffer for 0.5 to 3 hours at room temperature. In certain embodiments, a composition comprising solubilized denatured protein is diafiltered with 2-4 volumes of refold buffer for 0.5 to 3 hours at room temperature, wherein the refold buffer has a pH of 9 to 11. In certain embodiments, a composition comprising solubilized denatured protein is diafiltered with 2-4 (e.g., 3) volumes of refold buffer for 0.5 to 3 hours at room temperature, wherein the refold buffer has a pH of 9 to 11 and comprises Arginine. In certain embodiments, a composition comprising solubilized denatured protein is diafiltered with 2-4 (e.g., 3) volumes of refold buffer for 0.5 to 3 hours at room temperature, wherein the refold buffer has a pH of 9 to 11, and wherein the refold buffer does not comprise a reducing agent.

The protein composition that is obtained after diafiltering with refold buffer, which is essentially devoid of denaturing concentrations of denaturing agent, is referred to herein as the second protein composition.

Refolding denatured protein using TFF with refold/oxidizing buffer After diafiltering with refold buffer (first refold step) to obtain a second protein composition, the second protein composition is subjected to the second refolding step, wherein the second protein composition is combined with, e.g., by diafiltering, for a time and under conditions appropriate to obtain a third protein composition comprising renatured ro refolded protein.

For stimulating refolding of the protein, the composition comprising partially refolded protein (i.e., the second protein composition) is subject to the second refold step, e.g., it is diafiltered with a buffer that is oxidizing, and referred to herein as the "refold/oxidizing buffer." A refold/oxidizing buffer may comprise a redox system that provides an oxidizing environment to favor disulfide bond formation. For refolding proteins that do not comprise at least one disulfide bond, it is not necessary to include a redox system.

The second refold step with a refold/oxidizing buffer may be performed by any technique for refolding proteins, e.g., by incubating the protein under oxidizing conditions to form disulfide bonds. In certain embodiments, a protein is incubated with a refold/oxidizing buffer. In certain embodiments, a protein is diafiltered with a refold/oxidizing buffer.

Diafiltering with the refold/oxidizing buffer may be conducted with a number of diavolumes of refold/oxidizing buffer and for a time sufficient to refold essentially all of the protein, or at least 70%, 80%, 90%, 95%, 97%, 98% or 99% of the protein. "Refolding a protein" in a composition refers to restoring the three dimensional structure of the protein, and may include reforming all of, or essentially all of, the intrachain and interchain disulfide bonds of the proteins in the composition. A refolded protein is generally biologically active. For example, a refolded $^{10}$Fn3Fc/Fc protein is a protein that has a functional Fc chain and a functional $^{10}$Fn3 portion. As further discussed herein, several methods may be used to determine the level of refolding (or the structure) of a protein.

In certain embodiments, a second protein composition may be diafiltered with 1-10 diavolumes of refold/oxidizing buffer. In certain embodiments, a protein composition is diafiltered with 1-9, 1-8, 1-7, 1-6, 1-5, 1-4, 1-3 or 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6 or 4-5 diavolumes of refold/oxidizing buffer. In certain embodiments, a protein composition is diafiltered with 2-5, 2-6 or 4 diavolumes of refold/oxidizing buffer.

Diafiltering with the refold/oxidizing buffer may be conducted for a time sufficient to refold the protein. In certain embodiments, diafiltering with refold/oxidizing buffer may take from 0.3 hours to 5 hours, 0.3 hours to 4 hours, 0.3 hours to 3 hours, 0.5 hours to 5 hours, 0.5 hours to 4 hours, or 0.5 hours to 3 hours.

In certain embodiments, a refold/oxidizing buffer comprises a buffering agent suitable for maintaining the pH of the refold/oxidizing buffer or that of the composition comprising the refold/oxidizing buffer and solubilized protein (the "refold reaction") in a range of pH of 9 to 11. The pH of the refold/oxidizing buffer or the refold reaction may also be within the following ranges of pH: pH 9.3 to 10.8; pH 9.5 to 10.5; pH 9.8 to 10.2, e.g., pH 10.

A refold/oxidizing buffer may comprise Arginine (or another amino acid, such as Cysteine), e.g., L-arginine/HCl (which is encompassed by the term "Arginine"). A refold/oxidizing buffer may comprise Arginine at a concentration that is sufficient for buffering the refold/oxidizing buffer at the desired pH, such as pH 9.3 to 10.8; pH 9.5 to 10.5; pH 9.8 to 10.2, e.g., pH 10. Arginine may be present at concentrations in the range of 50 mM to 500 mM; 100 mM to 500 mM; 200 mM to 500 mM; 300 mM to 500 mM; 350 mM to 450 mM. In certain embodiments, the refold/oxidizing buffer includes Arginine at a concentration of 300 mM to 400 mM. In certain embodiments, a refold/oxidizing buffer comprises Arginine at 50 mM to 500 mM and has a pH in the range of 9 to 11. In certain embodiments, a refold/oxidizing buffer comprises Arginine at 200 mM to 500 mM and has a pH in the range of 9.5 to 10.5.

As Arginine buffers the pH of a solution around pH 10, it is not necessary to include another buffer in the refold/oxidizing buffer. However, in certain embodiments, one may include one or more of the following buffers: TRIS (Tris [hydroxymethyl]aminomethane), HEPPS (N-[2-Hydroxyethyl]piperazine-N'-[3-propane-sulfoni c acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In certain embodiments, the refold/oxidizing buffer includes a buffer, e.g., TRIS, at a concentration of 1 mM to 1 M; 1 mM to 100 mM; 10 mM to 100 nM; 10 mM to 50 mM; 50 mM to 100 mM; 30 mM to 70 mM; or 40 mM to 60 mM. In certain embodiments, the refold/oxidizing buffer comprises a buffer, e.g., TRIS, at a concentration of about 50 mM. In certain embodiments, the refold/oxidizing buffer comprises TRIS, e.g., at 40-60 mM, and has a pH in the range of pH 9 to 11.

Refold/oxidizing buffer may comprise TRIS and Arginine and have a pH in the range of pH 9 to 11. In certain embodiments, the refold/oxidizing buffer comprises TRIS at a concentration in the range of 10 mM to 100 mM; Arginine; and have a pH in the range of pH 9 to 11. The refold/oxidizing buffer may comprise TRIS and Arginine, wherein Arginine is at a concentration in the range of 300 mM to 500 mM; and have a pH in the range of pH 9 to 11. The refold/oxidizing buffer may comprise TRIS at a concentration in the range of 10 mM to 100 mM; Arginine at a concentration in the range of 300 mM to 500 mM; and have a pH in the range of pH 9 to 11. In certain embodiments, the refold/oxidizing buffer comprises TRIS at a concentration in the range of 30 mM to 70 mM; Arginine at a concentration in the range of 300 mM to 500 mM; and have a pH in the range of pH 9 to 11. In certain embodiments, the refold/oxidizing buffer comprises TRIS at a concentration of about 50 mM, Arginine at a concentration of about 400 mM, and has a pH of about 10.

Additional agents that may be included in the refold/oxidizing buffer include: other amino acids (e.g. Glycine) that suppress aggregation; sugars (e.g. sucrose) that suppress aggregation; or organic compounds (e.g. propylene glycol) that suppress aggregation.

The refold/oxidizing buffer may also comprise an oxidizing agent to facilitate the formation of disulfide bonds. In certain embodiments, the refold/oxidizing buffer comprises glutathione, e.g., in a ratio of oxidized glutathione: reduced glutathione of about 5:1 or a similar ratio sufficient to facilitate the formation of disulfide bonds. In certain embodiments, a refold/oxidizing buffer comprises 0.1 mM to 10 mM of oxidized glutathione and 0.02 mM to 2 mM of reduced glutathione. In certain embodiments, a refold/oxidizing buffer comprises 0.5 mM to 2 mM of oxidized glutathione and 0.1 to 0.4 mM of reduced glutathione. In certain embodiments, a refold/oxidizing buffer comprises about 1 mM of oxidized glutathione and about 0.2 mM of reduced glutathione. Other oxidizing agents that may be used include: cysteine and cystine; or cystine or oxidized glutathione with another reducing agent (e.g. DTT, TCEP).

Diafiltering with refold/oxidizing buffer may be conducted at a temperature, e.g., ranging from 2° C. to 40° C.; 4° C. to 37° C.; 25° C. to 37° C.; room temperature; or 4° C. to 25° C.

In certain embodiments, a composition comprising partially refolded protein (second protein composition) is diafiltered with 2-6 volumes of refold/oxidizing buffer for 0.5 to 3 hours at room temperature. In certain embodiments, a composition comprising partially refolded protein (second protein composition) is diafiltered with 4-6 volumes of refold buffer for 0.5 to 3 hours at room temperature, wherein the refold/oxidizing buffer has a pH of 9 to 11. In certain embodiments, a composition comprising partially refolded protein (second protein composition) is diafiltered with 2-6 volumes of refold/oxidizing buffer for 0.5 to 3 hours at room temperature, wherein the refold/oxidizing buffer has a pH of 8 to 11 and comprises Arginine. In certain embodiments, a composition comprising partially refolded protein (second protein composition) is diafiltered with 2-6 volumes of refold/oxidizing buffer for 0.5 to 3 hours at room temperature, wherein the refold/oxidizing buffer has a pH of 9 to 11, and wherein the refold buffer comprises glutathione.

Following the adjustment to a lower pH, the reaction mixture may be incubated for 30 minutes to 3 hours; or for 30 minutes to 2 hours, prior to a next step, e.g., a purification step. A refolded protein may be further processed, e.g., purified, according to methods known in the art, e.g., using protein A chromatography and other types of chromatography or purification methods.

Protein concentration before, during and after diafiltering may be from 1 mg/ml or less to at least 10 mg/ml. For example, the protein concentration may be about 5 mg/ml, 6 mg/ml, 7 mg/ml, 8 mg/ml, 9 mg/ml or 10 mg/ml during solubilization, diafiltering with refold buffer and diafiltering with refold/oxidizing buffer.

Refolding can be analyzed with SE-HPLC, RP-HPLC/MS, and SDS-SAGE. In certain embodiments, total recovery of protein refolded as described herein may be at least 70%, 80%, 85%, or 90% as measured by reverse phase chromatography. In certain embodiments, the final purity, as determined by SEC was at least 70%, 80%, 85%, 90%, or 95%.

During standard expression and purification of recombinant protein comprising an Fc, the disulfide bond of the CH3 region (CH3 loop) is unformed in about 1-3% of the protein composition. Using certain methods described herein, the CH3 open loop has also been shown to be in the range of 1-3% in the refolded proteins. Accordingly certain Fc containing protein compositions, wherein the proteins have been refolded as described herein, have less than 5%, 4%, 3%, 2%, 1% CH3 open loops.

In certain embodiments, refolding denatured protein, e.g., from an IB, is performed in less than 4 hours, 3 hours, or 2 hours.

Exemplary methods A method for refolding denatured protein, e.g., in the form of an IB, may comprise: (i) combining (and optionally mixing) denatured protein with a solubilization buffer comprising 4 to 8 M guanidine, TRIS at a concentration in the range of 30 mM to 70 mM; and having a pH in the range of pH 7 to 10; at a ratio of weight (grams) of denatured protein: volume (ml) of solubilization buffer of 1:5-50, wherein the incubation is conducted at room temperature for 1 to 120 minutes, to thereby obtain a composition comprising solubilized denatured protein; (ii) diafiltering the composition comprising solubilized denatured protein with 2-4 diavolumes of refold buffer comprising Arginine at a concentration in the range of 300 mM to 500 mM; optionally TRIS at a concentration in the range of 30 mM to 70 mM; and having a pH in the range of pH 9 to 11; and (iii) combining the composition comprising partially refolded protein with refold/oxidizing buffer; and wherein the method does not comprise using a significant amount of a reducing agent (other than reduced glutathione).

A method for refolding denatured protein, e.g., in the form of an IB, may comprise: (i) combining (and optionally mixing) denatured protein with a solubilization buffer comprising 4 to 8 M guanidine, TRIS at a concentration in the range of 30 mM to 70 mM; and having a pH in the range of pH 7 to 10; at a ratio of weight (grams) of denatured protein: volume (ml) of solubilization buffer of 1:5-50, wherein the incubation is conducted at room temperature for 1 to 120 minutes, to thereby obtain a composition comprising solubilized denatured protein; (ii) diafiltering the composition comprising solubilized denatured protein with 2-4 diavolumes of refold buffer comprising Arginine at a concentration in the range of 300 mM to 500 mM; optionally TRIS at a concentration in the range of 30 mM to 70 mM; and having a pH in the range of pH 9 to 11; and (iii) diafiltering the composition comprising partially refolded protein with 2-6 diavolumes of refold/oxidizing buffer comprising Arginine at a concentration in the range of 300 mM to 500 mM; optionally TRIS at a concentration in the range of 30 mM to 70 mM; oxidized glutathione at a concentration in the range of 0.5 mM to 2 mM; reduced glutathione at a concentration in the range of 0.1 mM to 0.4 mM; and having a pH in the range of pH 9 to 11; and wherein the method does not comprise using a significant amount of a reducing agent (other than reduced glutathione).

A method for refolding a denatured protein, e.g., from an IB, may comprise: (i) suspending a pellet of denatured protein, e.g., an IB pellet, in suspension solution (e.g., water) at a ratio of weight or volume of denatured protein pellet: volume of suspension solution of 1:1-5 at room temperature for 1-60 minutes to thereby obtain a composition comprising a suspension of denatured protein; (ii) combining (and optionally mixing) the composition comprising a suspension of denatured protein with a solubilization buffer comprising 4 to 6 M guanidine, TRIS at a concentration in the range of 30 mM to 70 mM; and having a pH in the range of pH 7 to 10; at a ratio of weight (grams) of denatured protein: volume (ml) of solubilization buffer of 1:5-50; wherein the incubation is conducted at room temperature for 1 to 60 minutes, to thereby obtain a composition comprising solubilized denatured protein; (iii) diafiltering the composition comprising solubilized denatured protein with 2-4 diavolumes of refold buffer comprising Arginine at a concentration in the range of 300 mM to 500 mM; optionally TRIS at a concentration in the range of 30 mM to 70 mM; and having a pH in the range of pH 9 to 11; at a ratio of weight (grams) of denatured protein: volume of refold buffer (ml) of 1:5-50; and (iv) combining the composition comprising partially refolded protein with refold/oxidizing buffer; and wherein the method does not comprise using a significant amount of a reducing agent (other than reduced glutathione).

A method for refolding a denatured protein, e.g., from an IB, may comprise: (i) suspending a pellet of denatured protein, e.g., an IB pellet, in suspension solution (e.g., water) at a ratio of weight or volume of denatured protein pellet: volume of suspension solution of 1:1-5 at room temperature for 1-60 minutes to thereby obtain a composition comprising a suspension of denatured protein; (ii) combining (and optionally mixing) the composition comprising a suspension of denatured protein with a solubilization buffer comprising 4 to 6 M guanidine, TRIS at a concentration in the range of 30 mM to 70 mM; and having a pH in the range of pH 7 to 10; at a ratio of weight (grams) of denatured protein: volume (ml) of solubilization buffer of 1:5-50; wherein the incubation is conducted at room temperature for 1 to 60 minutes, to thereby obtain a composition comprising solubilized denatured protein; (iii) diafiltering the composition comprising solubilized denatured protein with 2-4 diavolumes of refold buffer comprising Arginine at a concentration in the range of 300 mM to 500 mM; optionally TRIS at a concentration in the range of 30 mM to 70 mM; and having a pH in the range of pH 7 to 10; at a ratio of weight (grams) of denatured protein: volume of refold buffer (ml) of 1:5-50; and (iv) diafiltering the composition comprising partially refolded protein with 2-6 diavolumes of refold/oxidizing buffer comprising Arginine at a concentration in the range of 300 mM to 500 mM; optionally TRIS at a concentration in the range of 30 mM to 70 mM; oxidized glutathione at a concentration in the range of 0.5 mM to 2 mM; reduced glutathione at a concentration in the range of 0.1 mM to 0.4 mM; and having a pH in the range of pH 9 to 11; and wherein the method does not comprise using a significant amount of a reducing agent (other than reduced glutathione).

A method for refolding denatured protein, e.g., in the form of an IB, may comprise: (i) combining (and optionally mixing) denatured protein with a solubilization buffer comprising 6M guanidine, 50 mM TRIS pH 8; at a ratio of weight (grams) of denatured protein: volume (ml) of solubilization buffer of 1:10-30, wherein the incubation is conducted at room temperature for 60 minutes, to thereby obtain a composition comprising solubilized denatured protein; (ii) diafiltering the composition comprising solubilized denatured protein with 3 diavolumes of refold buffer comprising 400 mM Arginine; optionally 50 mM TRIS pH 10; and having a pH of about 10; and (iii) combining the composition comprising partially refolded protein with refold/oxidizing buffer; and wherein the method does not comprise using a significant amount of a reducing agent (other than reduced glutathione).

A method for refolding denatured protein, e.g., in the form of an IB, may comprise: (i) combining (and optionally mixing) denatured protein with a solubilization buffer comprising 6M guanidine, 50 mM TRIS pH 8; at a ratio of weight (grams) of denatured protein: volume (ml) of solubilization buffer of 1:10-30, wherein the incubation is conducted at room temperature for 60 minutes, to thereby obtain a composition comprising solubilized denatured protein; (ii) diafiltering the composition comprising solubilized denatured protein with 3 diavolumes of refold buffer comprising 400 mM Arginine; optionally 50 mM TRIS pH 10; and having a pH of about 10; and (iii) diafiltering the composition comprising partially refolded protein with 4 diavolumes of refold/oxidizing buffer comprising 400 mM Arginine; optionally 50 mM TRIS pH 10; 1 mM oxidized glutathione (GSSG); 0.2 mM reduced glutathione (GSH); and having a pH of about 10; and wherein the method does not comprise using a significant amount of a reducing agent (other than reduced glutathione).

A method for refolding a denatured protein, e.g., from an IB, may comprise: (i) suspending a pellet of denatured protein, e.g., an IB pellet, in suspension solution (e.g., water) at a ratio of weight (grams) or volume (ml) of denatured protein pellet: volume (ml) of suspension solution of 1:1-5 at room temperature for 1-60 minutes to thereby obtain a composition comprising a suspension of denatured protein; (ii) combining (and optionally mixing) denatured protein with a solubilization buffer comprising 6M guanidine, 50 mM TRIS pH 8; at a ratio of weight of denatured protein: volume of solubilization buffer of 1:10-50, wherein the incubation is conducted at room temperature for 60 minutes, to thereby obtain a composition comprising solubilized denatured protein; (iii) diafiltering the composition comprising solubilized denatured protein with 3 diavolumes of refold buffer comprising 400 mM Arginine; optionally 50 mM TRIS pH 10; and (iv) combining the composition comprising partially refolded protein refold/oxidizing buffer; and wherein the method does not comprise using a significant amount of a reducing agent (other than reduced glutathione).

A method for refolding a denatured protein, e.g., from an IB, may comprise: (i) suspending a pellet of denatured protein, e.g., an IB pellet, in suspension solution (e.g., water) at a ratio of weight (grams) or volume (ml) of denatured protein pellet: volume (ml) of suspension solution of 1:1-5 at room temperature for 1-60 minutes to thereby obtain a composition comprising a suspension of denatured protein; (ii) combining (and optionally mixing) denatured protein with a solubilization buffer comprising 6M guanidine, 50 mM TRIS pH 8; at a ratio of weight of denatured protein: volume of solubilization buffer of 1:10-50, wherein the incubation is conducted at room temperature for 60 minutes, to thereby obtain a composition comprising solubilized denatured protein; (iii) diafiltering the composition comprising solubilized denatured protein with 3 diavolumes of refold buffer comprising 400 mM Arginine; optionally 50 mM TRIS pH 10; and (iv) diafiltering the composition comprising partially refolded protein with 4 diavolumes of refold/oxidizing buffer comprising 400 mM Arginine; optionally 50 mM TRIS pH 10; 1 mM oxidized glutathione (GSSG); 0.2 mM reduced glutathione (GSH); and wherein the method does not comprise using a significant amount of a reducing agent (other than reduced glutathione).

Exemplary Proteins

Proteins that may be refolded from a denatured state, e.g., from IBs, using the methods described herein include any protein that is in a denatured form, e.g., proteins comprising at least one disulfide bond in their native state. Proteins without disulfide bonds may also be refolded as described herein. Proteins may comprise a binding domain that specifically binds to a target protein. A protein may be a naturally occurring protein or a genetically engineered or fusion protein. An exemplary protein that may be refolded as described herein is an Fc containing protein, such as an Fc fused to a heterologous domain (e.g., a non-Fc or non-antibody domain). A heterologous protein may be any protein, including an antigen binding portion of an antibody and derivatives thereof, e.g., Fabs, scFvs, bispecific scFvs, single domain antibodies ("sdAbs") (e.g., $V_HH$ or camelid antibodies and VNAas), diabodies (dAbs), single chain diabodies (scDb), Darpins, anticalins, and fibronectin based scaffolds, such as $^{10}$Fn3, Fibcons and Tencons. A full length antibody may also be refolded as described herein. Heterologous proteins linked to Fc may also be unrelated to antibodies and may be, e.g., TNFR.

Fibronectin Based Scaffolds

As used herein, a "fibronectin based scaffold" or "FBS" protein or moiety refers to proteins or moieties that are based on a fibronectin type III ("Fn3") repeat. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork & Doolittle, Proc Natl Acad Sci USA 89(19):8990-4 (1992); Bork et al., J Mol Biol. 242(4):309-20 (1994); Campbell & Spitzfaden, Structure 2(5):333-7 (1994); Harpez & Chothia, J Mol Biol. 238(4):528-39 (1994)). The term "fibronectin based scaffold" protein or moiety is intended to include scaffolds based on Fn3 domains from these other proteins (i.e., non fibronectin molecules).

An example of fibronectin-based scaffold proteins are Adnectins (Adnexus, a wholly owned subsidiary of Bristol-Myers Squibb). It has been shown that the CDR-like loop regions of the fibronectin based scaffolds can be modified to evolve a protein capable of binding to any compound of interest. For example, U.S. Pat. No. 7,115,396 describes Fn3 domain proteins wherein alterations to the BC, DE, and FG loops result in high affinity TNFc binders. U.S. Pat. No. 7,858,739 describes Fn3 domain proteins wherein alterations to the BC, DE, and FG loops result in high affinity VEGFR2 binders.

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in ligand binding.

In exemplary embodiments, the ligand binding fibronectin based scaffold moieties described herein are based on the tenth fibronectin type III domain, i.e., the tenth module of Fn3 ($^{10}$Fn3). The amino acid sequence of wild-type human $^{10}$Fn3 (with N-terminal tail (in italics)) is set forth in SEQ ID NO: 1:

(SEQ ID NO: 1)
*VSDVPRDLEVVAA*TPTSLLISWDAPAVTVRYYRITYGETGGNSPVQEFTV

PGSKSTATISGLKPGVDYTITVYAVTGRGDSPASSKPISINYR*TEIDKPS*

*Q*

(the AB, CD and EF loops are underlined; the BC, FG, and DE loops are emphasized in bold; the β-strands are located between each of the loop regions; and the N-terminal and C-terminal regions are shown in italics). Wild-type $^{10}$Fn3 without the tail set forth in italics in SEQ ID NO: 1 is provided as SEQ ID NO: 5.

In some embodiments, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87 of SEQ ID NO: 1. The BC, DE and FG loops align along one face of the molecule, i.e. the "north pole", and the AB, CD and EF loops align along the opposite face of the molecule, i.e. the "south pole". In SEQ ID NO: 1, β-strand A corresponds to residues 8-13, β-strand B corresponds to residues 18-22, β-strand C corresponds to residues 32-36, beta strand D corresponds to residues 48-50, β-strand E corresponds to residues 57-62, β-strand F corresponds to residues 68-74, and β-strand G corresponds to residues 88-92. The 3-strands are connected to each other through the corresponding loop, e.g., strands A and B are connected via loop AB in the formation β-strand A, loop AB, β-strand B, etc. The N-terminal and/or C-terminal regions of SEQ ID NO: 1 (italicized above), may be removed or altered to generate a molecule retaining biological activity and comprising, e.g., an amino acid sequence selected from the group consisting of SEQ ID NOs: 2-16. In certain embodiments, the first 8 amino acid residues of SEQ ID NO: 1 and/or the last 7 amino acid residues of SEQ ID NO: 1 (i.e., amino acid residues 1-8 and 95-101 of SEQ ID NO: 1, respectively) may be removed or altered to generate a polypeptide comprising the amino acid sequence of SEQ ID NO: 4.

As described above, amino acid residues corresponding to residues 14-17, 23-31, 37-47, 51-56, 63-67 and 75-87 of SEQ ID NO: 1 define the AB, BC, CD, DE, EF and FG loops, respectively. However, it should be understood that not every residue within a loop region needs to be modified in order to achieve a $^{10}$Fn3 binding domain having strong affinity for a desired target. Additionally, insertions and deletions in the loop regions may also be made while still producing high affinity $^{10}$Fn3 binding domains.

Accordingly, in some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof.

In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. To optimize antigen binding in polypeptides relying on the FG for target binding, therefore, the length of the FG loop of $^{10}$Fn3 may be altered in length as well as in sequence to obtain the greatest possible flexibility and affinity in target binding.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In another embodiment, the RGD sequence is replaced with SGE. In yet another embodiment, the RGD sequence is replaced with RGE (see, e.g., SEQ ID NO: 16).

As used herein, a "$^{10}$Fn3 domain" or "$^{10}$Fn3 moiety" refers to wild-type $^{10}$Fn3 (e.g., comprising one of SEQ ID NOs: 1-8, 10, 12, 14 or 16) and biologically active variants thereof, e.g., biologically active variants that specifically bind to a target, such as a target protein and biologically active variants having SEQ ID NO: 9, 11, 13 or 15. A wild type $^{10}$Fn3 domain may comprise one of the amino acid sequenced set forth in SEQ ID NO: 1-8, 10, 12, 14 and 16. Biologically active variants of a $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising any one of SEQ ID NOs: 1-16. A biologically active variant of a $^{10}$Fn3 domain may also comprise, or comprise at most, 1-3, 1-5, 1-10, 1-15, 1-10, or 1-25 amino acid changes relative to a $^{10}$Fn3 domain comprising any one of SEQ ID NOs: 1-16. In certain embodiments, a biologically active variant of a $^{10}$Fn3 domain does not comprise more than 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to an $^{10}$Fn3 domain comprising any one of SEQ ID NOs: 1-16. Amino acid changes may be in a loop region and/or in a strand. Exemplary degenerate $^{10}$Fn3 amino acid sequences are provided herein as SEQ ID NOs: 17-29.

In some embodiments, a fibronectin based scaffold moiety comprises a $^{10}$Fn3 domain having at least 40%, 50%, 55%, 60%, 65%, 70%, 75%, 80%, 85%, or 90% identity to a human $^{10}$Fn3 domain having an amino acid sequence selected from the group of sequence comprising SEQ ID NOs: 1-16. In certain embodiments, the fibronectin based scaffold moiety provided herein have at least 50% identity to an amino acid sequence selected from the group of amino acid sequences comprising SEQ ID NO: 1-16. In other embodiments, the fibronectin based scaffold moiety has at least 65% identity to an amino acid sequence selected from the group of amino acid sequences comprising SEQ ID NO: 1-16. In certain embodiments, one or more of the loops will not be modified relative to the sequence of the corresponding loop of the wild-type sequence and/or one or more of the β-strands will not be modified relative to the sequence of the corresponding β-strand of the wild-type sequence. In certain embodiments, each of the beta or beta-like strands of a $^{10}$Fn3 domain in a fibronectin based scaffold moiety may comprise, consist essentially of, or consist of an amino acid sequence that is at least 80%, 85%, 90%, 95% or 100% identical to the sequence of a corresponding beta or beta-like strand of SEQ ID NO: 1. Preferably, variations in the β-strand regions will not disrupt the stability of the polypeptide in physiological conditions. In exemplary embodiments, the $^{10}$Fn3 domain binds to a desired target with a $K_d$ of less than 500 nM, 100 nM, 50 nM, 10 nM, 5 nM, 1 nM, 500 pM, 100 pM or less. In some embodiments, the $^{10}$Fn3 domain of a fibronectin based protein scaffold binds to a desired target with a $K_d$ between 1 pM and 1 μM, between 100 pM and 500 nM, between 1 nM and 500 nM, or between 1 nM and 100 nM. In exemplary embodiments, the fibronectin based scaffold moiety binds specifically to a target that is not bound by a wild-type $^{10}$Fn3 domain, particularly the wild-type human $^{10}$Fn3 domain having, e.g., SEQ ID NO: 1-8, 10, 12, 14 or 16.

In some embodiments, fusion proteins comprise a fibronectin based scaffold moiety comprising a $^{10}$Fn3 domain, wherein the $^{10}$Fn3 domain comprises a loop, AB; a loop, BC; a loop, CD; a loop, DE; a loop, EF; and a loop, FG; and has at least one loop selected from loop AB, BC, CD, DE, EF and FG with an altered amino acid sequence relative to the sequence of the corresponding loop of the human $^{10}$Fn3 domain of SEQ ID NO: 1-16. In some embodiments, the BC, DE and FG loops are altered. In certain embodiments, the AB, CD and EF loops are altered. In certain embodiments, the FG loop is the only loop that is altered. In other embodiments, the CD and FG loops are both altered, and optionally, no other loops are altered. In certain embodiments, the CD and EF loops are both altered, and optionally, no other loops are altered. In some embodiments, one or more specific scaffold alterations are combined with one or more loop alterations. By "altered" is meant one or more amino acid sequence alterations relative to a template sequence (i.e., the corresponding wild-type human fibronectin domain) and includes amino acid additions, deletions, and substitutions.

In some embodiments, the fibronectin based scaffold moiety comprises a $^{10}$Fn3 domain wherein the non loop regions comprise an amino acid sequence that is at least 80, 85, 90, 95, 98, or 100% identical to the non-loop regions of SEQ ID NO: 1, wherein at least one loop selected from AB, BC, CD, DE, EF and FG is altered. For example, in certain embodiments, the AB loop may have up to 4 amino acid substitutions, up to 10 amino acid insertions, up to 3 amino acid deletions, or a combination thereof; the BC loop may have up to 10 amino acid substitutions, up to 4 amino acid deletions, up to 10 amino acid insertions, or a combination thereof; the CD loop may have up to 6 amino acid substitutions, up to 10 amino acid insertions, up to 4 amino acid deletions, or a combination thereof; the DE loop may have up to 6 amino acid substitutions, up to 4 amino acid deletions, up to 13 amino acid insertions, or a combination thereof; the EF loop may have up to 5 amino acid substitutions, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof.

In certain embodiments, a fibronectin based scaffold moiety comprises an amino acid sequence that is at least 40%, 50%, 60%, 70%, 75%, 80%, 85%, 90%, 95%, 97%, 98%, or 99% identical to an amino acid sequence selected from the group of sequences consisting of SEQ ID NOs: 1-16, and the fusion protein binds specifically to a target, e.g., with a $K_d$ of less than 500 nM, 100 nM, 50 nM, 10 nM, 5 nM, 1 nM, 500 pM, 100 pM or less. The proteins may comprise amino acid changes (or alterations) in one or more loops and one or more strands.

In certain embodiments, the fibronectin based scaffold moiety comprises a $^{10}$Fn3 domain that is defined generally by following the sequence:

(SEQ ID NO: 17)
VSDVPRDLEVVAA(X)$_u$LLISW(X)$_v$YRITY(X)$_w$FTV(X)$_x$ATISGL(X)$_y$

YTITVYA(X)$_z$ISINYRT, or by the sequence having SEQ ID NO: 18-29. In SEQ ID NOs: 17-29, the AB loop is represented by (X)$_u$, the BC loop is represented by (X)$_v$, the CD loop is represented by (X)$_w$, the DE loop is represented by (X)$_x$, the EF loop is represented by (X)$_y$, and the FG loop is represented by X$_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NOs: 17-29. In some embodiments, the sequences of the beta strands may have anywhere from 0 to 10, from 0 to 8, from 0 to 6, from 0 to 5, from 0 to 4, from 0 to 3, from 0 to 2, or from 0 to 1 substitutions, e.g., conservative substitutions, across all 7 scaffold regions relative to the corresponding amino acids shown in SEQ ID NO: 17-29. In certain embodiments, the hydrophobic core amino acid residues (bolded residues in SEQ ID NO: 17 above) are fixed, and any substitutions, conservative substitutions, deletions or additions occur at residues other than the hydrophobic core amino acid residues. In some embodiments, the hydrophobic core residues of the polypeptides provided herein have not been modified relative to the wild-type human $^1$Fn3 domain (e.g., SEQ ID NO: 5).

In some embodiments, the amino acid sequences of the N-terminal and/or C-terminal regions of a fibronectin based scaffold moiety may be modified by deletion, substitution or insertion relative to the amino acid sequences of the corresponding regions of $^{10}$Fn3 domains comprising one of SEQ ID NOs: 1-16). In some embodiments, the first eight (i.e., residues 1-8) and the last seven amino acids (i.e., residues 95-101) of SEQ ID NO: 1 are deleted, generating a $^{10}$Fn3 domain having the amino acid sequence of SEQ ID NO: 4. Additional sequences may also be added to the N- or C-terminus of a $^1$Fn3 domain having the amino acid sequence of any one of SEQ ID NOs: 1-16. For example, in some embodiments, the N-terminal extension consists of an amino acid sequence selected from the group consisting of: M, MG, and G.

In certain embodiments, the amino acid sequence of the first 1, 2, 3, 4, 5, 6, 7, 8 or 9 residues of SEQ ID NO: 1 may be modified or deleted in the polypeptides provided herein relative to the sequence of the corresponding amino acids in the wild-type human $^{10}$Fn3 domain having SEQ ID NO: 1. In exemplary embodiments, the amino acids corresponding to amino acids 1-8 of SEQ ID NO: 1 are replaced with an alternative N-terminal region having from 1-20, 1-15, 1-10, 1-8, 1-5, 1-4, 1-3, 1-2, or 1 amino acids in length. Exemplary alternative N-terminal regions include (represented by the single letter amino acid code) M, MG, G, MGVSDVPRDL (SEQ ID NO: 30) and GVSDVPRDL (SEQ ID NO: 31), or N-terminal truncations of any one of SEQ ID NOs: 30 and 31. Other suitable alternative N-terminal regions include, for example, X$_n$SDVPRDL (SEQ ID NO: 32), XnDVPRDL (SEQ ID NO: 33), XnVPRDL (SEQ ID NO: 34), XnPRDL (SEQ ID NO: 35), XnRDL (SEQ ID NO: 36), XnDL (SEQ ID NO: 37), or XnL, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In other embodiments, the alternative N-terminal region comprises the amino acid sequence MASTSG (SEQ ID NO: 38).

In certain embodiments, the amino acid sequence corresponding to amino acids 93-101, 94-101, 95-101, 96-101, 97-101, 98-101, 99-101, 100-101, or 101 of SEQ ID NO: 1 are deleted or modified in the polypeptides provided herein relative to the sequence of the corresponding amino acids in the wild-type human $^{10}$Fn3 domain (SEQ ID NO: 1). In exemplary embodiments, the amino acids corresponding to amino acids 95-101 of SEQ ID NO: 1 are replaced with an alternative C-terminal region having from 1-20, 1-15, 1-10, 1-8, 1-5, 1-4, 1-3, 1-2, or 1 amino acids in length. Specific examples of alternative C-terminal region sequences include, for example, polypeptides comprising, consisting essentially of, or consisting of, EIEK (SEQ ID NO: 39), EGSGC (SEQ ID NO: 40), EIEKPCQ (SEQ ID NO: 41), EIEKPSQ (SEQ ID NO: 42), EIEKP (SEQ ID NO: 43), EIEKPS (SEQ ID NO: 44), EIEKPC (SEQ ID NO: 45), or HHHHHH (SEQ ID NO: 46).

In some embodiments, the alternative C-terminal region comprises EIDK (SEQ ID NO: 47), and in particular embodiments, the alternative C-terminal region is either EIDKPCQ (SEQ ID NO: 48) or EIDKPSQ (SEQ ID NO: 49).

In certain embodiments, a fibronectin based scaffold moiety comprises a $^{10}$Fn3 domain having both an alternative N-terminal region sequence and an alternative C-terminal region sequence.

In certain embodiments, a fibronectin based scaffold moiety is based on an Fn3 repeat other than the 10$^{th}$ repeat of the type III domain of fibronectin, e.g., human fibronectin. For example, a fibronectin based scaffold moiety may be similar to any of the other fibronectin type III repeats, e.g., the 1$^{st}$, 2nd, 3rd, 4th, 5th, 6th, 7th, 8th, 9th, 11th, 12th, 13th, 14th, 15th, 16th, 17th, and 18th Fn3 repeats. In yet other embodiments, a fibronectin based scaffold moiety may be from a molecule other than fibronectin. Exemplary fibronectin based scaffold moieties may be derived from tenascin, a protein that is composed of 15 Fn3 domains with similar sequence similarities to one another as found in fibronectin. These repeats are described, e.g., in Jacobs et al. (2012) Protein Engineering, Design & Selection 25:107. Based on the homology of the repeats in the fibronectin molecule and those in the tenascin molecule, artificial molecules based on these homologies have been created. The consensus amino acid sequences based on the homology of the domains in the fibronectin molecule are referred to as Fibcon and FibconB (WO2010/093627 and Jacobs et al. (2012) supra) and those based on the homology of the domains in the tenascin molecule are referred to as Tencon. An exemplary Fibcon amino acid sequence comprises the following amino acid sequence: MPAPTDLRFTNETPSSLLISWTP-PRVQITGYIIRYGPVGSDGRVKEFTVPPSVSSATI TGLKPGTEYTISVIALKDNQESEPLRGRVTTGG (FibconB; SEQ ID NO: 50), wherein loop AB consists of amino acids 13-16 (TPSS; SEQ ID NO: 51), loop BC consists of amino acids 22-28 (TPPRVQI; SEQ ID NO: 52), loop CD consists of amino acids 38-43 (VGSDGR; SEQ ID NO: 53), loop DE consists of amino acids 51-54 (PSVS; SEQ ID NO: 54), loop EF consists of amino acids 60-64 (GLKPG; SEQ ID NO: 55) and loop FG consist of amino acids 75-81 (KDNQESEP; SEQ ID NO: 56). Another Fibcon amino acid sequence comprises the following amino acid sequence: LDAPTDLQVTNVTDTSITVSWTPPSATITGYRI-TYTPSNGPGEPKELTVPPSSTSVTI TGITPGVEYVVSVYALKDNQESPPLVGTCTT (SEQ ID NO: 57; Jacobs et al., supra).

Tenascin derived Fn3 proteins include Tencons (WO2010/051274, WO2010/051310 and WO2011/137319, which are specifically incorporated by reference herein). An exemplary Tencon protein has the following amino acid sequence: LPAPKNLVVSEVTED SLRLSWTAPDAAFD SFLIQYQESEKVGEAINLTVPGSERSY DLTGLKPGTEYTVSIYGVKGGHRSNPLSAEFTT (SEQ ID NO: 58; Jacobs et al., supra, and WO2011/137319), wherein loop AB consists of amino acids 13-16 (TEDS; SEQ ID NO: 59, loop BC consists of amino acids 22-28 (TAPDAAF; SEQ ID NO: 60), loop CD consists of amino acids 38-43 (SEKVGE; SEQ ID NO: 61), loop DE consists of amino acids 51-54 (GSER; SEQ ID NO: 62), loop EF consists of amino acids 60-64 (GLKPG; SEQ ID NO: 63) and loop FG consists of amino acids 75-81 (KGGHRSN; SEQ ID NO: 64).

A Fibcon, FibconB or Tencon moiety, or target binding variants thereof, whether by themselves or linked to a heterologous moiety, e.g., an Fc, may be refolded as described herein. Fn3 domains from other proteins, e.g., cell surface hormone and cytokine receptors, chaperonins, and carbohydrate-binding domains, may also be refolded as described herein, either on their own or as part of a fusion protein to, e.g., Fc.

Fibronectin based scaffold proteins or moieties are described, e.g., in WO2010/093627, WO2011/130324, WO2009/083804, WO2009/133208, WO02/04523, WO2012/016245, WO2009/023184, WO2010/051310, WO2011/020033, WO2011/051333, WO2011/051466, WO2011/092233, WO2011/100700, WO2011/130324, WO2011/130328, WO2011/137319, WO2010/051274, WO2009/086116, WOOi, 58379 and WO2013/067029 (all of which are specifically incorporated by reference herein, in particular, the various types of molecules are specifically incorporated by reference herein): any of the fibronectin based scaffold proteins or moieties described in these publications may be refolded as described herein.

In certain embodiments, a protein that may be refolded as described herein is a multivalent protein that comprises two or more fibronectin based scaffold moieties, e.g., $^{10}$Fn3 domains. For example, a multivalent fusion protein may comprise 2, 3 or more fibronectin based scaffold moieties, e.g., $^{10}$Fn3 domains, that are covalently associated. In exemplary embodiments, the fusion protein is a bispecific or dimeric protein comprising two $^{10}$Fn3 domains.

Fc Domains

Proteins that may be refolded as described herein include fusion proteins that comprise an Fc portion fused to a heterologous portion. In some aspects, the heterologous portion is a fibronectin based scaffold, e.g., an $^{10}$Fn3 domain, however, the heterologous portion may be any other protein.

As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. The term "Fc moiety" or "Fc domain" as used herein refers to any of the combination of CH1, hinge, CH2, CH3 and CH4 domains. Thus, an "Fc domain" or moiety may or may not comprise a hinge.

Shown below is the sequence of a human IgG1 immunoglobulin constant region, and the relative position of each domain within the constant region are indicated based on the EU numbering format:

(SEQ ID NO: 65)
*ASTKGPSVFPLAPSSKSTSGGTAALGCLVKDYFPEPVTVSWNSGALTSGV*

*HTFPAVLQSSGLYSLSSVVTVPSSSLGTQTYICNVNHKPSNTKVDKKVEP*

*KSC*<u>DKTHTCPPC</u>PAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The core hinge sequence is underlined, and the CH1 region is italicized; the CH2 and CH3 regions are in regular text. It should be understood that the C-terminal lysine is optional. In certain embodiments, the C-terminal lysine of an IgG sequence may be removed or replaced with a non-lysine amino acid, such as alanine, to further increase the serum half-life of the Fc fusion protein.

In certain embodiments, an Fc fusion protein comprises a human hinge, CH2 and CH3 domains, and may have the following amino acid sequence:

(SEQ ID NO: 66)
<u>DKTHTCPPC</u>PAPELLGGPSVFLFPPKPKDTLMISRTPEVTCVVVDVSHED

PEVKFNWYVDGVEVHNAKTKPREEQYNSTYRVVSVLTVLHQDWLNGKEYK

```
-continued
CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK,
``` wherein the core hinge sequence is underlined and the CH2 and CH3 regions are in regular text.

In certain embodiments, an Fc fusion protein comprises a CH2 and a CH3 region of a human IgG1 as shown below:

```
                                              (SEQ ID NO: 67)
VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK.
```

It should be understood that the glycine and lysine at the end of a CH3 domain are optional.

Fc fusion proteins may also comprise an Fc domain that is at least 50%, 60%, 75%, 80%, 85%, 90%, 95%, 96%, 97%, 98%, or 99% identical to SEQ ID NOs: 65-67. An Fc fusion protein may also comprise an Fc domain having at least 50, 100, or 150 contiguous amino acids of SEQ ID NOs: 65-67. Fc fusion proteins may also comprise an Fc domain having from 50-100, 50-150, or 100-150 contiguous amino acids of any one of SEQ ID NOs: 65-67. Fc fusion proteins may comprise an Fc domain comprising any one of SEQ ID NOs: 65-67 with from 1-5, 1-10, 1-15, 1-20, or 1-25 substitutions, e.g., conservative substitutions.

The Fc domain may be a naturally occurring Fc sequence, including natural allelic or splice variants. Alternatively, an Fc domain may be a non-naturally occurring Fc domain, e.g., a hybrid domain comprising a portion of an Fc domain from two or more different Ig isotypes, for example, an IgG2/IgG4 hybrid Fc domain. In exemplary embodiments, the Fc domain is derived from a human immunoglobulin molecule. Alternatively, the Fc domain may be a humanized or deimmunized version of an Fc domain from a non-human animal, including but not limited to mouse, rat, rabbit, camel, llama, dromedary and monkey.

In certain embodiments, the Fc domain is a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g., of the specific Fc region positions identified herein. Proteins comprising Fcs that are mutated to modify the biological activity of the Fc may be refolded as described herein. Exemplary Fc mutants are described, e.g., in WO97/34631; WO96/32478; U.S. Pat. Nos. 5,624,821; 5,648,260; 6,194,551; WO 94/29351; WO00/42072; U.S. Pat. Nos. 5,624,821; 6,277,375; 6,737,056; 6,194,551; 7,317,091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217; WO 05/092925; WO 06/020114; and Strohl, 2009, Current Opinion in Biotechnology 20:685-691; U.S. Pat. No. 6,277,375; Hinton et al., 2004, J. Biol. Chem. 279(8): 6213-6216; Hinton et al. 2006 Journal of Immunology 176:346-356; Dall Acqua et al. Journal of Immunology, 2002, 169:5171-5180, Dall'Acqua et al., 2006, Journal of Biological Chemistry 281:23514-23524; Yeung et al., 2010, J Immunol, 182:7663-7671; WO88/07054; WO88/07089; U.S. Pat. No. 6,277,375; WO99/051642; WO01/058957; WO2003/074679; WO2004/029207; U.S. Pat. No. 7,317,091 and WO2004/099249.

Exemplary variant Fcs are set forth as SEQ ID NOs: 68-86. In some aspects, an Fc fusion protein described herein comprises an Fc domain having at least 50, 100, or 150 contiguous amino acids of any one of SEQ ID NOs: 68-86. In other embodiments, an Fc fusion protein described herein comprises an Fc domain having from 50-100, 50-150, or 100-150 contiguous amino acids of SEQ ID NOs: 68-86. In yet other embodiments, an Fc fusion protein described herein comprises an Fc domain comprising SEQ ID NOs: 68-86 with from 1-5, 1-10, 1-15, 1-20, or 1-25 substitutions, e.g., conservative substitutions.

Fc fusion proteins may contain an immunoglobulin hinge region. The hinge region may be derived from antibodies belonging to any of the immunoglobulin classes, i.e. IgA, IgD, IgE, IgG, or IgM. In certain embodiments, the hinge region is derived from any of the IgG antibody subclasses, i.e. IgG1, IgG2, IgG3, and IgG4. In some embodiments, the hinge region may further include residues derived from the CH1 and CH2 regions that flank the core hinge sequence, as discussed further below.

In certain embodiments, a hinge contains a free cysteine residue that is capable of forming a disulfide bond with another monomer to form a dimer. The hinge sequence may naturally contain a cysteine residue, or may be engineered to contain one or more cysteine residues.

In certain embodiments, the Fc fusion proteins comprise a hinge region derived from a human IgG1. In some embodiments, the hinge region comprises the core hinge residues DKTHTCPPCPAPELLG (SEQ ID NO: 87) of IgG1, which corresponds to positions 221-236 according to EU numbering.

In certain embodiments, the hinge sequence may include substitutions that confer desirable pharmacokinetic, biophysical, and/or biological properties. Some exemplary hinge sequences include

```
                                              (SEQ ID NO: 88
          EPKSSDKTHTCPPCPAPELLGGPS;
``` core hinge region underlined),

```
                                              (SEQ ID NO: 89
          EPKSSDKTHTCPPCPAPELLGGSS;
``` core hinge region underlined),

EPKSSGSTHTCPPCPAPELLGGSS;  (SEQ ID NO: 90)

core hinge region underlined),

DKTHTCPPCPAPELLGGPS;  (SEQ ID NO: 91)

core hinge region underlined), and

DKTHTCPPCPAPELLGGSS,  (SEQ ID NO: 92)

core hinge region underlined). In one embodiment, the hinge sequence is a derivative of an IgG1 hinge comprising a P122S substitution (EU numbering 238) (e.g., the Proline residue at position 122 in SEQ ID NO: 22 is substituted with serine). The P122S substitution ablates Fc effector function and is exemplified by the hinges having any one of SEQ ID NOs: 25, 26, and 28. In another embodiment, the hinge sequence is a derivative of an IgG1 hinge comprising D104G and K105S substitutions (EU numbering 221-222). The D104G and K105S substitutions remove a potential cleavage site and therefore increase the protease resistance of the fusion molecule. A hinge having D104G and K105S substitutions is exemplified in SEQ ID NO: 26. In another embodiment, the hinge sequence is a derivative of an IgG1 hinge comprising a C103S substitution (EU numbering 220). The C103S substitution prevents improper cysteine bond formation in the absence of a light chain. Hinges having a C103S substitution are exemplified by SEQ ID NOs: 24-26.

Fc fusion proteins may comprise a hinge sequence that comprises, consists essentially of, or consists of an amino acid sequence that is at least 50%, 60%, 75%, 80%, 85%, 90%, 95%, 96%, 97%, 98%, or 99% to that of any hinge described herein, e.g., a hinge having SEQ ID NOs: 88-92, or comprises, consists essentially of, or consists of an amino acid sequence of any hinge described herein, e.g., one of SEQ ID NOs: 88-92. Fc fusion proteins may comprise a hinge portion comprises at least or at most 2, 5, 10, 12, 15, 18 or 20 contiguous amino acid residues from any of SEQ ID NOs: 88-92, or a sequence comprising from 1-5, 1-10, 1-15, 1-20, 2-5, 2-10, 2-15, 2-20, 5-10, 5-15, 5-20, 10-15, 10-20, or 15-20 contiguous amino acid residues from any of SEQ ID NOs: 88-92. In exemplary embodiments, the hinge sequence comprises a cysteine residue.

In certain embodiments, an Fc fusion protein does not comprise a hinge. For example, an Fc fusion protein may comprise an Fc domain linked to a heterologous protein, e.g., in the Fc-X or X-Fc format, without comprising a hinge or a core hinge. In one example, an Fc fusion protein does not comprise the sequence EPKSSDKTHTCPPCP (SEQ ID NO: 93) or a variant thereof.

In certain embodiments, an Fc fusion protein does not comprise a linker. For example, an Fc fusion protein may comprise an Fc domain that is linked directly to a heterologous protein, e.g., a $^{10}$Fn3 protein without an intervening sequence. In certain embodiments, there may be 1, 2, 3, 4 or 5 amino acids (e.g., from 1-5 or 1-10 amino acids) between the Fc domain and the heterologous protein. Such Fc fusion proteins may be X-Fc (the heterologous protein is linked at the N-terminus of the Fc) or Fc-X (the heterologous protein is linked at the C-terminus of the Fc) fusion proteins, wherein X is the heterologous protein, and wherein X and Fc are directly linked to each other.

In certain embodiments, an Fc fusion protein comprises neither a hinge nor a linker.

In certain embodiments, an Fc fusion protein is a dimer, wherein each monomer comprises a fusion protein (a homodimer). In certain embodiments, an Fc fusion protein is a heterodimer comprising, e.g., a monomer that comprises an Fc fusion protein and a monomer that comprises an Fc that is not linked to another moiety. The Fc portion of a monomer may comprise one or more amino acid modifications (or mutations) relative to a wild type Fc that favor dimer, e.g., heterodimer, formation with another Fc. For example, an Fc of a dimer may comprise a "hole" and the other Fc of the dimer may comprise a "bump" or "knob," as described, e.g., in WO96/027011; U.S. Pat. Nos. 5,731,168 and 5,821,333. Other modifications, such as electrostatic modifications may be used to enhance dimer formation. Exemplary modifications are described, e.g., in WO2007/110205; WO2009/089004 and WO2010/129304. Such changes are particularly useful for enhancing the association of two heterologous monomers to form a dimer, such as a dimer that comprises a monomer comprising an Fc fusion protein and a monomer comprising an Fc that is different from the Fc fusion protein, e.g., by the lack of a heterologous protein.

In certain embodiments, an Fc fusion protein comprises a monomer comprising the structure X-Fc and a monomer comprising the structure Fc-X (or Fc-Y). An Fc fusion protein may also comprise two monomers, each comprising the structure X-Fc-X (a "quad" structure), as used, e.g., in Examples 1-3. An Fc fusion protein may also comprise two monomers, each comprising the structure X-Fc-Y, or one monomer comprising the structure X-Fc-Y and a monomer comprising the structure Y-Fc-X. Each monomer may optionally comprise a linker and optionally comprise a hinge.

An Fc fusion protein may comprise a single chain Fc (scFc), wherein the first and the second Fc domain (or the first and the second hinge-Fc domains) are linked through a linker. In one embodiment, a scFc comprises in N- to C-terminal order a first CH2 domain, which first CH2 domain is linked to a first CH3 domain, which CH3 domain is linked to an Fc linker, which Fc linker is linked the a second CH2 domain, which second CH2 domain is linked to a second CH3 domain, wherein the first and the second CH2 and CH3 domains associate to form a dimeric Fc. An scFc may comprise in N- to C-terminal order a first hinge, which first hinge is linked to a first CH2 domain, which first CH2 domain is linked to a first CH3 domain, which first CH3 domain is linked to an Fc linker, which Fc linker is linked to a second hinge, which second hinge is linked to a second CH2 domain, which second CH2 domain is linked to a second CH3 domain, wherein the first and the second hinges, CH2 domains and CH3 domains associate to form a dimeric Fc. scFcs are described, e.g., in WO2008/131242, WO2008/143954 and WO2008/012543.

Exemplary Linkers for Connecting a Heterologous Protein to an Fc Moiety

Any linker may be used for covalently linking a heterologous protein, e.g., a fibronectin based scaffold moiety, to an Fc moiety, provided that the linker allows the fusion protein comprising the heterologous protein to properly fold and be biologically active. For example, the fusion protein should be able to bind efficiently to its target and may have a long half-life in serum relative to the heterologous protein that is not linked to an Fc. A linker is also preferably essentially not immunogenic and not reactive with other proteins (i.e., chemically inert).

A linker may be from 1-6, 1-10, 1-15, 1-20, 1-25, 1-30, 1-35, 1-40, 1-45, 1-50, 5-10, 5-15, 5-15, 5-20, 5-25, 5-30, 5-35, 5-40, 5-45, or 5-50 amino acids long.

Exemplary linkers may comprise, consist of, or consist essentially of GS linkers, e.g., $(GS)_1$, $(GS)_2$, $(GS)_3$, $(GS)_4$, $(GS)_5$, $(GS)_6$, $(GS)_7$, $(GS)_8$, $(GS)_9$ or $(GS)_{10}$. Linkers may also comprise, consist of, or consist essentially of $G_4S$ linkers, e.g., $(G_4S)_1$, $(G_4S)_2$, $(G_4S)_3$, $(G_4S)_4$ or $(G_4S)_5$. Additional exemplary linkers are provided in WO2012/142515.

Exemplary Fc Fusion Proteins that May be Refolded

Fusion proteins comprising a heterologous moiety X, e.g., $^{10}$Fn3, and an Fc moiety are collectively referred to herein as X/Fc fusions regardless of whether they contain a linker or a hinge and regardless of orientation (the "/" indicates that it covers both orientations, i.e., where the Fc is N-terminal or where the Fc is C-terminal to X).

In certain embodiments, an Fc is linked directly to X, i.e., without one or more intervening amino acid (e.g., without a linker). In certain embodiment, an Fc is linked indirectly to X, i.e., with one or more intervening amino acids, e.g., a linker.

Exemplary fusion proteins are as follows, and as shown in the N- to C-terminal order:

X-hinge-CH2-CH3; X-linker-hinge-CH2-CH3; X—CH2-CH3; X-linker-CH2-CH3; hinge-CH2-CH3-X; hinge-CH2-CH3-linker-X; CH2-CH3-X; CH2-CH3-linker-X, wherein X is a heterologous protein, e.g., a $^{10}$Fn3 molecule binding a target of interest, relative to the Fc portion. In either orientation, the X/Fc fusion proteins described herein may further contain an N-terminal methionine and/or a leader sequence (e.g., for expression in mammalian cells). Other constructs comprise a second heterologous protein linked to the other terminus of the Fc, and it can be the same or different heterologous molecules that are linked to each end.

In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29; and (ii) an Fc moiety, e.g., comprising an amino acid sequence that is at least about 70%, 75%, 80%, 85%, 90%, 95%, 97%, 98%, or 99% identical to SEQ ID NO: 65-86, wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29; (ii) an Fc moiety, e.g., comprising an amino acid sequence that is at least about 70%, 75%, 80%, 85%, 90%, 95%, 97%, 98%, or 99% identical to SEQ ID NO: 65-86; and (iii) a linker that covalently links the fibronectin based scaffold moiety to the Fc moiety, wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29, (ii) an Fc moiety, e.g., comprising an amino acid sequence that is at least about 70%, 75%, 80%, 85%, 90%, 95%, 97%, 98%, or 99% identical to SEQ ID NO: 65-86; and (iii) a linker that covalently links the fibronectin based scaffold moiety to the Fc moiety, wherein the linker comprises 1-10 amino acids, such as 6 amino acids, and wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). Exemplary fibronectin based scaffold moieties linked to an Fc are disclosed in WO2012/142515.

Also provided herein are protein compositions, e.g., compositions comprising one or more protein in one of the solutions or buffers described herein. For example, provided herein are compositions comprising a protein comprising at least two cysteines (wherein, e.g., the protein is a dimer comprising one cysteine on each dimer) that form a disulfide bond under appropriate conditions, and water, wherein the composition does not comprise a significant amount of buffer or a denaturing agent and optionally does not comprise a reducing agent. Also provided herein are compositions comprising a suspension of denatured proteins, wherein at least some proteins comprise at least two cysteines that form a disulfide bond under appropriate conditions, and wherein the composition does not comprise a buffer or a denaturing agent and optionally does not comprise a reducing agent. Further provided herein are compositions comprising a protein comprising at least two cysteines that form a disulfide bond under appropriate conditions, and a solubilization buffer having a pH in the range of pH 10 to 13, wherein the composition does not comprise a denaturing agent and optionally does not comprise a reducing agent. Also provided are compositions comprising a protein comprising at least two cysteines that form a disulfide bond under appropriate conditions, and a refold buffer having a pH in the range of pH 9 to 11 and an oxidizing agent, wherein the composition does not comprise a reducing agent other than a reducing agent that part of an oxidizing agent that is present in the composition. The protein concentration in any of these compositions may be at least 20 mg/ml, 15 mg/ml, 10 mg/ml, 5 mg/ml or 1 mg/ml. The compositions may comprise at least 70%, 80%, 90%, 95%, 97%, 98% or 99% of the protein of interest, e.g., a fibronectin based scaffold moiety linked to an Fc, relative to the total amount (e.g., in mg/ml) of protein in the composition. In the composition comprising refold buffer, refolded protein may constitute at least 70%, 80%, 90%, 95%, 97%, 98% or 99% of the protein in the sample.

Protein Synthesis

Proteins that can be refolded as described herein may be synthesized according to any method known in the art. Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Purified proteins may be prepared by culturing suitable host/vector systems to express the recombinant proteins. Expressed proteins, e.g., fibronectin based scaffold proteins, may then be purified from culture media or cell extracts.

Proteins may be synthesized chemically, enzymatically or recombinantly. Proteins may also be produced using cell-free translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system). For chemical synthesis, see, e.g., the methods described in Solid Phase Peptide Synthesis, 2nd ed., 1984, The Pierce Chemical Co., Rockford, Ill.).

Codon usage may be selected so as to improve expression in a cell. Such codon usage will depend on the cell type selected. Specialized codon usage patterns have been developed for E. coli and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from prokaryotic, mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins may comprise a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence may be substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces alpha-factor leaders), or acid phosphatase leader, the C. albicans glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the fusion protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein.

The recombinant DNA can also include any type of protein tag sequence that may be useful for purifying the fusion proteins. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct may be introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Expression in bacterial cells may be conducted essentially as follows or with certain variations therein. DNA encoding a protein of interest, e.g., a $^{10}$Fn3/Fc protein, is inserted into the pET9d (EMD Bioscience, San Diego, Calif.) vector and are expressed in E. coli HMS174 cells. Twenty ml of an inoculum culture (generated from a single plated colony) is used to inoculate 1 liter of LB medium containing 50 μg/ml carbenicillin and 34 μg/ml chloromphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at ≥10,000 g at 4° C. Cell pellets are frozen at −80° C. The cell pellet is resuspended in 25 ml of lysis buffer (20 mM $NaH_2PO_4$, 0.5 M NaCl, 1x Complete Protease Inhibitor Cocktail-EDTA free (Roche), 1 mM PMSF, pH 7.4) using an Ultra-turrax homogenizer (IKA works) on ice. Cell lysis is achieved by high pressure homogenization (≥18,000 psi) using a Model M-110S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodiumphosphate/500 mM NaCl, pH7.4. The pellet may optionally be further washed with water, and suspended in a suspension solution as further described herein. Other methods are described in WO2012/142515.

Proteins may be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis. Methods for expressing fusion proteins in E. coli are also provided in WO2012/142515.

The purified protein may be 85%, 95%, 98% or 99% pure. Regardless of the exact numerical value of the purity, the protein may be sufficiently pure for use as a pharmaceutical product.

Exemplary Uses

In one aspect, the application provides proteins, e.g., fusion proteins, comprising a fibronectin based scaffold moiety, useful in the treatment of disorders. The diseases or disorders that may be treated will be dictated by the binding specificity of the fibronectin based scaffold moiety. As described herein, fibronectin based scaffold moieties may be designed to bind to any target of interest. Exemplary targets include, for example, TNF-alpha, VEGFR2, PCSK9, IL-23, EGFR and IGF1R. Merely as an example, fibronectin based scaffold moieties that bind to TNF-alpha may be used to treat autoimmune disorders such as rheumatoid arthritis, inflammatory bowel disease, psoriasis, and asthma. Fusion proteins described herein may also be used for treating cancer.

The application also provides methods for administering fusion proteins to a subject. In some embodiments, the subject is a human. In some embodiments, the fusion proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions, e.g., comprising fibronecting based scaffold moiety, that are essentially endotoxin or pyrogen free or have very low endotoxin or pyrogen levels.

SEQUENCES

WT $^{10}$Fn3 Domain:
VSDVPRDLEVVAATPTSLLISWDAPAVTVRYYRITYGETGGNSPVQEFTVP
GSKSTATISGLKPGVDYTITVYAVTGRGDSPASSKPISINYRTEIDKPSQ (SEQ ID NO: 1)

$^{10}$Fn3 Domain of SEQ ID NO: 1 (with D97E)
VSDVPRDLEVVAATPTSLLISWDAPAVTVRYYRITYGETGGNSPVQEFTVP
GSKSTATISGLKPGVDYTITVYAVTGRGDSPASSKPISINYRTEIEKPSQ (SEQ ID NO: 2)

WT $^{10}$Fn3 Domain Core Sequence version 1:
LEVVAATPTSLLISWDAPAVTVRYYRITYGETGGNSPVQEFTVPGSKSTAT
ISGLKPGVDYTITVYAVTGRGDSPASSKPISINY (SEQ ID NO: 3)

WT $^{10}$Fn3 Domain Core Sequence version 2:
EVVAATPTSLLISWDAPAVTVRYYRITYGETGGNSPVQEFTVPGSKSTATI
SGLKPGVDYTITVYAVTGRGDSPASSKPISINYRT (SEQ ID NO: 4)

WT $^{10}$Fn3 Domain Core Sequence version 3:
VSDVPRDLEVVAATPTSLLISWDAPAVTVRYYRITYGETGGNSPVQEFTVP
GSKSTATISGLKPGVDYTITVYAVTGRGDSPASSKPISINYRT (SEQ ID NO: 5)

WT $^{10}$Fn3 Domain Core Sequence version 4:
VSDVPRDLEVVAATPTSLLISWDAPAVTVRYYRITYGETGGNSPVQEFTVP
GSKSTATISGLKPGVDYTITVYAVTGRGDSPASSKPISINYRTE (SEQ ID NO: 6)

WT $^{10}$Fn3 Domain Core Sequence version 5:
VSDVPRDLEVVAATPTSLLISWDAPAVTVRYYRITYGETGGNSPVQEFTVP
GSKSTATISGLKPGVDYTITVYAVTGRGDSPASSKPISINYRTEI (SEQ ID NO: 7)

WT $^{10}$Fn3 Domain Core Sequence version 6:
VSDVPRDLEVVAATPTSLLISWDAPAVTVRYYRITYGETGGNSPVQEFTVP
GSKSTATISGLKPGVDYTITVYAVTGRGDSPASSKPISINYRTEID (SEQ ID NO: 8)

$^{10}$Fn3 Domain Core Sequence version 7 (version 6 with D97E):
VSDVPRDLEVVAATPTSLLISWDAPAVTVRYYRITYGETGGNSPVQEFTVP
GSKSTATISGLKPGVDYTITVYAVTGRGDSPASSKPISINYRTEIE (SEQ ID NO: 9)

WT $^{10}$Fn3 Domain Core Sequence version 8:
VSDVPRDLEVVAATPTSLLISWDAPAVTVRYYRITYGETGGNSPVQEFTVP
GSKSTATISGLKPGVDYTITVYAVTGRGDSPASSKPISINYRTEIDK (SEQ ID NO: 10)

$^{10}$Fn3 Domain Core Sequence version 9 (version 8 with D97E):
VSDVPRDLEVVAATPTSLLISWDAPAVTVRYYRITYGETGGNSPVQEFTVP
GSKSTATISGLKPGVDYTITVYAVTGRGDSPASSKPISINYRTEIEK (SEQ ID NO: 11)

WT $^{10}$Fn3 Domain Core Sequence version 10:
VSDVPRDLEVVAATPTSLLISWDAPAVTVRYYRITYGETGGNSPVQEFTVP
GSKSTATISGLKPGVDYTITVYAVTGRGDSPASSKPISINYRTEIDKP (SEQ ID NO: 12)

$^{10}$Fn3 Domain Core Sequence version 11 (version 10 with D97E):
VSDVPRDLEVVAATPTSLLISWDAPAVTVRYYRITYGETGGNSPVQEFTVP
GSKSTATISGLKPGVDYTITVYAVTGRGDSPASSKPISINYRTEIEKP (SEQ ID NO: 13)

| SEQUENCES |
| --- |

WT <sup>10</sup>Fn3 Domain Core Sequence version 12:
VSDVPRDLEVVAATPTSLLISWDAPAVTVRYYRITYGETGGNSPVQEFTVP
GSKSTATISGLKPGVDYTITVYAVTGRGDSPASSKPISINYRTEIDKPS (SEQ ID
NO: 14)

<sup>10</sup>Fn3 Domain Core Sequence version 13 (version 12 with D97E):
VSDVPRDLEVVAATPTSLLISWDAPAVTVRYYRITYGETGGNSPVQEFTVP
GSKSTATISGLKPGVDYTITVYAVTGRGDSPASSKPISINYRTEIEKPS (SEQ ID NO:
15)

WT <sup>10</sup>Fn3 Domain with D80E Substitution
VSDVPRDLEVVAATPTSLLISWDAPAVTVRYYRITYGETGGNSPVQEFTVP
GSKSTATISGLKPGVDYTITVYAVTGRGESPASSKPISINYRTEIDKPSQ (SEQ ID
NO: 16)

Degenerate WT <sup>10</sup>Fn3 Domain Core Sequence:
VSDVPRDLEVVAA(X)$_u$LLISW(X)$_v$YRITY(X)$_w$FTV(X)$_x$ATISGL(X)$_y$YTITVY
A(X)$_z$ISINYRT (SEQ ID NO: 17)

VSDVPRDLEVVAA(X)$_u$LLISW(X)$_v$YRITY(X)$_w$FTV(X)$_x$ATISGL(X)$_y$YTITVY
A(X)$_z$ISINYRTE (SEQ ID NO: 18)

VSDVPRDLEVVAA(X)$_u$LLISW(X)$_v$YRITY(X)$_w$FTV(X)$_x$ATISGL(X)$_y$YTITVY
A(X)$_z$ISINYRTEI (SEQ ID NO: 19)

VSDVPRDLEVVAA(X)$_u$LLISW(X)$_v$YRITY(X)$_w$FTV(X)$_x$ATISGL(X)$_y$YTITVY
A(X)$_z$ISINYRTEID (SEQ ID NO: 20)

VSDVPRDLEVVAA(X)$_u$LLISW(X)$_v$YRITY(X)$_w$FTV(X)$_x$ATISGL(X)$_y$YTITVY
A(X)$_z$ISINYRTEIE (SEQ ID NO: 21)

VSDVPRDLEVVAA(X)$_u$LLISW(X)$_v$YRITY(X)$_w$FTV(X)$_x$ATISGL(X)$_y$YTITVY
A(X)$_z$ISINYRTEIDK (SEQ ID NO: 22)

VSDVPRDLEVVAA(X)$_u$LLISW(X)$_v$YRITY(X)$_w$FTV(X)$_x$ATISGL(X)$_y$YTITVY
A(X)$_z$ISINYRTEIEK (SEQ ID NO: 23)

VSDVPRDLEVVAA(X)$_u$LLISW(X)$_v$YRITY(X)$_w$FTV(X)$_x$ATISGL(X)$_y$YTITVY
A(X)$_z$ISINYRTEIDKP (SEQ ID NO: 24)

VSDVPRDLEVVAA(X)$_u$LLISW(X)$_v$YRITY(X)$_w$FTV(X)$_x$ATISGL(X)$_y$YTITVY
A(X)$_z$ISINYRTEIEKP (SEQ ID NO: 25)

VSDVPRDLEVVAA(X)$_u$LLISW(X)$_v$YRITY(X)$_w$FTV(X)$_x$ATISGL(X)$_y$YTITVY
A(X)$_z$ISINYRTEIDKPS (SEQ ID NO: 26)

VSDVPRDLEVVAA(X)$_u$LLISW(X)$_v$YRITY(X)$_w$FTV(X)$_x$ATISGL(X)$_y$YTITVY
A(X)$_z$ISINYRTEIEKPS (SEQ ID NO: 27)

VSDVPRDLEVVAA(X)$_u$LLISW(X)$_v$YRITY(X)$_w$FTV(X)$_x$ATISGL(X)$_y$YTITVY
A(X)$_z$ISINYRTEIDKPSQ (SEQ ID NO: 28)

VSDVPRDLEVVAA(X)uLLISW(X)$_v$YRITY(X)$_w$FTV(X)$_x$ATISGL(X)$_y$YTITVY
A(X)$_z$ISINYRTEIEKPSQ (SEQ ID NO: 29)

MGVSDVPRDL (SEQ ID NO: 30)

GVSDVPRDL (SEQ ID NO: 31)

X$_n$SDVPRDL (SEQ ID NO: 32)

X$_n$DVPRDL (SEQ ID NO: 33)

X$_n$VPRDL (SEQ ID NO: 34)

X$_n$PRDL (SEQ ID NO: 35)

X$_n$RDL (SEQ ID NO: 36)

X$_n$DL (SEQ ID NO: 37)

MASTSG (SEQ ID NO: 38)

EIEK (SEQ ID NO: 39)

EGSGC (SEQ ID NO: 40)

| SEQUENCES |
|---|
| EIEKPCQ (SEQ ID NO: 41) |
| EIEKPSQ (SEQ ID NO: 42) |
| EIEKP (SEQ ID NO: 43) |
| EIEKPS (SEQ ID NO: 44) |
| EIEKPC (SEQ ID NO: 45) |
| HHEHHE (SEQ ID NO: 46) |
| EIDK (SEQ ID NO: 47) |
| EIDKPCQ (SEQ ID NO: 48) |
| EIDKPSQ (SEQ ID NO: 49) |
| MPAPTDLRFTNETPSSLLISWTPPRVQITGYBRYGPVGSDGRVKEFTVPPS VSSATITGLKPGTEYTISVIALKDNQESEPLRGRVTTGG (FibconB; SEQ ID NO: 50) |
| TPSS (SEQ ID NO: 51) |
| TPPRVQI (SEQ ID NO: 52) |
| VGSDGR (SEQ ID NO: 53) |
| PSVS (SEQ ID NO: 54) |
| GLKPG (SEQ ID NO: 55) |
| KDNQESEP (SEQ ID NO: 56) |
| LDAPTDLQVTNVTDTSITVSWTPPSATITGYRITYTPSNGPGEPKELTVPPS STSVTITGITPGVEYVVSVYALKDNQESPPLVGTCTT (SEQ ID NO: 57) |
| LPAPKNLVVSEVTEDSLRLSWTAPDAAFDSFLIQYQESEKVGEAINLTVPG SERSYDLTGLKPGTEYTVSIYGVKGGHRSNPLSAEFTT (SEQ ID NO: 58) |
| TEDS (SEQ ID NO: 59) |
| TAPDAAF (SEQ ID NO: 60) |
| SEKVGE (SEQ ID NO: 61) |
| GSER (SEQ ID NO: 62) |
| GLKPG (SEQ ID NO: 63) |
| KGGHRSN (SEQ ID NO: 64) |
| ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSL SLSPGK (SEQ ID NO: 65) |
| DKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMHEALH NHYTQKSLSLSPGK (SEQ ID NO: 66) |
| VFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK (SEQ ID NO: 67) |
| EPRSSDKTHTCPPCPAPEAEGAPSVFLFPPKPKDTLMISRTPEVTCVVVDVS HEDPEVKFNWYVDGVEVHNAKTKPREEQYNSTYRVVSVLTVLHQDWLNGKEY KCKVSNKALPSSIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVMH EALHNHYTQKSLSLSPGK (SEQ ID NO: 68) |

| SEQUENCES |
| --- |

EPKSSDKTHTCPPCPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 69)

EPKSSDKTHTCPPCPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPG (SEQ ID NO: 70)

EPKSCDKTHTCPPCPAPELLGGPSVFLFPPKPKDTLMISRTPEVTCVVVDVS
HEDPEVKFNWYVDGVEVHNAKTKPREEQYQSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 71)

EPRSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 72)

DKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALH
NHYTQKSLSLSPGK (SEQ ID NO: 73)

EPKSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 74)

EPKSSDKTHTCPPCPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 75)

EPKSSDKTHTSPPSPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 76)

EPKSSDKTHTSPPSPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLGSKLTVDKSRWQQGNVFSCSVMH
EALHNHYTQKSLSLSPGK (SEQ ID NO: 77)

EPKSSDKTHTSPPSPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLGSKLTVDKSRWQQGNVFSCSVMH
EALHNHYTQKSLSLSPGK (SEQ ID NO: 78)

ESKYGPPCPPCPAPEFLGGPSVFLFPPKPKDTLMISRTPEVTCVVVDVSQED
PEVKFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLGK (SEQ ID NO: 79)

EPKSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVM
HEALHNHYTQKSLSLSLGK (SEQ ID NO: 80)

EPKSSDKTHTCPPCPAPELLGGPSVFLAPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 81)

-continued

SEQUENCES

EPKSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNAYTQKSLSLSPGK (SEQ ID NO: 82)

EPKSSDKTHTCPPCPAPEAEGAPSVFLFPPKPKDTLMISRTPEVTCVVVDVS
HEDPEVKFNWYVDGVEVHNAKTKPREEQYQSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMH
EALHNHYTQKSLSLSPGK (SEQ ID NO: 83)

EPKSSDKTHTSPPSPAPEAEGAPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPSSIEKTISKAKGQPREPQVYTLPPSRDELTKNQVSLTCLVKGFYPS
DIAVEWESNGQPENNYKTTPPVLDSDGSFALGSKLTVDKSRWQQGNVESCSVMH
EALHNHYTQKSLSLSPGK (SEQ ID NO: 84)

EPKSSDKTHTSPPSPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPS
DIAVEWESNGQPENNYKTTPPVLDSDGSFALGSKLTVDKSRWQQGNVESCSVMH
EALHNHYTQKSLSLSPGK (SEQ ID NO: 85)

EPKSSDKTHTCPPCPAPEAGGGPSVFLEPPKPKDTLMISRTPEVTCVVVDV
SHEDPEVKFNWYVDGVEVHNAKTKPREEQYNSTYRVVSVLTVLHQDWLNGKE
YKCKVSNKALPASIEKTISKAKGQPREPQVYTLPPSRDELTKNQVSLTCLVKGFYP
SDIAVEWESNGQPENNYKTTPPVLDSDGSFELYSKLTVDKSRWQQGNVESCSVM
HEALHNHYTQKSLSLSPGK (SEQ ID NO: 86)

DKTHTCPPCPAPELLG (SEQ ID NO: 87)

EPKSSDKTHTCPPCPAPELLGGPS (SEQ ID NO: 88)

EPKSSDKTHTCPPCPAPELLGGSS (SEQ ID NO: 89)

EPKSSGSTHTCPPCPAPELLGGSS (SEQ ID NO: 90)

DKTHTCPPCPAPELLGGPS (SEQ ID NO: 91)

DKTHTCPPCPAPELLGGSS (SEQ ID NO: 92)

EPKSSDKTHTCPPCP (SEQ ID NO: 93)

The following representative Examples contain additional information, exemplification and guidance which can be adapted to the practice of this invention in its various embodiments and the equivalents thereof. These examples are intended to help illustrate the invention, and are not intended to, nor should they be construed to, limit its scope.

EXAMPLES

Example 1: High-Throughput Screening of Buffer Conditions for Refolding Denatured Proteins In order to identify effective refolding conditions for $^{10}$Fn3/Fc fusion proteins produced in *E. coli*, an automated liquid handling platform was used to execute protein refolding by dilution in triplicate in 96-well plates.

The biomass of a $^{10}$Fn3/Fc protein was produced in a 10 L fermentor. The biomass was harvested and the IBs were recovered and washed by centrifugation before being frozen.

The screening study looked at protein concentration, resolubilization buffer, refold pH, temperature, aggregation suppressing excipients, and redox excipients. JMP Design of Experiments (DoE) software was used to design the screening study and analyze data. Data were gathered using a plate reader and SE-HPLC. The data suggested a resolubilization buffer around pH 8 with Guanidine and a refold buffer with Arginine to suppress aggregation, and a Glutathione redox system, around pH 10, favored formation of soluble protein. In addition, these conditions showed protein around the correct molecular weight in solution, indicating disulfide bond formation, required to form the $^{10}$Fn3/Fc homodimer.

Scale up of the dilution refold to 50 mL, 100 mL and 200 mL final refold volumes using the above-identified conditions were performed using a calibrated pump and mixing. A variable and heavy precipitation event was observed in all cases and a low recovery of protein was observed. Only around 10 to 20% of the protein was recovered in solution and found to be at the appropriate molecular weight. For a subset of the bench scale dilution refolds, a majority of the protein recovered in solution was found to be at a smaller molecular weight corresponding to $^{10}$Fn3/Fc monomer and indicating that the disulfide bonds did not form. With these data, it was determined that alternative methods of refolding $^{10}$Fn3/Fc molecules should be evaluated.

Example 2: Refolding of a 10Fn3/Fc Protein with TFF

This example describes the use of tangential flow filtration (TFF) as a method of buffer exchanging for refolding denatured $^{10}$Fn3/Fc proteins that are in the form of inclusion bodies (IBs). The buffer conditions for the TFF were determined by the original high throughput screening experiments. The $^{10}$Fn3/Fc protein used in this example had a quad structure, i.e., it comprised two monomers, each monomer consisting of an Fc (comprising a hinge, CH2 and CH3 domains) to which two identical $^{10}$Fn3 molecules binding a specific target protein are linked, one at its N-terminus and one at its C-terminus.

IBs were washed by resuspending them twice in a buffer containing a detergent (1% Triton X-100) and twice in RODI water, spinning down the IBs and pouring off the supernatant between each wash. Washed IBs (2.0 grams) were suspended 20% (w/v) (40 mL) in a solubilization buffer (50 mM Tris, 6 M Guanidine hydrochloride, 2 mM TCEP, pH 8.0). After approximately one hour, the protein solution was diluted 5-fold, with a buffer containing 50 mM Tris, 3.5 M Guanidine (final Guanidine concentration is 4 M), pH 8, filtered through a 0.2 μm membrane, and transferred to a TFF reservoir, which was set-up to allow gentle mixing.

The solubilized protein solution was held at constant volume and diafiltered with refold buffer. The TFF was operated with a TMP between 10 and 30 PSI with a 30 kDa NMWCO membrane, sized so that the operation takes between 3 and 6 hours. The protein solution was diafiltered with 3 diavolumes (i.e., 3 times 200 mL) of a refold buffer consisting of 50 mM Tris, 2 mM TCEP, 0.4 M Arginine, pH 10. Subsequently, the protein solution was diafiltered with 4 diavolumes (i.e., 4 times 200 mL) of a refold/oxidizing buffer consisting of 50 mM Tris, 1 mM oxidized glutathione, 0.2 mM reduced glutathione, 0.4 M Arginine, pH 10. The refolded protein solution was removed from the TFF reservoir. The protein solution was incubated overnight at room temperature. The protein was then purified according to standard methods.

The extent of dimer formation was evaluated during the process by reverse phase (RP) chromatography and SDS-PAGE. Briefly, a sample of between 2 and 50 μl of the refold step 1 reaction and between 2 and 50 l of refold step 2 reaction, both obtained at the end of each refold step, were loaded onto a reverse phase analytical chromatography column using an HPLC instrument. A gradient elution was performed and A280 was measured for the elution. A standard was used to make a calibration curve, which related peak area to concentration. This allowed the concentration of a particular protein of interest in the refold sample to be determined. Coupling the HPLC instrument to a mass spectrometer was used to confirm the identity of the protein for a given peak on the chromatogram.

The RP chromatograms are shown in FIGS. 3A and B and the stained SDS-PAGE gel is shown in FIG. 3C. As shown in these Figures, the protein obtained after the first refold step is mostly in the form of a monomer (see FIGS. 3A and C), whereas the protein obtained after the second refold step is mostly in the form of a dimer (see FIGS. 3B and C), indicating that the second refold step promoted disulfide bond formation, in particular, inter-chain disulfide bond formation. Identities of the peaks were confirmed by Mass Spectrometry. No precipitation was observed by visual inspection, increasing pressure in the TFF that would indicate membrane fouling, UV-VIS Spectroscopy, or mass balance of the protein solution from start to end.

LC/MS peptide map analysis showed that all disulfide bonds, including those in the hinge region, formed as expected, except that the level of CH3 open loops (unformed disulfide bond) was between 3 and 12%, compared to a level of between 1 and 3% in purified Fcs from human samples.

Figure 4:
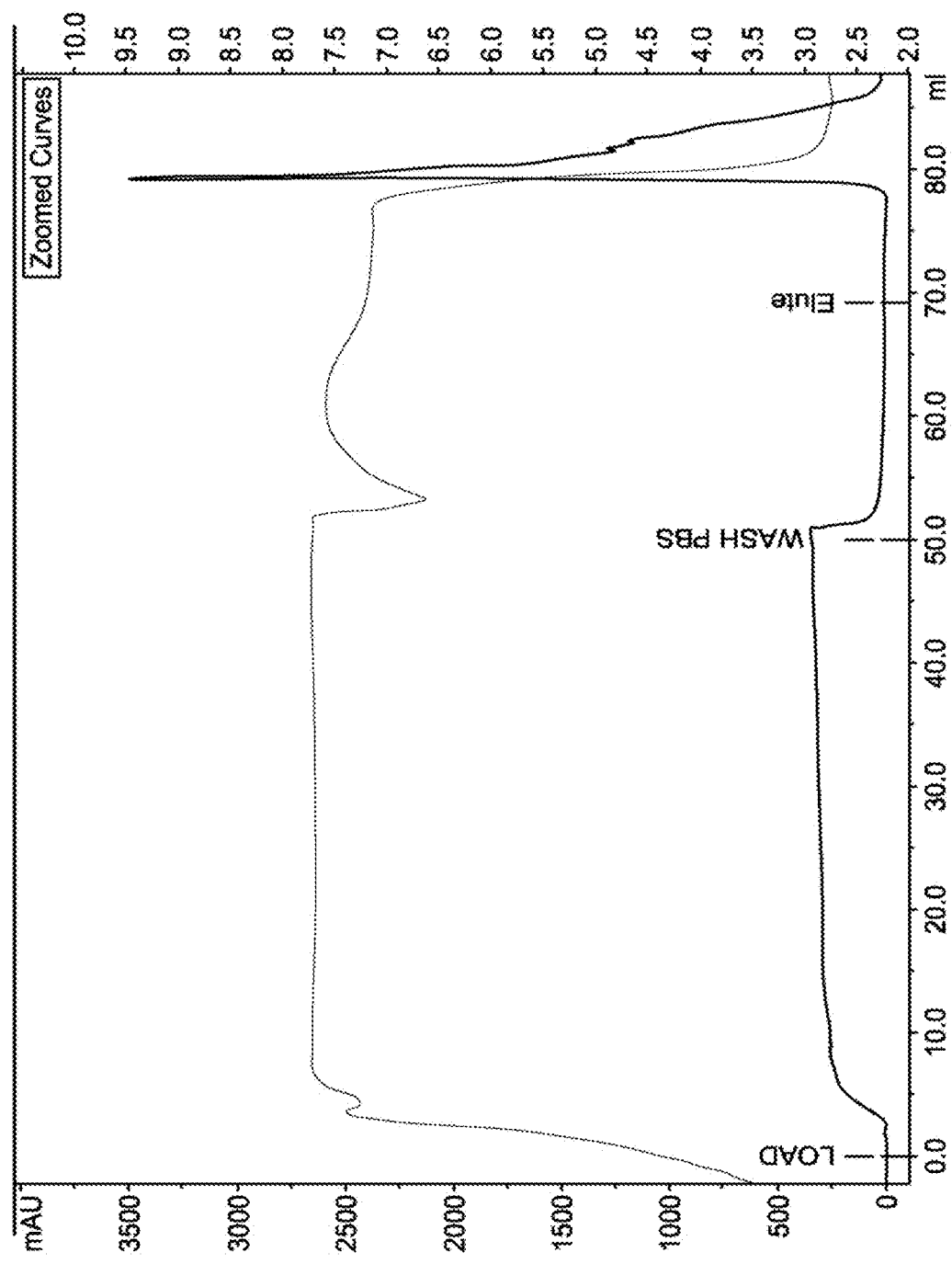
FIG. 4 shows a chromatogram of the refolded $^{10}$Fn3/Fc protein binding to a protein A affinity chromatography resin. The chromatography instrument has a UV detector and a pH meter inline and absorbance at 280 nm (A280) and pH are plotted against volume. The protein is loaded on the column between pH 7 and 9. The column is then chased and washed to remove unbound protein. The column is eluted with a low pH buffer, which disrupts the interaction between protein A and the Fc moiety. Any protein that binds to protein A is observed and collected in the A280 peak that is observed when the pH drops.

The protein was purified using common chromatography techniques and had expected in vitro and in vivo activity. For example, binding of the refolded $^{10}$Fn3/Fc protein to protein A was demonstrated as follows: the refolded protein sample was bound to a chromatography column packed with protein A resin at a pH between 7 and 9. The column was washed to remove unbound protein. A low pH buffer was used to elute the column by disrupting the association between the protein A on the resin and any functional Fc regions that had bound. An inline UV detector and pH meter were used to capture run data. The chromatogram of the elution, which is shown in FIG. 4, shows that the Fc region of the protein binds to Protein A and is then eluted with low pH, as expected for a properly folded $^{10}$Fn3/Fc protein. This result indicates that the Fc portion of the $^{10}$Fn3/Fc protein is at least sufficiently folded that it binds Protein A in an expected manner.

Analysis of the refolded protein by SE-HPLC, RP-HPLC/MS, and SDS-PAGE indicated that this method generated refolded protein with high efficiency, i.e., between 70 and 95%.

Thus, TFF can be used as a method of buffer exchanging to accomplish refolding of denatured $^{10}$Fn3/Fc proteins.

Example 3: Refolding of a 10Fn3/Fc Molecule with TFF in the Absence of a Reducing Agent This Example shows that denatured $^{10}$Fn3/Fc proteins can be refolded as described in Example 2, but without including a reducing agent in the solubilization or refold buffers, and at a 10-fold larger scale relative to the conditions in Example 2.

The experiment was conducted with the same protein as that in Example 2 and using the methods described in Example 2, except that it was performed without including a reducing agent in the solubilization and refold buffers, and at a 10-fold larger scale.

IBs were washed by resuspending them twice in a buffer containing a detergent (1% Triton X-100) and twice in RODI water, spinning down the IBs and pouring off the supernatant between each wash. Washed IBs (20 grams) were suspended 20% (w/v) (400 mL) in a solubilization buffer (50 mM Tris, 6 M Guanidine hydrochloride, pH 8.0). After approximately one hour, the protein solution was diluted 4-fold, with a buffer containing 3.5 M Guanidine (final Guanidine concentration is 4 M), filtered through a 0.2 m membrane, and transferred to a TFF reservoir, which was set-up to allow gentle mixing.

The solubilized protein solution was held at constant volume and diafiltered with refold buffer. The TFF was operated with a TMP between 10 and 30 PSI with a 30 kDa NMWCO membrane, sized so that the operation takes between 3 and 6 hours. The protein solution was diafiltered with 3 diavolumes (i.e., 3 times 1.6 L) of a refold buffer consisting of 50 mM Tris, 0.4 M Arginine, pH 10. Subsequently, the protein solution was diafiltered with 4 diavolumes (i.e., 4 times 1.6 L) of a refold/oxidizing buffer consisting of 50 mM Tris, 1 mM oxidized glutathione, 0.2 mM reduced glutathione, 0.4 M Arginine, pH 10. The refold protein solution was removed from the TFF reservoir. The protein solution was incubated overnight at room temperature. The protein was then purified according to standard methods.

The extent of dimer formation was evaluated during the process by reverse phase (RP) chromatography and SDS-PAGE as described in Example 2. The RP chromatograms are shown in FIGS. 5A and B and the stained SDS-PAGE gel is shown in FIG. 5C. As shown in these Figures, the protein obtained after the first refold step is mostly in the form of a monomer (see FIGS. 5A and C), whereas the protein obtained after the second refold step is mostly in the form of a dimer (see FIGS. 5B and C), indicating that the second refold step promoted disulfide bond formation, in particular, inter-chain disulfide bond formation. No precipitation was observed by visual inspection, increasing pressure in the TFF that would indicate membrane fouling, UV-VIS Spectroscopy, or mass balance of the protein solution from start to end.

LC/MS peptide map analysis showed that all disulfide bonds, including those in the hinge region, formed as expected, including the disulfide bond in the CH3 domains, with a level of CH3 open loop (unformed disulfide bond) between 1 and 3%, i.e., similar to that of purified Fcs from human samples. Thus, removing the reducing agent TCEP from all buffers was effective to reduce the level of CH3 open loops in the refolded proteins.

Figure 6:
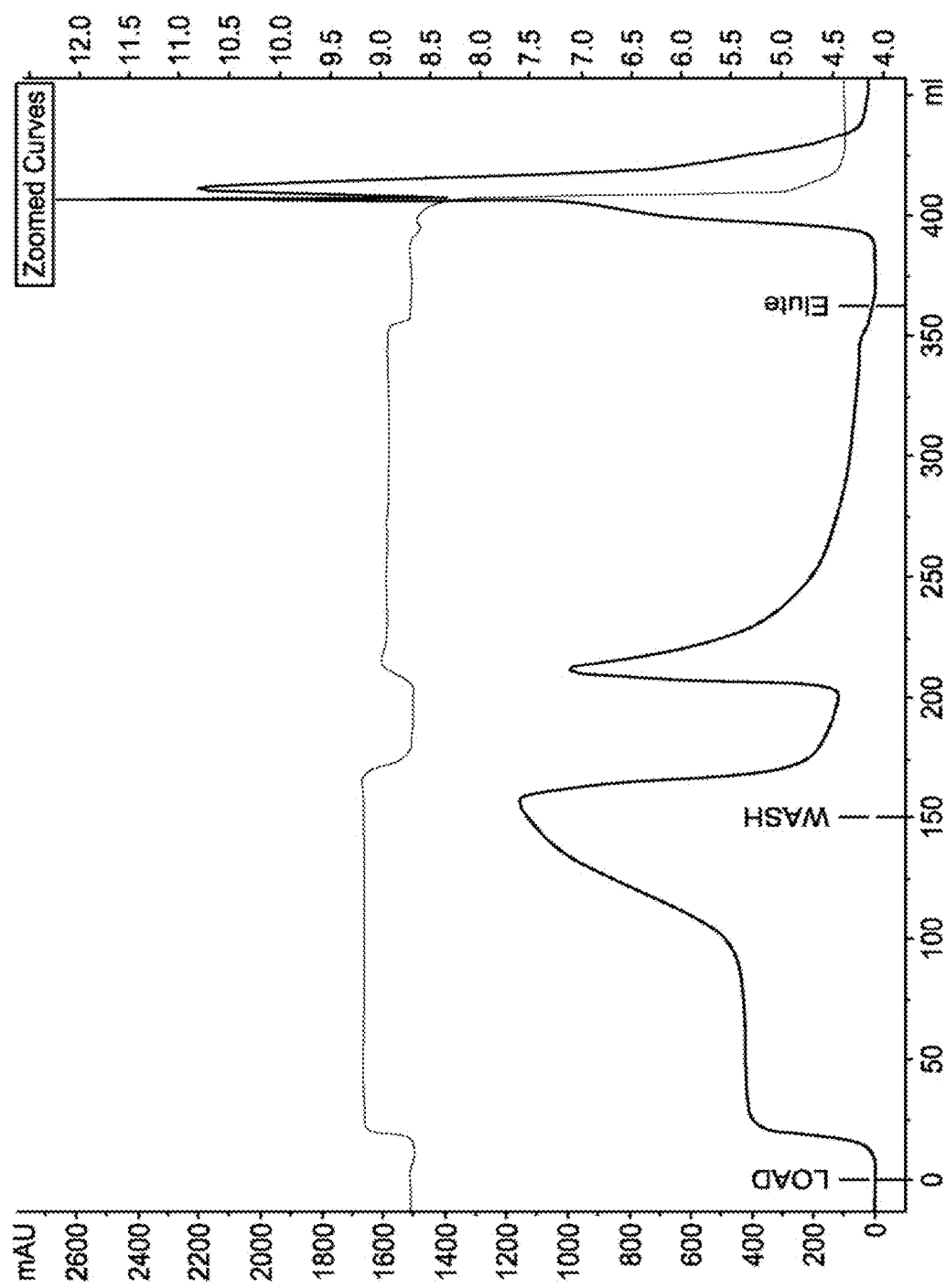
FIG. 6 shows a chromatogram of the refolded $^{10}$Fn3/Fc protein binding to a protein A affinity chromatography resin. The chromatography instrument has a UV detector and a pH meter inline and absorbance at 280 nm (A280) and pH are plotted against volume. The protein is loaded on the column between pH 7 and 9. The column is then chased and washed to remove unbound protein. The column is eluted with a low pH buffer, which disrupts the interaction between protein A and the Fc moiety. Any protein that binds to protein A is observed and collected in the A280 peak that is observed when the pH drops.

The protein was purified using common chromatography techniques and had expected in vitro and in vivo activity. For example, binding of the refolded $^{10}$Fn3/Fc protein to protein A was demonstrated as described in Example 2. Briefly, the refolded protein sample was bound to a chromatography column packed with protein A resin and the protein was eluted. The chromatogram of the elution, which is shown in FIG. 6, shows that the Fc region of the protein binds to Protein A and is then eluted with low pH, as expected for a properly folded $^{10}$Fn3/Fc protein. This result indicates that the Fc portion of the $^{10}$Fn3/Fc protein is at least sufficiently folded that it binds Protein A in an expected manner.

Figure 7B:
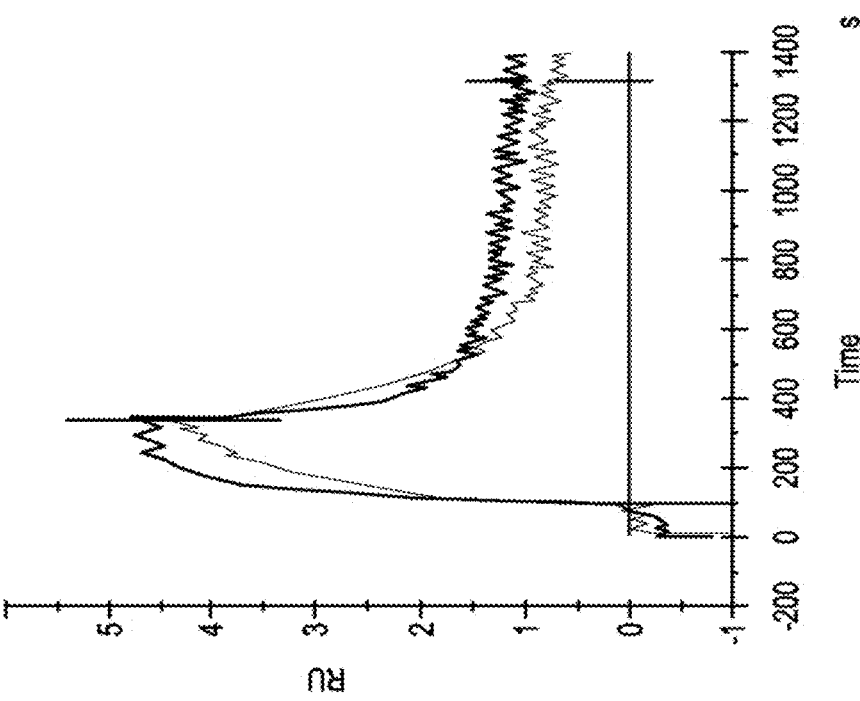
FIGS. 7A-B shows a sensagram from a surface plasmon resonance (SPR) experiment demonstrating binding of the $^{10}$Fn3 moiety to its target. An SPR chip with immobilized anti-human-Fc antibodies is used and the refolded $^{10}$Fn3/Fc protein is allowed to bind to the immobilized antibodies. Shortly after time 0 s, the target protein is applied to the chip and binding of the target protein to the $^{10}$Fn3 moiety generates a response. The target protein is no longer applied at the point indicated by the arrow. The dissociation between the $^{10}$Fn3 moiety and the target is observed as the response decreases. Panels A and B show the results when there is a high and low density of immobilized anti-human-Fc antibodies, respectively.
Figure 7A:
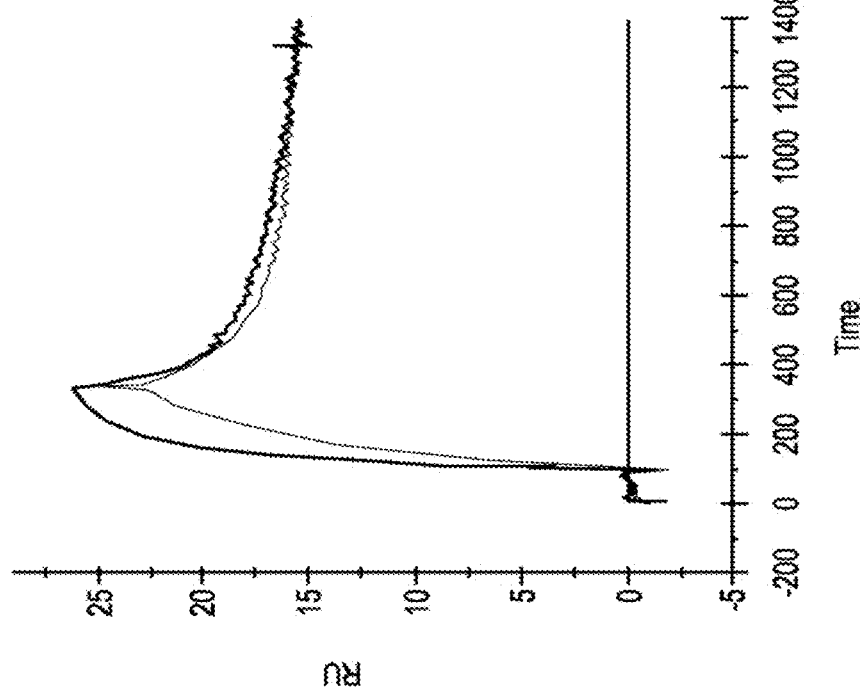

Binding of the $^{10}$Fn3/Fc protein to its target was also evaluated. The $^{10}$Fn3/Fc protein obtained as described in this Example was subjected to SPR in the presence of the target protein to which the $^{10}$Fn3 moiety binds. Anti-human-Fc antibodies were immobilized on a chip. The $^{10}$Fn3/Fc protein was applied in conditions that allowed binding of the $^{10}$Fn3/Fc protein to the immobilized antibodies. The target to which the $^{10}$Fn3 moiety binds was then applied and the SPR response was measured over time to detect changes. An initial response was detected and then target to which the $^{10}$Fn3 moiety binds was no longer applied, which allowed detection of the return of the response to baseline as target disassociated from the $^{10}$Fn3 moiety. FIG. 7 shows the resulting sensograms demonstrating binding of the refolded protein to its target, as expected. Thus, the $^{10}$Fn3 moiety of the $^{10}$Fn3/Fc protein is at least sufficiently folded that it binds to its target in an expected manner.

Figure 8:
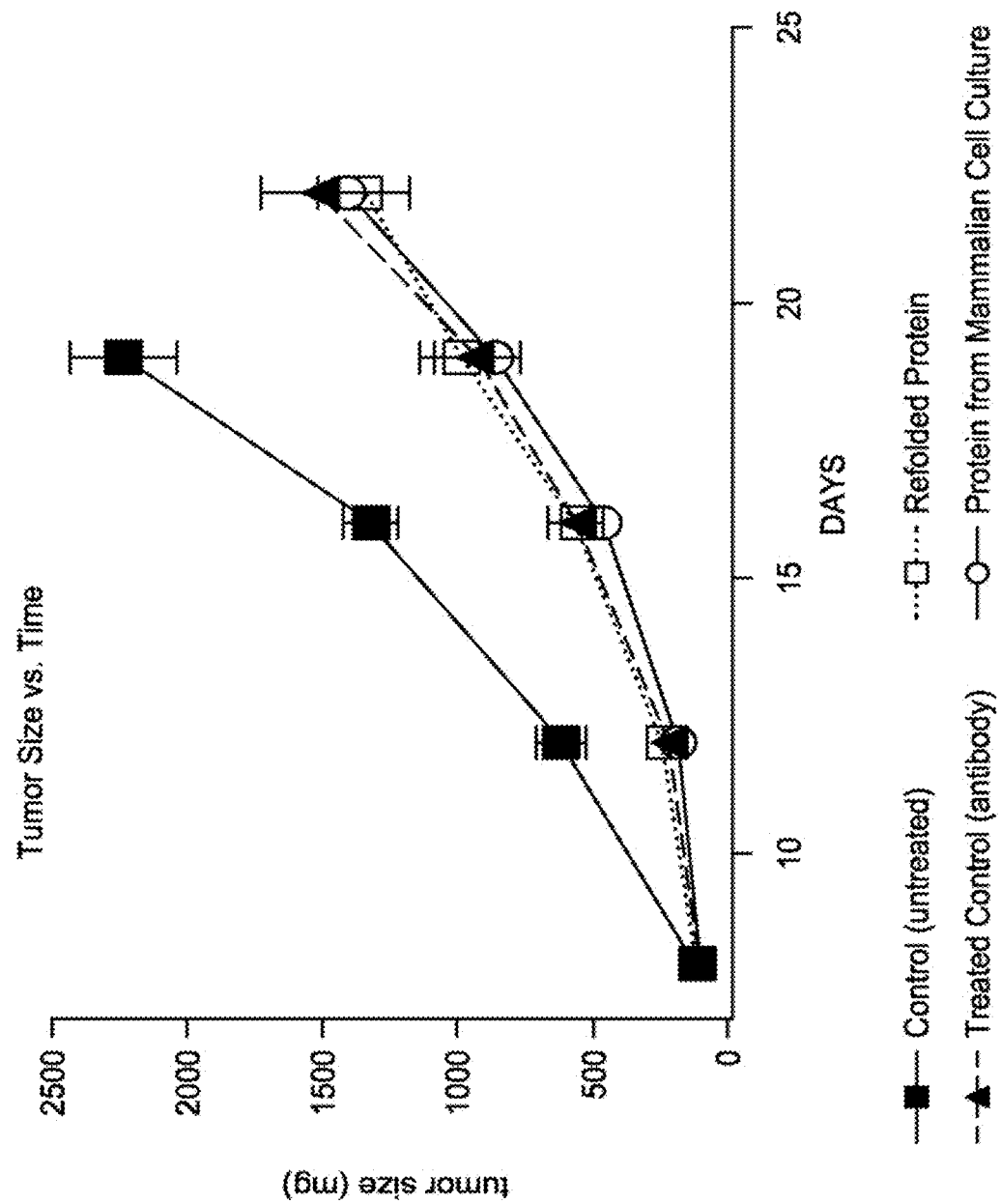
FIG. 8 shows a growth inhibition curve of tumor size as a function of time, following treatment with refolded $^{10}$Fn3/Fc protein; the same protein expressed in mammalian cell culture; a negative control and a positive control antibody.

The biological activity of the refolded $^{10}$Fn3/Fc protein was also evaluated and compared to that of the same protein produced in a mammalian cell culture. The $^{10}$Fn3/Fc protein from mammalian cell culture was produced by transient expression in HEK cells and purified by protein A chromatography, in a method as similar as possible to the $^{10}$Fn3/Fc protein produced in E. coli cells, except that the $^{10}$Fn3/Fc protein produced in mammalian cell culture was not resolubilized and refolded. FIG. 8 shows that the refolded $^{10}$Fn3/Fc protein inhibited the growth of tumor cells in a similar manner as the same protein expressed and purified from mammalian cell culture. These results indicate that the $^{10}$Fn3/Fc protein binds to its target and has biological activity, presumably because it has been refolded.

Analysis by SE-HPLC, RP-HPLC/MS, and SDS-PAGE indicate this method was successful at refolding the protein with high efficiency, between 70 and 95%.

Thus, denatured $^{10}$Fn3/Fc proteins can be refolded without including a reducing agent in the solubilization or refold buffers, and at a 10-fold larger scale relative to the conditions in Example 2.

Example 4: Refolding of Proteins at High Concentrations with TFF

This example shows that refolding of a denatured $^{10}$Fn3/Fc protein can be performed as described in Example 2, but at an elevated protein concentration.

The experiment was conducted with the same protein as that in Example 2 and using the methods described in Example 2, except that it was performed without a dilution step prior to TFF.

IBs were washed by resuspending them twice in a buffer containing a detergent (1% Triton X-100) and twice in RODI water, spinning down the IBs and pouring off the supernatant between each wash. Washed IBs (2.0 grams) were suspended 20% (w/v) (40 mL) in a solubilization buffer (50 mM Tris, 6 M Guanidine hycrochloride, pH 8.0). After approximately one hour, the protein solution was filtered through a 0.2 μm membrane, and transferred to a TFF reservoir, which was set-up to allow gentle mixing. Here, in contrast to Examples 2 and 3, the protein solution was not diluted prior to transferring into the TFF reservoir.

The solubilized protein solution was held at constant volume and diafiltered with refold buffer. The TFF was operated with a TMP between 10 and 30 PSI with a 30 kDa NMWCO membrane, sized so that the operation takes between 3 and 6 hours. The protein solution was diafiltered with 3 diavolumes (i.e., 3 times 40 mL) of a refold buffer consisting of 50 mM Tris, 0.4 M Arginine, pH 10. Subsequently, the protein solution was diafiltered with 5 diavolumes (i.e., 5 times 40 mL) of a refold buffer consisting of 50 mM Tris, 1 mM oxidized glutathione, 0.2 mM reduced glutathione, 0.4 M Arginine, pH 10. The refold protein solution was removed from the TFF reservoir. The protein solution was incubated overnight at room temperature. The protein was then purified according to standard methods.

The extent of dimer formation was evaluated during the process by reverse phase (RP) chromatography and SDS-PAGE as described in Example 2. The RP chromatograms are shown in FIGS. 9A and B and the stained SDS-PAGE gel is shown in FIG. 9C. As shown in these Figures, the protein obtained after the first refold step is mostly in the form of a monomer (see FIGS. 9A and C), whereas the protein obtained after the second refold step is mostly in the form of a dimer (see FIGS. 9B and C), indicating that the second refold step promoted disulfide bond formation, in particular, inter-chain disulfide bond formation. No precipitation was observed by visual inspection, increasing pressure in the TFF that would indicate membrane fouling, UV-VIS Spectroscopy, or mass balance of the protein solution from start to end.

LC/MS peptide map analysis showed that all disulfide bonds, including those in the hinge region, formed as expected.

Figure 10:
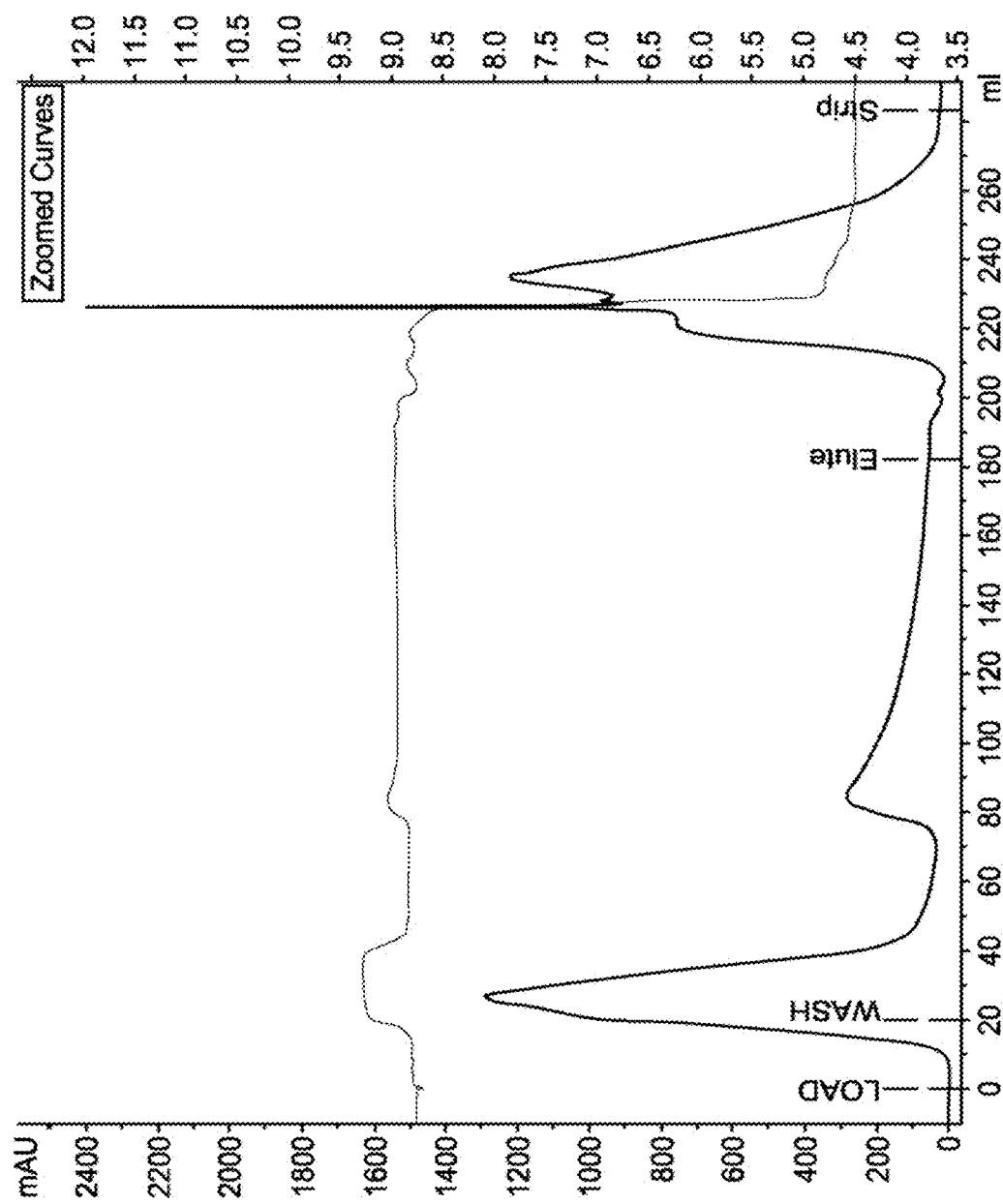
FIG. 10 shows a chromatogram of the refolded $^{10}$Fn3/Fc protein binding to a protein A affinity chromatography resin. The chromatography instrument has a UV detector and a pH meter inline and absorbance at 280 nm (A280) and pH are plotted against volume. The protein is loaded on the column between pH 7 and 9. The column is then chased and washed to remove unbound protein. The column is eluted with a low pH buffer, which disrupts the interaction between protein A and the Fc moiety. Any protein that binds to protein A is observed and collected in the A280 peak that is observed when the pH drops.

The protein was purified using common chromatography techniques and had expected in vitro and in vivo activity. For example, binding of the refolded $^{10}$Fn3/Fc protein to protein A was demonstrated as described in Example 2. Briefly, the refolded protein sample was bound to a chromatography column packed with protein A resin and the protein was eluted. The chromatogram of the elution, which is shown in FIG. 10, shows that the Fc region of the protein binds to Protein A and is then eluted with low pH, as expected for a properly folded $^{10}$Fn3/Fc protein. This result indicates that the Fc portion of the $^{10}$Fn3/Fc protein is at least sufficiently folded that it binds Protein A in an expected manner.

Binding of the $^{10}$Fn3/Fc protein to its target was evaluated as described in Example 3. Briefly, the $^{10}$Fn3/Fc protein obtained as described in this Example was subjected to SPR in the presence of the target protein to which the ¹⁰Fn3 moiety binds. FIG. 11 shows the resulting sensograms demonstrating binding of the refolded protein to its target, as expected. Thus, the ¹⁰Fn3 moiety of the ¹⁰Fn3/Fc protein is at least sufficiently folded that it binds to its target in an expected manner.

Analysis by SE-HPLC, RP-HPLC/MS, and SDS-PAGE indicated that this method was successful at refolding the protein with high efficiency, between 70 and 95%.

Thus, dilution before the TFF, following the initial solubilization, was found not to be necessary, allowing refolding to occur at a protein concentration of up to 10 g/L.

Example 5: Refolding of a 10Fn3-Fc Protein with TFF

This example shows that a denatured ¹⁰Fn3/Fc protein having a structure and a ¹⁰Fn3 that is different from that of the ¹⁰Fn3/Fc proteins used in the previous examples, can also be refolded using TFF as a method of buffer exchanging.

A ¹⁰Fn3/Fc molecule having the ¹⁰Fn3 molecule linked to the N-terminus of the Fc ("¹⁰Fn3-Fc") and having the following amino acid sequence was used (the ¹⁰Fn3 sequence is shown in italics):

(SEQ ID NO: 94)
MG*VSDVPRDLEVVAATPTSLLISWVPPSDDYGYYRITYGETGGNSPVQEF*

*TVPIGKGTATISGLKPGVDYTITVYAVEFPWPHAGYYHRPISINYRTEIE*

PKSSGSTHTCPPCPAPELLGGSSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK.

The ¹⁰Fn3 molecule has a different amino acid sequence and binds to a different target protein relative to the ¹⁰Fn3 molecule used in the previous examples.

The ¹⁰Fn3/Fc protein was expressed in *E. coli* and the IBs were collected. IBs were washed by resuspending them twice in a buffer containing a detergent (1% Triton X-100) and twice in RODI water, spinning down the IBs and pouring off the supernatant between each wash. Washed IBs (20 grams) were suspended 20% (w/v) (400 mL) in a solubilization buffer (50 mM Tris, 6 M Guanidine hydrochloride, 5 mM TCEP, pH 8.0). After approximately one hour, the protein solution was diluted 4-fold, with a buffer containing 3.5 M Guanidine (final Guanidine concentration is 4 M), filtered through a 0.2 m membrane, and transferred to a TFF reservoir, which was set-up to allow gentle mixing.

The solubilized protein solution was held at constant volume and diafiltered with refold buffer. The TFF was operated with a transmembrane pressure (TMP) between 10 and 30 PSI with a 30 kDa NMWCO membrane, sized so that the operation takes between 3 and 6 hours. The protein solution was diafiltered with 3 diavolumes of a refold buffer consisting of 50 mM Tris, 0.4 M Arginine, 5 mM TCEP, pH 10 (refold step 1). Subsequently, the protein solution was diafiltered with 4 diavolumes of a refold buffer consisting of 50 mM Tris, 1 mM oxidized glutathione, 0.2 mM reduced glutathione, 0.4 M Arginine, pH 10 (refold step 2). The refold protein solution was removed from the TFF reservoir. The protein solution was incubated overnight at room temperature. The protein was then purified according to standard methods.

Figure 12:
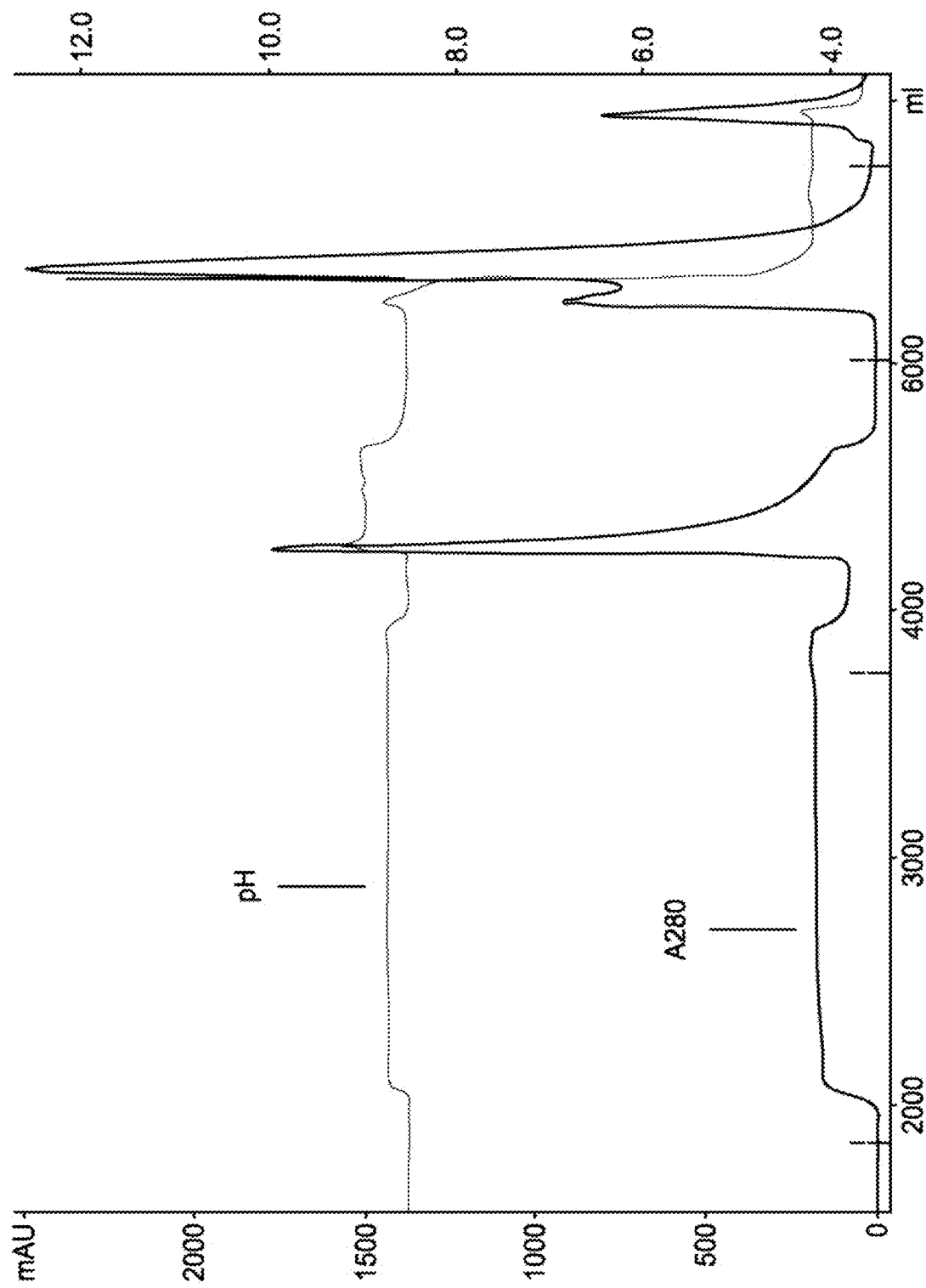
FIG. 12 shows a chromatogram of the refolded $^{10}$Fn3/Fc protein binding to a protein A affinity chromatography resin. The chromatography instrument has a UV detector and a pH meter inline and absorbance at 280 nm (A280) and pH are plotted against volume. The protein is loaded on the column between pH 7 and 9. The column is then chased and washed to remove unbound protein. The column is eluted with a low pH buffer, which disrupts the interaction between protein A and the Fc moiety. Any protein that binds to protein A is observed and collected in the A280 peak that is observed when the pH drops.

The extent of dimer formation was evaluated during the process by reverse phase (RP) chromatography and SDS-PAGE as described in Example 2. The RP chromatograms are shown in FIGS. 12A and B and the stained SDS-PAGE gel is shown in FIG. 12C. As shown in these Figures, the protein obtained after the first refold step is mostly in the form of a monomer (see FIGS. 12A and C), whereas the protein obtained after the second refold step is mostly in the form of a dimer (see FIGS. 12B and C), indicating that the second refold step promoted disulfide bond formation, in particular, inter-chain disulfide bond formation. No precipitation was observed by visual inspection, increasing pressure in the TFF that would indicate membrane fouling, UV-VIS Spectroscopy, or mass balance of the protein solution from start to end.

Figure 13:
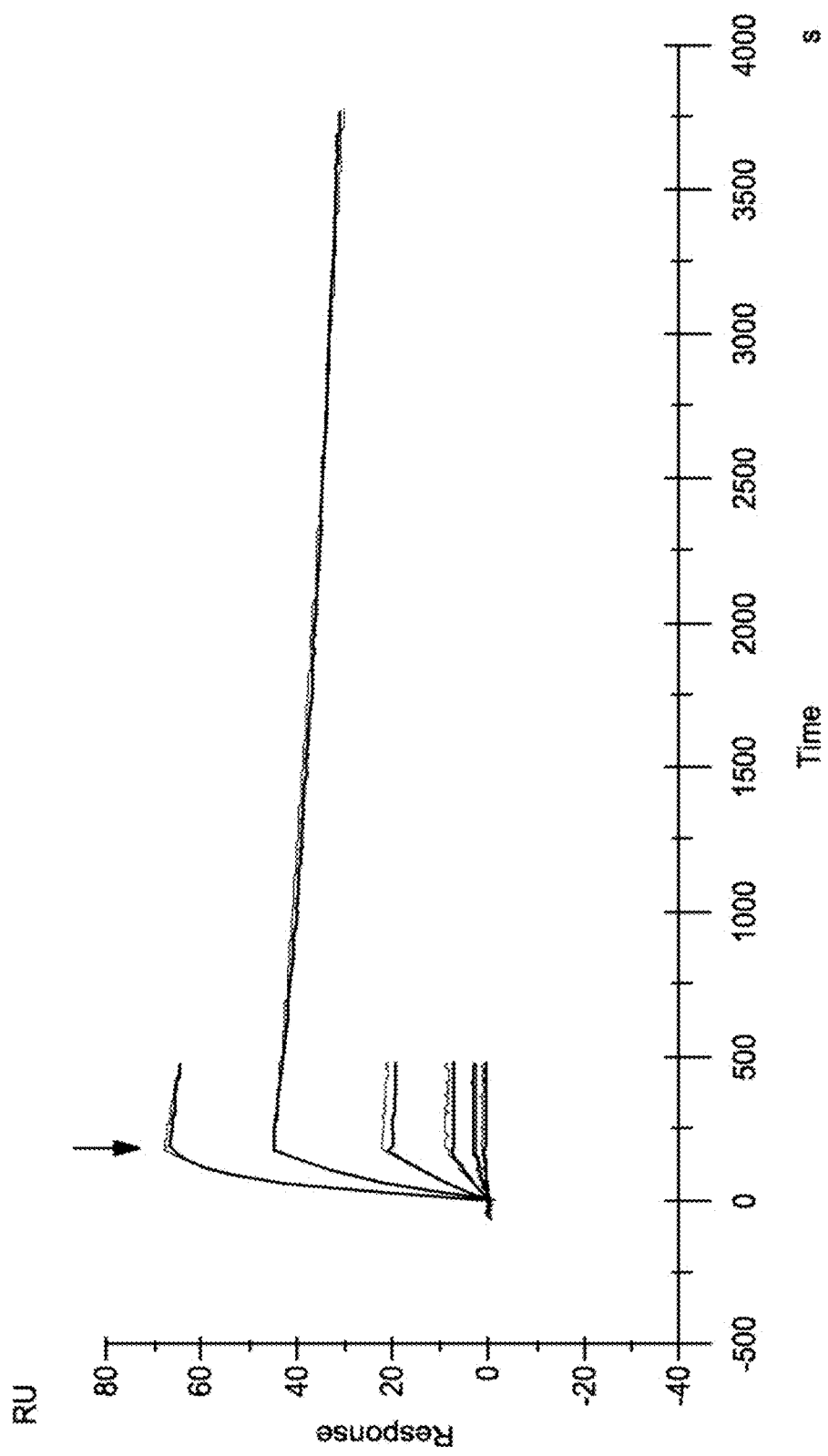
FIG. 13 shows a sensagram from a surface plasmon resonance (SPR) experiment demonstrating binding of the $^{10}$Fn3 moiety to its target. An SPR chip with immobilized anti-human-Fc antibodies is used and the refolded $^{10}$Fn3/Fc protein is allowed to bind to the immobilized antibodies. Shortly after time 0 s, the target protein is applied to the chip and binding of the target protein to the $^{10}$Fn3 moiety generates a response. The target protein is no longer applied at the point indicated by the arrow. The dissociation between the $^{10}$Fn3 moiety and the target is observed as the response decreases.

The protein was purified using common chromatography techniques and had expected in vitro and in vivo activity. For example, binding of the refolded ¹⁰Fn3/Fc protein to protein A was demonstrated as described in Example 2. Briefly, the refolded protein sample was bound to a chromatography column packed with protein A resin and the protein was eluted. The chromatogram of the elution, which is shown in FIG. 13, shows that the Fc region of the protein binds to Protein A and is then eluted with low pH, as expected for a properly folded ¹⁰Fn3/Fc protein. This result indicates that the Fc portion of the ¹⁰Fn3/Fc protein is at least sufficiently folded that it binds Protein A in an expected manner.

Binding of the ¹⁰Fn3/Fc protein to its target was evaluated as described in Example 3. Briefly, the ¹⁰Fn3/Fc protein obtained as described in this Example was subjected to SPR in the presence of the target protein to which the ¹⁰Fn3 moiety binds. FIG. 14 shows the resulting sensograms demonstrating binding of the refolded protein to its target, as expected. Thus, the ¹⁰Fn3 moiety of the ¹⁰Fn3/Fc protein is at least sufficiently folded that it binds to its target in an expected manner.

Thus, a denatured ¹⁰Fn3/Fc protein having the structure ¹⁰Fn3-Fc can be refolded using TFF as a method of buffer exchanging.

Example 6: Refolding of an Fc-¹⁰Fn3 Protein with TFF

This example shows that a denatured ¹⁰Fn3/Fc protein having a structure and a ¹⁰Fn3 that is different from that of the ¹⁰Fn3/Fc proteins used in the previous examples, can also be refolded using TFF as a method of buffer exchanging.

This example describes the use of TFF as a method of buffer exchanging to accomplish refolding of a denatured ¹⁰Fn3/Fc protein that is in the form of an IB and that is different from that in Example 1. Thus, this Example shows that the method is applicable to different types of ¹⁰Fn3/Fc proteins.

The ¹⁰Fn3/Fc protein used in this Example has the Fc portion (hinge-CH1-CH2 of wild type human IgG1) that is N-terminal to the ¹⁰Fn3 moiety (i.e., opposite orientation from the protein in Example 5) and the ¹⁰Fn3 molecule is different from, and binds to a different protein target, relative to that in Example 5. The Fc has the following amino acid sequence:

(SEQ ID NO: 95)
MADKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSP.

The $^{10}$Fn3/Fc protein was expressed in *E. coli* and IBs were collected. IBs were washed by resuspending them twice in a buffer containing a detergent (1% Triton X-100) and twice in RODI water, spinning down the IBs and pouring off the supernatant between each wash. Washed IBs (20 grams) were suspended 20% (w/v) (400 mL) in a solubilization buffer (50 mM Tris, 6 M Guanidine hydrochloride, 5 mM TCEP, pH 8.0). After approximately one hour, the protein solution was diluted 4-fold, with a buffer containing 3.5 M Guanidine (final Guanidine concentration is 4 M), filtered through a 0.2 m membrane, and transferred to a TFF reservoir, which was set-up to allow gentle mixing.

The solubilized protein solution was held at constant volume and diafiltered with refold buffer. The TFF was operated with a TMP between 10 and 30 PSI with a 30 kDa NMWCO membrane, sized so that the operation takes between 3 and 6 hours. The protein solution was diafiltered with 3 diavolumes of a refold buffer consisting of 50 mM Tris, 0.4 M Arginine, 5 mM TCEP, pH 10 (refold step 1). Subsequently, the protein solution was diafiltered with 4 diavolumes of a refold buffer consisting of 50 mM Tris, 1 mM oxidized glutathione, 0.2 mM reduced glutathione, 0.4 M Arginine, pH 10. The refold protein solution was removed from the TFF reservoir (refold step 2). The protein solution was incubated overnight at room temperature. The protein was then purified according to standard methods.

Figure 14A:
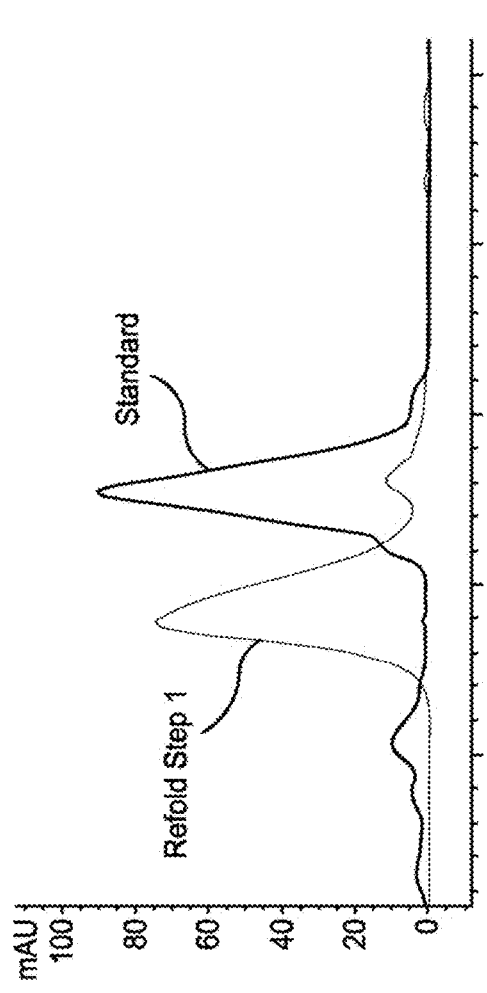
FIGS. 14A and B show that $^{10}$Fn3/Fc protein after refold step 1 is mostly in the form of a monomer (panel A), whereas the $^{10}$Fn3/Fc protein after refold step 2 is mostly in the form of a dimer, confirming that the protein was refolded. Panels A and B show the $^{10}$Fn3/Fc protein after refold steps 1 and 2, respectively, (peaks labeled "refold step 1" and "refold step 2") compared to the same refolded protein ("standard"), as visualized by RP-HPLC.
Figure 14B:
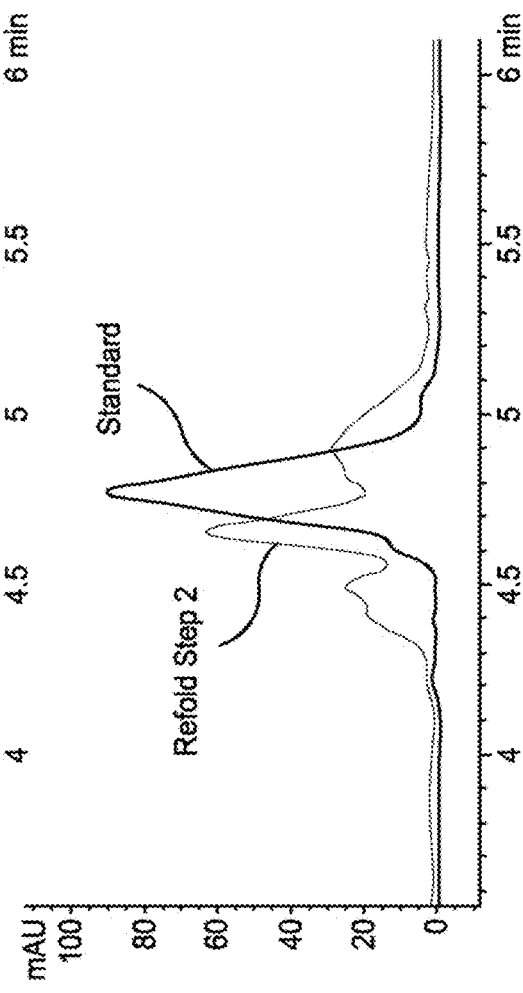

The extent of dimer formation was evaluated during the process by reverse phase (RP) chromatography and SDS-PAGE as described in Example 2. The RP chromatograms are shown in FIGS. 14A and B and the stained SDS-PAGE gel is shown in FIG. 14C. As shown in these Figures, the protein obtained after the first refold step is mostly in the form of a monomer (see FIGS. 14A and C), whereas the protein obtained after the second refold step is mostly in the form of a dimer (see FIGS. 14B and C), indicating that the second refold step promoted disulfide bond formation, in particular, inter-chain disulfide bond formation. No precipitation was observed by visual inspection, increasing pressure in the TFF that would indicate membrane fouling, UV-VIS Spectroscopy, or mass balance of the protein solution from start to end.

Figure 15:
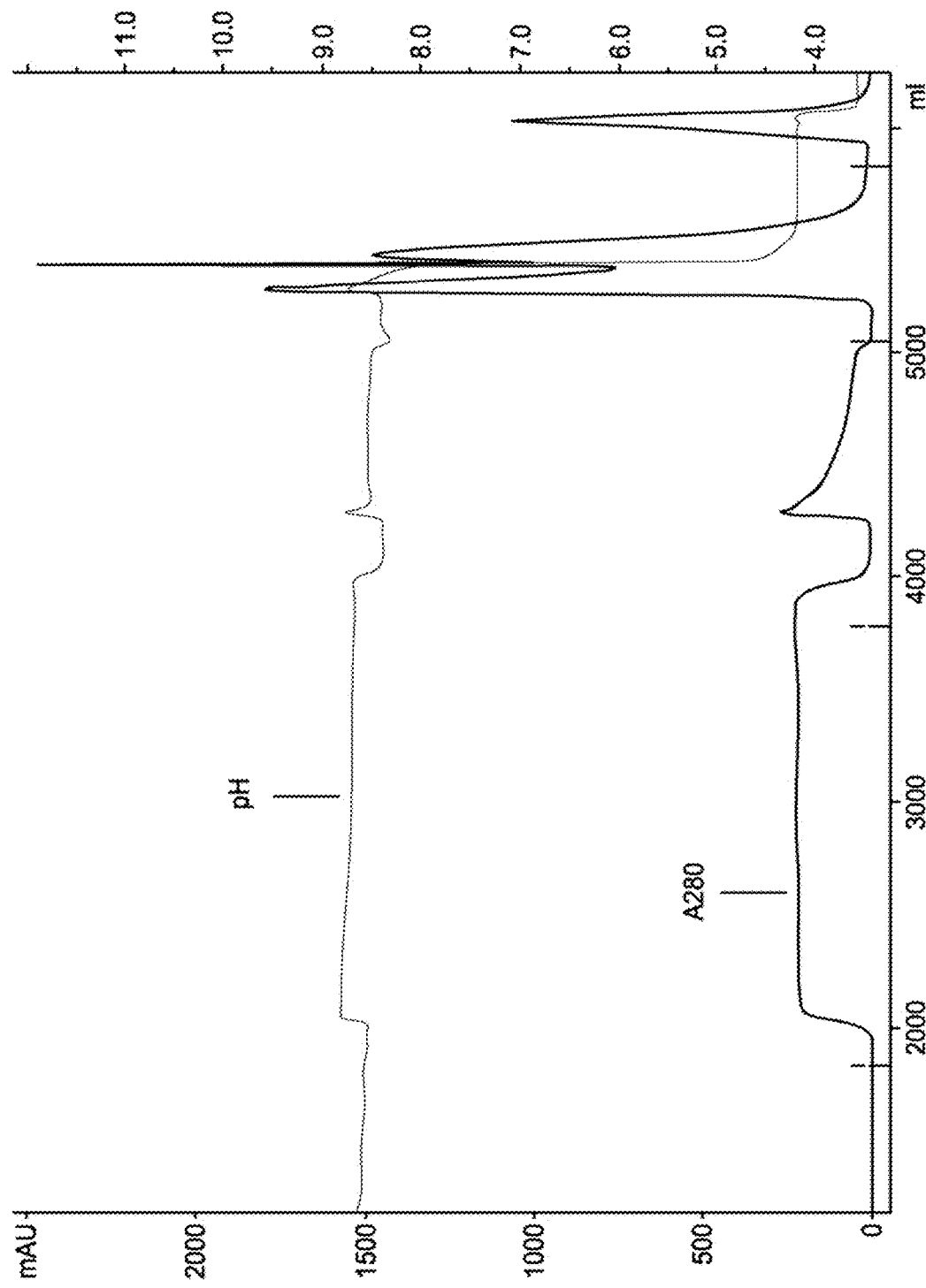
FIG. 15 shows a chromatogram of the refolded $^{10}$Fn3/Fc protein binding to a protein A affinity chromatography resin. The chromatography instrument has a UV detector and a pH meter inline and absorbance at 280 nm (A280) and pH are plotted against volume. The protein is loaded on the column between pH 7 and 9. The column is then chased and washed to remove unbound protein. The column is eluted with a low pH buffer, which disrupts the interaction between protein A and the Fc moiety. Any protein that binds to protein A is observed and collected in the A280 peak that is observed when the pH drops.

The protein was purified using common chromatography techniques and had expected in vitro and in vivo activity. For example, binding of the refolded $^{10}$Fn3/Fc protein to protein A was demonstrated as described in Example 2. Briefly, the refolded protein sample was bound to a chromatography column packed with protein A resin and the protein was eluted. The chromatogram of the elution, which is shown in FIG. 15, shows that the Fc region of the protein binds to Protein A and is then eluted with low pH, as expected for a properly folded $^{10}$Fn3/Fc protein. This result indicates that the Fc portion of the $^{10}$Fn3/Fc protein is at least sufficiently folded that it binds Protein A in an expected manner.

Thus, using TFF as a buffer exchange system for refolding denatured proteins is applicable to different $^{10}$Fn3/Fc proteins, regardless of whether the $^{10}$Fn3 molecule is linked to the N-terminus, C-terminus, or both, of the Fc, and regardless of the nature of the $^{10}$Fn3 molecule.

The entire disclosure of each document cited (including patents, patent applications, journal articles, abstracts, laboratory manuals, books, GENBANK® Accession numbers, SWISS-PROT® Accession numbers, or other disclosures) in the instant patent application, e.g., in the Background, Detailed Description, Brief Description of the Drawings, and Examples, is hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method for refolding a denatured protein, comprising
   (i) combining the denatured protein with a solubilization buffer that comprises a denaturing agent and has a pH in the range of 7 to 10, wherein the denaturing agent is guanidine or guanidinium, to obtain a first protein composition comprising solubilized denatured protein, wherein the denatured protein comprises a tenth fibronectin type III ($^{10}$Fn3) domain;
   (ii) diafiltering the first protein composition comprising solubilized denatured protein with 2-4 diavolumes of a refold buffer that comprises arginine and has a pH in the range of 9 to 11 to obtain a second protein composition comprising partially refolded protein; and
   (iii) incubating the second protein composition comprising partially refolded protein with a refold/oxidizing buffer that comprises arginine and glutathione and has a pH in the range of 9 to 11 to obtain a third protein composition comprising the protein in a refolded state, wherein the protein in a refolded state comprises at least one disulfide bond.

2. The method of claim 1, wherein incubating the second protein composition comprising partially refolded protein with a refold/oxidizing buffer comprises diafiltering the second protein composition with 2-6 diavolumes of a refold/oxidizing buffer.

3. The method of claim 1, wherein diafiltering with the refold buffer takes between 0.5 to 3 hours.

4. The method of claim 1, wherein the diafiltering with the refold/oxidizing buffer takes between 0.5 to 3 hours.

5. The method of claim 1, wherein the first composition comprising solubilized denatured protein is not diluted prior to diafiltering.

6. The method of claim 1, wherein the first composition comprising solubilized denatured protein is filtered prior to diafiltering.

7. The method of claim 1, wherein the third protein composition comprises 1-10 mg/ml of protein.

8. The method of claim 1, wherein the protein in a refolded state has an efficiency of recovery of at least about 70%.

9. The method of claim 1, wherein the denatured protein comprises an Fc region.

10. The method of claim 1, wherein the solubilization buffer, refold buffer, and/or refold/oxidizing buffer comprises Tris.

* * * * *

UNITED STATES PATENT AND TRADEMARK OFFICE
CERTIFICATE OF CORRECTION

PATENT NO. : 11,053,278 B2  
APPLICATION NO. : 16/211094  
DATED : July 6, 2021  
INVENTOR(S) : Benjamin C. Blum et al.

Page 1 of 1

It is certified that error appears in the above-identified patent and that said Letters Patent is hereby corrected as shown below:

On the Title Page

At Column 1, in item (72), Lines 2 and 3 of the "Inventors" section, delete "Christopher Hollander, West Newton, MA (US)" and insert --Cristopher Hollander, West Newton, MA (US)--.

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*